(12) United States Patent
Guile et al.

(10) Patent No.: US 6,251,910 B1
(45) Date of Patent: Jun. 26, 2001

(54) 1,2,3-TRIAZOLO[4,5-D]PYRIMIDINES AS $P_{2T}$ RECEPTOR ANTAGONISTS

(75) Inventors: Simon Guile; Anthony Ingall; Brian Springthorpe, all of Loughborough; Paul Willis, Nottingham, all of (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/155,023

(22) PCT Filed: Jul. 15, 1998

(86) PCT No.: PCT/SE98/01393

§ 371 Date: Sep. 21, 1998

§ 102(e) Date: Sep. 21, 1998

(87) PCT Pub. No.: WO99/05143

PCT Pub. Date: Feb. 4, 1999

(30) Foreign Application Priority Data

Jul. 22, 1997 (SE) .................................................. 9702773

(51) Int. Cl.[7] ..................... C07D 487/04; A61K 31/519; A61P 7/02

(52) U.S. Cl. ............................. 514/258; 544/254

(58) Field of Search ............................. 544/254; 514/258

(56) References Cited

U.S. PATENT DOCUMENTS 5,747,496 * 5/1998 Cox et al. .............................. 514/258

FOREIGN PATENT DOCUMENTS

| | | |
|---|---|---|
| 0 215 759 | 3/1987 | (EP) . |
| 0 368 640 A2 | 5/1990 | (EP) . |
| 0 368 640 A3 | 5/1990 | (EP) . |
| 97 03084 | 1/1997 | (WO) . |
| 98/28300 * | 7/1998 | (WO) . |
| 99/05142 * | 2/1999 | (WO) . |
| 99/05144 * | 2/1999 | (WO) . |
| 99/41254 * | 8/1999 | (WO) . |

OTHER PUBLICATIONS

Williams, M. et al, "Ann. Reports Med. Chem, vol. 31", 1996, Academic Press, San Diego, pp. 21–30.*

* cited by examiner

Primary Examiner—Mukund J. Shah
Assistant Examiner—Thomas McKenzie
(74) Attorney, Agent, or Firm—Nixon & Vanderhye

(57) ABSTRACT

Compounds of formula having the following stereochemistry

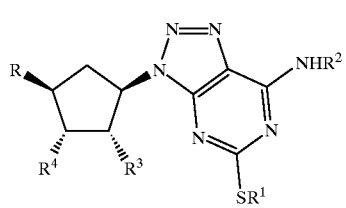

(Ia)

wherein R, $R^1$, $R_2$, $R^3$ and $R^4$ are as defined in the specification. The compounds are useful as $P_{2T}$ receptor antagonists.

14 Claims, No Drawings

1,2,3-TRIAZOLO[4,5-D]PYRIMIDINES AS $P_{2T}$ RECEPTOR ANTAGONISTS

This application is a 371 National Stage application of PCT/SE90/01393, filed Jul. 15, 1998, which claims priority from Swedish applications 9702773-4, filed Jul. 22, 1997 and 9702775-9, filed Jul. 22, 1997.

The present invention provides new triazolo[4,5-d] pyrimidine compounds, their use as medicaments, compositions containing them and processes for their preparation.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty is also compromised by platelet mediated occlusion or re-occlusion.

A number of converging pathways lead to platelet aggregation. Whatever the initial stimulus, the final common event is a cross linking of platelets by binding of fibrinogen to a membrane binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp.1638–1642).

It has been found that ADP acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81–106; Antiplatelet Trialists' Collaboration (1994), *Br. Med. J.* 308, pp.159–168). Aspirin has no effect on aggregation produced by other sources of ADP, such as damaged cells or ADP released under conditions of turbulent blood flow. ADP-induced platelet aggregation is mediated by the $P_{2T}$-receptor subtype uniquely located on the platelet membrane. Recently it has been shown that antagonists at this receptor offer significant improvements over other anti-thrombotic agents. Accordingly there is a need to find $P_{2T}$-antagonists as anti-thrombotic agents.

It has now been found that a series of triazolo[4,5-d] pyrimidine derivatives are $P_{2T}$-receptor antagonists. In a first aspect the invention therefore provides a compound of formula (I):

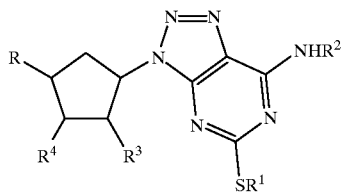

wherein:

$R^1$ is a $C_{1-6}$ alkyl, $C_{2-6}$ alkenyl, $C_{2-6}$ alkynyl, $C_{3-8}$-cycloalkyl or a phenyl group, each group being optionally substituted by one or more substituents selected from halogen, $OR^8$, $NR^9R^{10}$, $SR^{11}$ or $C_{1-6}$ alkyl (itself optionally substituted by one or more halogen atoms);

$R^2$ is $C_{1-8}$ alkyl optionally substituted by one or more substituents selected from halogen, $OR^8$, $NR^9R^{10}$, $SR^{11}$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^8$, $NR^9R^{10}$, $SR^{11}$, $C_{1-6}$-alkyl or phenyl, the latter two groups being optionally substituted by one or more substituents selected from halogen, $NO_2$, $C(O)R^8$, $OR^8$, $SR^{11}$, $NR^{12}R^{13}$, a fused 5- or 6-membered saturated ring containing one or two oxygen atoms, phenyl or $C_{1-6}$-alkyl the latter two groups being optionally substituted by $OR^8$, $NR^9R^{10}$ or one or more halogen atoms;

one of $R^3$ and $R^4$ is hydroxy and the other is hydrogen, hydroxy or $NR^9R^{10}$;

R is a group $(CR^5R^6)_mOR^7$ where m is 0 or 1, $R^5$ and $R^6$ are independently hydrogen, $C_{1-6}$ alkyl or phenyl the latter two groups being optionally substituted by halogen, and $R^7$ is hydrogen, $C_{1-6}$ alkyl or $(CR^5R^6)_nR^{14}$ where $R^5$ and $R^6$ are as defined above, n is 1 to 3 and $R^{14}$ is COOH, $OR^{15}$, $NR^{16}R^{17}$ or $CONR^{16}R^{17}$;

or R is a $C_{1-4}$ alkyl or $C_{2-4}$ alkenyl group, each of which is substituted by one or more groups selected from =S, =O, $=NR^{20}$ or $OR^{21}$ and optionally substituted by one or more groups selected from halogen, $C_{1-4}$ alkyl, phenyl, $SR^{21}$, $NO_2$ or $NR^{22}R^{23}$ (where $R^{21}$, $R^{22}$ and $R^{23}$ are independently hydrogen, $C_{1-4}$ alkyl or phenyl; $R^{20}$ is $OR^{24}$ or $NR^{25}R^{26}$, where $R^{24}$ is hydrogen, $C_{1-4}$ alkyl or phenyl, and $R^{25}$ and $R^{26}$ are independently hydrogen, $C_{1-4}$ alkyl, aryl, $C_{1-6}$ acyl, arylsulphonyl or arylcarbonyl);

$R^8$ is hydrogen, $C_{1-6}$ alkyl optionally substituted by halogen or $R^8$ is phenyl optionally substituted by one or more substituents selected from halogen, $NO_2$, $C(O)R^6$, $OR^6$, $SR^9$, $NR^{10}R^{11}$;

$R^9$, $R^{10}$ and $R^{11}$ are independently hydrogen or $C_{1-6}$ alkyl;

$R^{12}$ and $R^{13}$ are independently hydrogen, $C_{1-6}$ alkyl, acyl, alkyl sulfonyl optionally substituted by halogen, or phenyl sulfonyl optionally substituted by $C_1$–$C_4$ alkyl; and $R^{15}$, $R^{16}$ and $R^{17}$ are independently hydrogen or $C_{1-6}$ alkyl;

or a pharmaceutically acceptable salt or solvate thereof.

Alkyl groups, whether alone or as part of another group, can be straight chained or branched. Compounds of formula (I) are capable of existing in stereoisomeric forms including enantiomers and the invention extends to each of these stereoisomeric forms and to mixtures thereof including racemates. The invention also extends to any tautomeric forms and mixtures thereof.

Preferably the compound of formula (I) has the following stereochemistry:

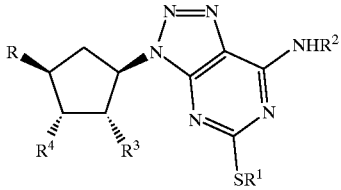

(Ia)

Suitably $R^1$ is a $C_{1-6}$ alkyl, $C_{2-6}$ alkenyl, $C_{2-6}$ alkenyl, $C_{3-8}$-cycloalkyl or a phenyl group, each group being optionally substituted by one or more substituents selected from halogen, $OR^8$, $NR^9R^{10}$, $SR^{11}$ or $C_{1-6}$ alkyl (itself optionally substituted by one or more halogen atoms). Preferably $R^1$ is $C_{1-4}$ alkyl or phenyl each of which can be substituted by trifluoromethyl. More preferably $R^1$ is propyl, butyl, trifluoromethylphenyl or 3,3,3,-trifluoropropyl.

Suitably $R^2$ is $C_{1-8}$ alkyl optionally substituted by one or more substituents selected from halogen, $OR^8$, $NR^9R^{10}$, $SR^{11}$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^8$, $NR^9R^{10}$, $SR^{11}$, $C_{1-6}$-alkyl or phenyl, the latter two groups being optionally substituted by one or more substituents selected from halogen, $NO_2$, $C(O)R^8$, $OR^8$, $SR^{11}$, $NR^{12}R^{13}$, a fused 5- or 6-membered saturated ring containing one or two oxygen atoms, phenyl or $C_{1-6}$-alkyl the latter two groups being optionally substituted by $OR^8$, $NR^9R^{10}$ or one or more halogen atoms. Aryl groups include phenyl and naphthyl groups. Acyl groups include $C(O)C_{1-6}$ alkyl such as acetyl and 1-oxopropyl. Preferably $R^2$ is $C_{1-6}$ alkyl or a $C_{3-8}$-cycloalkyl group optionally substituted by phenyl. More preferably $R^2$ is butyl or cyclopropyl optionally substituted by phenyl, the phenyl group itself being optionally substituted by one or more halogen, $C_{3-8}$ alkyl, alkoxy, phenoxy or phenyl groups.

Suitably one of $R^3$ and $R^4$ is hydroxy and the other is hydrogen, hydroxy or $R^9R^{10}$. Preferably $R^3$ and $R^4$ are both hydroxy.

Suitably R is a group $(CR^5R^6)_mOR^7$ where m is 0 or 1, $R^5$ and $R^6$ are independently hydrogen, $C_{1-6}$ alkyl or phenyl the latter two groups being optionally substituted by halogen, and $R^7$ is hydrogen, $C_{1-6}$ alkyl or $(CR^5R^6)_nR^{14}$ where $R^5$ and $R^6$ are as defined above, n is 1 to 3 and $R^{14}$ is COOH, $OR^{15}$, $NR^{16}R^{17}$ or $CONR^{16}R^{17}$; or R is a $C_{1-4}$ alkyl or $C_{2-4}$ alkenyl group, each of which is substituted by one or more groups selected from $=S$, $=O$, $=NR^{20}$ or $OR^{21}$ and optionally substituted by one or more groups selected from halogen, $C_{1-4}$ alkyl, phenyl, $SR^{21}$, $NO_2$ or $NR^{22}R^{23}$ (where $R^{21}$, $R^{22}$ and $R^{23}$ are independently hydrogen, $C_{1-4}$ alkyl or phenyl; $R^{20}$ is $OR^{24}$ or $NR^{25}R^{26}$, where $R^{24}$ is hydrogen, $C_{1-4}$ alkyl or phenyl, and $R^{25}$ and $R^{26}$ are independently hydrogen, $C_{1-4}$ alkyl, aryl, $C_{1-6}$ acyl, arylsulphonyl or arylcarbonyl).

Preferred R groups include OH, $CH_2OH$, $CH_2CH_2OH$, $OCH_2CH_2OH$, $CH_2OCH_2C(CH_3)_2OH$ and $OCH_2C(CH_3)_2OH$.

Particularly preferred compounds of the invention include those exemplified herein both as free bases and as pharmaceutically acceptable salts and solvates.

According to the invention there is further provided a process for the preparation of a compound of formula (I) which comprises:

(a) reacting a compound of formula (II):

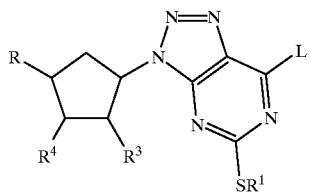

(II)

where R, $R^1$, $R^3$ and $R^4$ are as defined in formula (I) or are protected derivatives thereof or $R^3$ and $R^4$ together form a bond, and L is a leaving group with a compound of formula (III):

$R^2NH_2$ (III)

where $R^2$ is as defined in formula (I) or is a protected derivative thereof, or (b) reacting a compound of formula (IV):

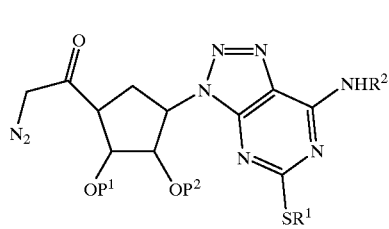

(IV)

in which $R^1$ and $R^2$ are as defined in formula (I) or are protected derivatives thereof and $P^1$ and $P^2$ are protecting groups or hydrogen, with a suitable reagent to introduce a substituent R, or, for compounds where m is 0:

(c) hydroxylation of a compound of formula (V):

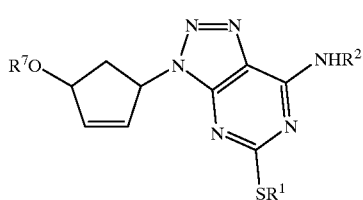

(V)

where $R^1$, $R^2$ and $R^7$ are as defined in formula (I) or are protected derivatives thereof, and optionally thereafter (a), (b) or (c) and in any order:
converting one or more functional groups into a further functional groups
removing any protecting groups
forming a pharmaceutically acceptable salt or solvate.

Compounds of formula (II) can be reacted with amines of formula (III) in the presence of a base such as a tertiary organic amine in an inert solvent such as dichloromethane at ambient or elevated temperature. Other suitable bases include inorganic bases such as potassium carbonate.

When one or both of $R^3$ and $R^4$ are hydroxy they can be protected as groups $OP^1$ and $OP^2$ where $P^1$ and $P^2$ are protecting groups. Examples of suitable protecting groups in compounds of formula (II) and (IV) are $C_{1-6}$ alkyl (preferably methyl), benzyl, $(C_{1-6}alkyl)_3Si$ (preferably t-butyldimethylsilyl), and a C(O)C$_{1-6}$alkyl group such as acetyl. When both of R$^3$ and R$^4$ are hydroxy preferably the two groups P$^1$ and P$^2$ together with the atoms to which they are attached form an alkylidene ring such as a methylidene or isopropylidene ring. Alternatively P$^1$ and P$^2$ can form an alkoxymethylidene ring such as ethoxymethylidene.

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Ester protecting groups can be removed by basic hydrolysis, for example by using a metal hydroxide, preferably an alkali metal hydroxide, such as sodium hydroxide or lithium hydroxide, or quaternary ammonium hydroxide in a solvent, such as aqueous ethanol or aqueous tetrahydrofuran, at a temperature of from 10° to 100° C., preferably the temperature is around room temperature; or by acidic hydrolysis using a mineral acid such as HCl or a strong organic acid such as trichloroacetic acid in a solvent such as aqueous 1,4-dioxane.

Trialkylsilyl protecting groups can be removed by the use of, for example, a fluoride ion source, for example tetra-n-butylammonium fluoride or hydrogen fluoride.

When one or both of P$^1$ and P$^2$ are C$_{1-6}$ alkyl, deprotection can be acheived using boron tribromide.

Benzyl groups can be removed by hydrogenolysis using a transition metal catalyst, for example palladium on charcoal, under an atmosphere of hydrogen, at a pressure of from 1 to 5 bar, in a solvent, such as acetic acid.

A compound of formula (II) can be prepared by diazotising a compound of formula (VI):

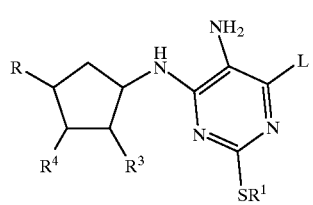

(VI)

wherein R and R$^1$ are as defined in formula (I) and L is as defined above and R$^3$ and R$^4$ are as defined in formula (I) or are protected derivatives thereof or R$^3$ and R$^4$ together form a bond, with a metal nitrite, for example an alkali metal nitrite, especially sodium nitrite in dilute aqueous acid, for example 2M HCl, or with a C$_{1-6}$-alkyl nitrite in an inert solvent, at a temperature of from –20 to 100° C.; preferred conditions are isoamyl nitrite in acetonitrile at 80° C.

A Compound of formula (VI) wherein R is CH$_2$OH, and R$^3$ and R$^4$ are hydroxyl or protected derivatives thereof, L is as defined above, can be prepared by reducing a compound of formula (VII):

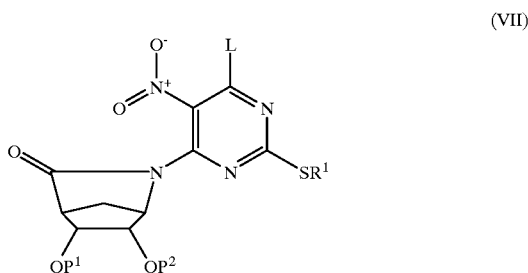

(VII)

wherein R$^1$, L, P$^1$ and P$^2$ are as defined above. The reduction of the nitro group can be carried out for example by using hydrogenation with a transition metal catalyst at a temperature around room temperature, for example palladium on charcoal under an atmosphere of hydrogen, preferably at a pressure from 1 to 5 atmospheres, in a solvent, for example ethanol, or by using iron in an acidic solvent such as acetic acid at a temperature of about 100° C.

Reduction of the lactam can be carried out using complex metal hydrides such as lithium aluminium hydride in a solvent such as ether or preferably by using sodium borohydride in a suitable solvent such as methanol.

A compound of formula (VII) can be prepared by reacting a compound of formula (VIII):

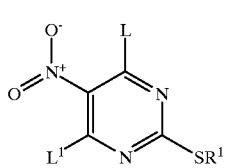

(VIII)

wherein L and R$^1$ are as defined above and L$^1$ is a leaving group, for example a halogen atom, wherein L and L$^1$ are preferably the same, with a compound of formula (IX):

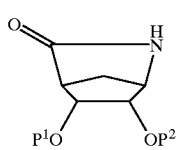

(IX)

wherein P$^1$ and P$^2$ are as defined above, in the presence of a base such as C$_{1-6}$-alkyl-M or MH wherein M is a metal ion, for example n-butyl lithium, in an inert solvent, such as tetrahydrofuran (THF), at a temperature of from –10 to 100° C. Preferably sodium hydride is used in THF at room temperature. Preferably the compound of formula (IX) has the following stereochemistry such that the above reactions give a compound of formula (Ia):

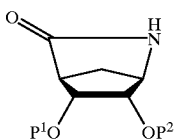

(IXa)

One or more functional groups can be converted into further functional groups using standard chemistry. For example a compound where $R^7$ is hydrogen can be converted to a compound where $R^7$ is $CH_2COOH$ by treating with a compound of formula (X):

$$R^{18}OCOCH=N_2 \tag{X}$$

where $R^{18}$ is $C_{1-6}$ alkyl in the presence of rhodium acetate, followed by hydrolysis of the resulting ester. A compound where $R^7$ is hydrogen can be converted to a compound where $R^7$ is $(CH_2)_nR^{14}$ by treatment with base followed by $L(CH_2)_nR^{14}$ where L is a leaving group and $R^{14}$ is as defined above or a protected version thereof. The group $SR^1$ can be interconverted by oxidation of the sulfur, for example using oxone™ or MCBPA, followed by treatment with a compound $R^{1'}$—SM where $R^{1'}$ is a different $R^1$ group and M is a metal such as sodium.

Compounds of formula (IV) can be reacted with a suitable reagent to introduce the R group using conventional chemistry. For example compounds of formula (IV) can be reacted with $Zn/H_2SO_4$ to give a compound of formula (I) where R is $COCH_2OH$; with HI to give a compound of formula (I) where R is $COCH_3$; or with $BF_3/R'OH$ (e.g. methanol) to give a compound of formula (I) where R is $COCH_2OR'$, or with light followed by a reducing agent (eg DIBAL-H) to give a compound of formula (I) where R is $CH_2CH_2OH$.

Compounds of formula (IV) can be prepared from compounds of formula (XI):

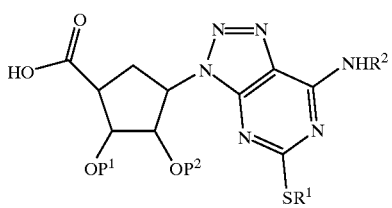

(XI)

in which $R^1$, $R^2$, $P^1$ and $P^2$ are as defined above by treatment with an activating agent, such as an acyl chloride, followed by diazomethane. Compounds of formula (XI) can be prepared from compounds of formula (VII) as defined above by reduction of the nitro group followed by hydrolysis. Hydrolysis can be performed using a mineral acid such as HCl or a strong organic acid such as trifluoroacetic acid. Preferably the reduction and hydrolysis are carried out simultaneously using iron in an alcoholic solvent, for example ethanol, containing an alkaline earth halide such as calcium chloride at a temperature of about 80° C.

Compounds of formula (VI) can also be prepared by treating a compound of formula (XII)

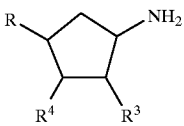

(XII)

where $R^3$ and $R^4$ are as defined in formula (I) or are protected derivatives thereof or $R^3$ and $R^4$ together form a bond with a compound of formula (VIII) as defined above, followed by reduction of the nitro group. The reaction is carried out in an inert solvent such as dichloromethane or 1,4-dioxane in the presence of a non-nucleophilic base such as N,N-diisopropylamine at a temperature of about –20° C. to about 150° C., preferably at ambient temperature.

Preferably the compound of formula (XII) has the following stereochemistry such that the above reactions give a compound of formula (Ia) as defined above

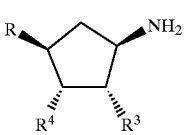

(XIIa)

Compounds of formula (VI) where $R^3$ and $R^4$ form a bond and L is $SR^1$ can be prepared by reacting a compound of formula (XIII):

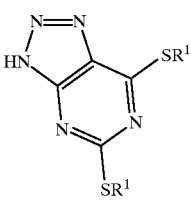

(XIII)

in which $R^1$ groups are as defined in formula (I) with a compound of formula (XIV):

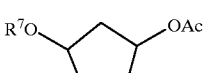

(XIV)

in which $R^5$ is as defined in formula (I). The reaction can be carried out in the presence of a suitable transition metal complex, preferably tetrakistriphenylphosphine palladium (0).

Compounds of formula (XIII) can be prepared from compounds of formula (XV):

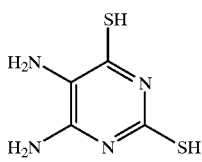

(XV)

by reacting with a compound $R^1X$ where $R^1$ is as defined in formula (I) and X is a leaving group such as halo, followed by cyclisation.

The amines $R^2NH_2$ can be prepared using procedures described in H Nishiyama etal, Bull. Chem. Soc., Jpn, 1995, 68, 1247, P. Newman, Optical Resolution Procedures for Chemical Compounds, Vol. 1, Amines and Related Compounds; Optical Resolution and Information Centre: Manhattan College, Riverdale, N.Y., 1978, p120, J. Vallgarda etal, J. Chem. Soc. Perkin 1, 1994, 461. Certain amines $R^2NH_2$ are novel compounds and form a further aspect of the invention.

All novel intermediates form a further aspect of the invention.

Salts of the compounds of formula (I) may be formed by reacting the free acid, or a salt thereof, or the free base, or a salt or a derivative thereof, with one or more equivalents of the appropriate base (for example ammonium hydroxide optionally substituted by $C_{1-6}$-alkyl or an alkali metal or alkaline earth metal hydroxide) or acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, THF or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_{2T}$ receptor antagonists. Accordingly, the compounds are useful in therapy, especially adjunctive therapy, particularly they are indicated for use as: inhibitors of platelet activation, aggregation and degranulation, promoters of platelet disaggregation, anti-thrombotic agents or in the treatment or prophylaxis of unstable angina, coronary angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process.

According to the invention there is further provided the use of a compound according to the invention in the manufacture of a medicament for the treatment of the above disorders. In particular the compounds of the invention are useful for treating myocardial infarction, thrombotic stroke, transient ischaemic attacks, peripheral vascular disease and angina, especially unstable angina. The invention also provides a method of treatment of the above disorders which comprises administering to a patient suffering from such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

The invention is illustrated by the following examples. In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as (SiO₂)) was carried out using Fisher Matrix silica, 35–70 μm. For examples which showed the presence of rotamers in the proton NMR spectra only the chemical shifts of the major rotamer are quoted.

For compounds prepared by parallel synthesis the products were taken into ethanol (500 μl) and analysed using an analytical HPLC machine (HP1100), against a standard calibration curve, in order to estimate the concentration of the product. The ethanol was evaporated and the residue taken into an appropriate volume of DMSO, based on the HPLC analysis, to yield a solution of 5 mM concentration for biological testing.

EXAMPLE 1

[1S-[1α,2α,3β,5β(1S*,2R*)]]-3-(Hydroxymethyl)-5-[7-[(2-phenylcyclopropyl)amino]-5-(propylthio)-3H-1,2,3-triazolo[4,5-d]pyrimidin-3-yl]-cyclopentane-1,2-diol a) [3aR-[3aα,4α,6α(1R*,2S*),6aα]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4methanol N,N-Diisopropylethylamine (21 ml) was added to a solution of [3aR-(3aα,4α,6α,6aα)]-6-[7-chloro-5-(propylthio)-3H-1,2,3-triazolo[4,5-d]pyrimidin-3-yl]-tetrahydro-2,2dimethyl-4H-cyclopenta-1,3-dioxole4-methanol (prepared as described in WO 9703084) (55 g) and (1R-trans)-2-phenyl-cyclopropanamine, [R-(R*,R*)]-2,3-dihydroxybutanedioate (1:1) (prepared as described by L. A. Mitscher et al., J. Med. Chem. 1986, 29, 2044) (11.3 g) in dichloromethane (500 ml). The reaction mixture was stirred at room temperature for 3 hours, then washed with water, dried and evaporated. The residue was purified (SiO₂, ethyl acetate:dichloromethane 3:7 as eluant) to afford the subtitle compound (19 g).

MS (APCI) 497 (M+H⁺, 100%)

b) [1S-[1α,2α,3β,5β(1S*,2R*)]]-3-(Hydroxymethyl)-5-[7-[(2-phenylcyclopropyl)amino]-5-(propylthio)-3H-1,2,3-triazolo[4,5-d]pyrimidin-3-yl]-cyclopentane-1,2-diol A solution of the product from step (a) (18.5 g) in methanol (1 L) and 2N HCl (150 ml) was stirred at room temperature for 2 hours and concentrated in vacuo. Water (500 ml) was added and the product was collected by filtration and dried (16.7 g).

MS (APCI) 457 (M+H⁺, 100%)

NMR δH (d₆-DMSO) 9.33 (1H, d), 7.30–7.16 (5H, m), 5.01 (2H, m), 4.72 (2H, m), 4.43 (1H, m), 3.87 (1H, d), 3.48 (2H, m), 3.20 (1H, m), 2.95 and 2.85 (2H, 2×m), 2.26 (1H, m), 2.12 (2H, m), 1.85 (1H, m), 1.49 (3H, m), 1.33 (1H, m), 0.82 (3H, t).

EXAMPLE 2

[1R-(1α,2α,3β,5β)]-3-[7-[(Cyclopropyl)amino]-5-(propylthio)-3H-1,2,3-triazolo[4,5-d]pyrimidin-3-yl]-5-(hydroxymethyl)-cyclopentane-1,2-diol a) [3aR-(3aα4α,6α,6aα)]-6-[7-[(Cyclopropyl)amino]-5-(propylthio)-3H-1,2,3-triazolo[4,5-d]pyrimidin-3-yl]-tetrahydro-2,2-dimethyl-4H-cyclopenta-1,3-dioxole-4-methanol A solution of [3aR-(3aα,4α,6α,6aα)]-6-[7-chloro-5-(propylthio)-3H-1,2,3-triazolo[4,5-d]pyrimidin-3-yl]-tetrahydro-2,2-dimethyl-4H-cyclopenta-1,3-dioxole-4-methanol (0.5 g) and cyclopropanamine (0.3 ml) in 1,4-dioxane (20 ml) was heated to reflux. The heat source was removed and the reaction mixture was stirred for 1 hour. The mixture was concentrated and the residue purified (SiO₂, ethyl acetate: isohexane 1:1 as eluant) to afford the subtitle compound (0.4 g).

MS (APCI) 421 (M+H⁺, 100%)

b) [1R-(1α,2α,3β,5β)]-3-[7-[(Cyclopropyl)amino]-5-(propylthio)-3H-1,2,3-triazolo[4,5-d]pyrimidin-3-yl]-5-(hydroxymethyl)-cyclopentane-1,2-diol A solution of the product from step (a) (0.12 g) in trifluoroacetic acid (4 ml)/water (1 ml) was stirred at room temperature for 2 hours, poured into dilute aqueous sodium bicarbonate and extracted with dichloromethane. The extract was concentrated and purified (SiO₂, ethyl acetate as eluant) to afford the title compound (0.10 g).

MS (APCI) 381 (M+H⁺, 100%)

NMR δH (d₆-DMSO) 9.00 (1H, s), 5.00 (2H, m), 4.70 (2H, m), 4.45–4.40 (1H, m), 3.90 (1H, br s), 3.50–3.40 (2H, m), 3.10–3.00 (3H, m), 2.25–2.20 (1H, m), 2.19–2.16 (1H, m), 1.90–1.80 (1H, m), 1.80–1.60 (2H, m), 1.00 (3H, t), 0.90–0.60 (4H, m).

EXAMPLE 3

[1R-(1α,2α,3β,5β)]-3-[7-(Butylamino)-5-(propylthio)-3H-1,2,3-triazolo[4,5-d]pyrimidin-3-yl]-5-(hydroxymethyl)-cyclopentane-1,2-diol The title compound was prepared from [3aR-(3aα,4α,6α,6aα)]-6-[7-(butylamino)-5-(propylthio)-3H-1,2,3-triazolo[4,5-d]pyrimidin-3-yl]-tetrahydro-2,2-dimethyl4H-cyclopenta-1,3-dioxole-4-methanol (prepared as described in WO 9703084) according to the method of example 2 step (b).

MS (FAB) 397 (M+H+, 100%)

NMR δH (d<sub>6</sub>-DMSO) 6.25 (1H, m), 5.15 (1H, s), 5.00 (1H, m), 4.45 (1H, m), 4.25 (1H, s), 3.90–3.60 (4H, m), 3.10 (2H, m), 2.94 (1H, s), 2.75 (1H, m), 2.45 (1H, m), 2.20 (1H, m) 2.05 (1H, m), 1.78 (2H, m), 1.65 (2H, m), 1.46 (2H, m), 1.07 (3H, t), 1.00 (3H, t).

EXAMPLE 4

[1R-(1α,2α,3β,5β)]-3-[7-(Butylamino)-5-[[4-(trifluoromethyl)phenyl]thio]-3H-1,2,3-triazolo[4,5-d]pyrimidin-3-yl]-5-(hydroxymethyl)-cyclopentane-1,2-diol a) [3aR-(3aα,4α,6α,6aα)]-6-[7-(Butylamino)-5-(propylsulfonyl)-3H-1,2,3-triazolo[4,5-d]pyrimidin-3-yl]-tetrahydro-2,2-dimethyl-4H-cyclopenta-1,3-dioxole-4-methanol 3-Chloroperoxybenzoic acid (1.0 g) was added to a solution of [3aR-(3a,α,4α,6α,6aα)]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-methanol (0.88 g) in dichloromethane (100 ml) and the resulting solution was stirred at room temperature for 18 hours. The solution was washed with aqueous sodium metabisulfite solution (3×10 ml) then dried and concentrated. Purification (SiO<sub>2</sub>, ethyl acetate as eluant) afforded the subtitle compound (0.3 g).

MS (APCI) 469 (M+H+, 100%)

b) [3aR-(3aα,4α,6α,6aα)]-6-[7-(Butylamino)-5-[[4-(trifluoromethyl)phenyl]thio]-3H-1,2,3-triazolo[4,5-d]pyrimidin-3-yl]-tetrahydro-2,2-dimethyl-4H-cyclopenta-1,3-dioxole-4-methanol 4-(Trifluoromethyl)thiophenol (0.18 g) was added to a suspension of sodium hydride (60%, 40 mg) in THF (10 ml). After 30 minutes a solution of the product of step (a) (0.23 g) in THF (10 ml) was added dropwise and the reaction stirred for 45 minutes. The reaction mixture was added slowly to a solution of sodium chloride (10 ml) containing acetic acid (1 ml) then the solution extracted with ethyl acetate (50 ml). The organic phase was dried and concentrated and the residue purified (SiO<sub>2</sub>, diethyl ether to diethyl ether:ethanol 9:1 as eluant) to give the subtitle compound.

MS (APCI) 539 (M+H+, 100%)

c) [1R-(1α,2α,3β,5β)]-3-[7-(Butylamino)-5-[[4-(trifluoromethyl)phenyl]thio]-3H-1,2,3-triazolo[4,5-d]pyrimidin-3-yl]-5-(hydroxymethyl)-cyclopentane-1,2-diol Prepared according to the method of example 2, step (b), using the the product of step (b).

MS (APCI) 469 (M+H+, 100%)

NMR δH (d<sub>6</sub>-DMSO) 9.08 (1H, m), 7.88–7.78 (4H, dd), 5.00–4.91 (2H, m), 4.71–4.64 (2H, m), 4.36–4.30 (1H, m), 3.80–3.75 (1H, m), 3.42–3.17 (1H, m), 3.29–3.15 (2H, m), 2.52–2.08 (3H, m), 1.80–1.70 (1H, m), 1.37–1.32 (2H, m), 1.17–1.07 (2H, m), 0.77 (3H, t).

EXAMPLE 5

2-[[[1R-(1α,2β,3β,4α)]-4-[7-(Butylamino)-5-(propylthio)3H-1,2,3-triazolo[4,5-d]pyrimidin-3-yl]-2,3-dihydroxy-cyclopentyl]methoxy]acetic acid a) [3aR-(3aα,4α,6α,6aα)]-2-[6-[7-(Butylamino)5-(propylthio)-3H-1,2,3-triazolo[4,5-d]pyrimidin3-yl]-tetrahydro-2,2-dimethyl-4H-cyclopenta-1,3-dioxole-4-methoxy]acetic acid, ethyl ester A solution of [3aR-(3aα,4α,6α,6aα)]-6-[7-chloro-5-(propylthio)-3H-1,2,3-triazolo[4,5-d]pyrimidin-3-yl]-tetrahydro-2,2-dimethyl-4H-cyclopenta-1,3-dioxole-4-methanol (0.7 g) and rhodium acetate (0.39 g) in dichloromethane (20 ml) was treated with a solution of ethyl diazoacetate (0.21 ml) in dichloromethane (10 ml) over 3 hours. The reaction mixture was stirred at room temperature for 60 hours, concentrated and purified (SiO<sub>2</sub>, isohexane-:ethyl acetate 3:1 as eluant). The resulting intermediate was taken into 1,4-dioxane (10 ml), n-butylamine (0.2 ml) added and the solution stirred for 18 hours then concentrated. Purification (SiO<sub>2</sub>, dichloromethane to dichloromethane:ethyl acetate 8:2 as eluant) gave the subtitle compound (0.2 g).

MS (FAB) 523 (M+H+, 100%)

b) 2-[[[1R-(1α,2β,3β,4α)]-4-[7-(Butylamino)-5-(propylthio)-3H-1,2,3-triazolo[4,5-d]pyrimidin-3-yl]-2,3-dihydroxy-cyclopentyl]methoxy]acetic acid, ethyl ester Prepared according to the method of example 2, step b) using the product of step a).

MS (FAB) 483 (M+H+, 100%)

c) 2-[[[1R-(1α,2β,3β,4α)]4-[7-(Butylamino)-5-(propylthio)-3H-1,2,3-triazolo[4,5-d]pyrimidin-3-yl]-2,3-dihydroxy-cyclopentyl]methoxy]acetic acid A mixture of the product from step (c) (96 mg) and lithium hydroxide monohydrate (8.5 mg) in tetrahydrofuran (10 ml) was stirred for 18 hours then concentrated. Purification (SiO<sub>2</sub>, dichloromethane to ethyl acetate to ethyl acetate:methanol 9:1 gradient elution) afforded the title compound (0.04 g).

MS (FAB) 455 (M+H+, 100%)

NMR δH (d<sub>6</sub>-DMSO) 12.60 (1H, m), 8.97 (1H, m), 4.99 (2H, m), 4.82 (1H, m), 4.42 (2H, m), 4.04 (2H, m), 3.92 (2H, m), 3.60–3.51 (1H, m), 3.50–3.40 (3H, m), 3.10–3.00 (2H, t), 2.30–2.20 (2H, m), 1.88 (1H, m), 1.67 (2H, m), 1.55 (4H, m), 1.33 (2H, m), 1.07–0.83 (6H, m).

EXAMPLE 6

1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-2-hydroxy-ethanone a) [3aR-(3aα,4α,6α,6aα)]-6-[[5-Amino-6-chloro-2-(propylthio)-4-pyrimidinyl]amino]-tetrahydro-2,2-dimethyl-4H-cyclopenta-1,3-dioxole-4-carboxylic acid Iron powder (10.0 g) was added to a stirred solution of [3aS-(3aα,4β,7β,7aα)]-5-[6-chloro-5-nitro-2-(propylthio)- pyrimidin4-yl]-tetrahydro-4,7-methano-2,2-dimethyl-1,3-dioxolo[4,5-c]pyridin-6(3aH)-one (prepared as described in WO 9703084) (10.0 g), and calcium chloride in ethanol (140 ml). The reaction mixture was heated at reflux for 10 minutes then filtered through celite, washing several times with hot ethanol. The filtrate was concentrated to afford the subtitle compound (9.3 g).

MS (FAB) 405, 403 (M+H$^+$), 405 (100%).

b) [3aR-(3aα,4α,6α,6aα)]-6-[7-Chloro-5-(propylthio)-3H-1,2,3-triazolo[4,5-d]pyrimidin-3-yl]-tetrahydro-2,2-dimethyl-4H-cyclopenta-1,3-dioxole-4-carboxylic acid Isoamyl nitrite (6.02 ml) was added to a solution of the product of step a) (9.28 g) in acetonitrile (80 ml) and the solution heated at 70° C. for 1 hour. The cooled reaction mixture was concentrated and purified (SiO$_2$, ethyl acetate:isohexane 2:1 as eluant) to afford the subtitle compound (7.9 g).

MS (FAB) 416, 414 (M+H$^+$), 414 (100%).

c) [3aR-(3aα,4α,6α,6aα)]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxylic acid Prepared according to the method of Example 1, step a) using the product of step b).

MS (APCI) 511 (M+H$^+$, 100%).

d) 1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-2-hydroxy-ethanone Isobutylchloroformate (0.38 ml) was added to an ice-cooled solution of the product of step c) (0.50 g) and N-methylmorpholine (0.11 ml) in tetrahydrofuran (20 ml). The solution was then stirred at room temperature for 90 minutes before adding to a solution of diazomethane (1.0 g) in ether (100 ml). The solution was stirred for 30 minutes then concentrated and the diazoketone purified (SiO$_2$, isohexane:diethylether 1:1 as eluant). The diazoketone (0.25 g) was taken into 1,4-dioxane (10 ml)/2N sulphuric acid (10 ml) then heated at 40° C. for 2 hours. The reaction mixture was extracted into ethyl acetate and the extracts washed with water then dried and concentrated. Purification (HPLC, Novapak® C18 column, 0.1% aqueous ammonium acetate:acetonitrile, gradient elution 70:30 to 0:100 over 15 minutes) afforded the title compound (0.09 g).

MS (APCI) 485 (M+H$^+$, 100%)

NMR δH (d$_6$-DMSO) 9.36 (1H, d), 7.31–7.15 (5H, m), 5.24 (2H, t), 5.13 (1H, t), 5.01 (1H, m), 4.33 (1H, m), 4.23 (2H, m), 4.13 (1H, m), 3.18 (2H, m), 2.96–2.94 (1H, m), 2.96–2.84 (1H, m), 2.30 (2H, m), 2.13(1H, m), 1.49 (3H, m), 1.34 (1H, m), 0.81 (3H, t).

EXAMPLE 7

1-[[1S-[1α,2β,3β,4α]]-4-[7-(Butylamino)-5-(propylthio)-3H-1,2,3-triazolo[4,5-d]pyrimidin-3-yl]-2,3-dihydroxy-cyclopentyl]-2-hydroxy-ethanone a) [3aR-(3aα,4α,6α,6aα)]-6-[7-(Butylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid The title compound was prepared according to the method of Example 1, step a) using the product of example 6, step b) and butylamine.

MS (APCI) 411 (M+H$^+$, 100%).

b) 1-[[1S-[1α,2β,3β,4α]]-4-[7-(Butylamino)-5-(propylthio)-3H-1,2,3-triazolo[4,5-d]pyrimidin-3-yl]-2,3-dihydroxy-cyclopentyl]-2-hydroxy-ethanone Prepared according to the method of Example 6, step d) using the product of step a).

MS (APCI) 425 (M+H$^+$, 100%)

NMR δH (d$_6$-DMSO) 9.00 (1H, t), 5.26 (1H, t), 5.24 (1H, t), 5.14 (1H, t), 5.03 (1H, m), 4.38 (1H, m), 4.21 (1H, m), 4.13 (1H, m), 3.51 (2H, m), 3.15 (1H, m), 3.09 (1H, m), 2.30 (2H, m), 1.73 (1H, m), 1.61 (2H, m), 1.38 (2H, m), 1.09 (3H, t), 0.91 (3H, t).

EXAMPLE 8

1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-ethanone Isobutylchloroformate (2.54 ml) was added to an ice-cooled solution of the product of Example 6, step c) (2.00 g) and N-methylmorpholine (0.52 ml) in tetrahydrofuran (50 ml). The solution was stirred at room temperature for 90 minutes before adding to a solution of diazomethane (4.0 g) in ether (200 ml). The reaction mixture was then stirred for 30 minutes and concentrated. The crude diazoketone (2.05 g) was dissolved in chloroform (50 ml), 47% aqueous HI (25 ml) was added and the solution stirred at room temperature for 10 minutes before adding saturated sodium thiosulphate solution (100 ml). The reaction mixture was extracted with dichloromethane and the extracts washed with water, dried and concentrated. The residue was taken into methanol (300 ml), filtered and the filtrate concentrated to 1/4 volume before adding trifluoroacetic acid: water (1:1) (50 ml). After 2 hours the mixture was concentrated and the residue purified (SiO$_2$, ethyl acetate:dichloromethane 1:3 as eluant, then HPLC, Novapak® C18 column, 0.1% aqueous ammonium acetate:acetonitrile, gradient elution 60:40 to 0:100 over 15 minutes) to afford the title compound (0.11 g).

MS (APCI) 469 (M+H$^+$, 100%)

NMR δH (d$_6$-DMSO) 9.35 (1H, d), 7.31–7.15 (5H, m), 5.21 (2H, m), 4.99 (1H, m), 4.27 (1H, m), 4.17 (1H, m), 3.21 (1H, m), 3.10 (1H, m), 2.95–2.83 (2H, m), 2.35 (2H, m) 2.22 (3H, s), 2.13 (1H, m), 1.50 (3H, m), 1.33 (1H, m), 0.81 (3H, t).

EXAMPLE 9

1-[[1S[-1α,2β,3β,4α]-4-[7-(Butylamino)-5-(propylthio)3H-1,2,3-triazolo[4,5-d]pyrimidin-3-yl]-2,3-dihydroxy-cyclopentyl]-ethanone The title compound was prepared according to the method of Example 8 using the product of Example 7, step a).

MS (APCI) 409 (M+H$^+$, 100%)

NMR δH (d$_6$-DMSO) 8.98 (1H, t), 5.22 (2H, m), 5.00 (1H, q), 4.27 (1H, m), 4.19 (1H, m), 3.48 (2H, m), 3.13 (3H, m), 2.32 (2H, m), 2.23 (3H, s), 1.71 (2H, m), 1.63 (2H, m), 0.98 (3H, m), 0.91 (3H, t).

EXAMPLE 10

[1S-[1α,2α,3β,5β(1S*,2R*)]]-3-(1-Hydroxy-1-methylethyl)-5-[7-[(2-phenylcyclopropyl)amino]-5-(propylthio)-3H-1,2,3-triazolo[4,5-d]pyrimidin-3-yl]-cyclopentane-1,2-diol Methylmagnesium bromide (3M solution in diethyl ether, 4 ml) was added to a solution of the product of Example 8

(0.15 g) in tetrahydrofuran and the solution stirred at room temperature for 30 minutes before adding ice/water (3 ml), followed by 1N hydrochloric acid (1 ml). The reaction mixture was extracted into ethyl acetate and the extracts washed with water, dried and concentrated. Purification (HPLC, Novapak® C18 column, 0.1% aqueous ammonium acetate:acetonitrile, gradient elution 70:30 to 0:100 over 15 minutes) gave the title compound (0.13 g).

MS (APCI) 485 (M+H+, 100%)

NMR δH (d$_6$-DMSO) 9.34 (1H, d), 7.31–7.15 (5H, m), 4.90 (2H, m), 4.57 (1H, m), 4.35 (3H, m), 3.93 (1H, m), 3.22 (1H, m), 2.97–2.51 (2H, m), 2.07 (3H, m), 1.95 (1H, s), 1.51 (3H, m), 1.33 (1H, m), 1.31 (3H, s), 1.18 (3H, s), 0.80 (3H, t).

EXAMPLE 11

[1S-[1α,2α,3β,5β(1S*,2R*)]]-3-(2-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol a) [1R-[1α,2β,3β,4α(1R*,2S*)]]-2,3-Dihydroxy-4-[7-[(2-phenylcyclopropyl)amino]-5-(propylthio)-3H-1,2,3-triazolo[4,5-d]pyrimidin-3-yl]-cyclopentaneacetic acid, ethyl ester Isobutylchloroformate (2.54 ml) was added to an ice-cooled solution of the product of Example 6, step c) (2.00 g) and N-methylmorpholine (0.52 ml) in tetrahydrofuran (50 ml). The solution was stirred at room temperature for 90 minutes then added to a solution of diazomethane (4.0 g) in ether (200 ml). The solution was stirred for 30 minutes then concentrated. The crude diazoketone (1.50 g) was taken into methanol (100 ml), cooled in ice/water and irradiated with a 400 W mercury lamp for 10 minutes. The solution was concentrated and purified (HPLC, Novapak® C18 column, 0.1% aqueous ammonium acetate:acetonitrile, gradient elution 40:60 to 0:100 over 15 minutes) to afford the subtitle compound (0.39 g).

MS (APCI) 539 (M+H+, 100%).

b) [1S-[1α,2α,3β,5β(1S*,2R*)]]-3-(2-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol DIBAL-H® (1.5 M solution in toluene, 2 ml) was added to an ice-cooled solution of the product of step a) (0.35 g) in toluene (20 ml) and the solution stirred at this temperature for 30 minutes before adding ethyl acetate (2 ml). The solution was concentrated and the residue was taken into trifluoroacetic acid (15 ml)/water (15 ml) and stirred for 30 minutes. The reaction mixture was concentrated and the residue taken into methanol (10 ml) and 10% aqueous potassium carbonate solution (5 ml) added. After 30 minutes the reaction mixture was extracted with ethyl acetate and washed with water, dried and concentrated. Purification (HPLC, Novapak® C18 column, 0.1% aqueous ammonium acetate:acetonitrile, gradient elution 60:40 to 0:100 over 15 minutes) afforded the title compound (0.21 g).

MS (APCI) 471 (M+H+, 100%)

NMR δH (d$_6$-DMSO) 9.33 (1H, d), 7.31–7.15 (5H, m), 5.00 (1H, d), 4.96 (1H, m), 4.77 (1H, d), 4.51 (1H, t), 4.39 (1H, m), 3.76 (1H, m), 3.45 (2H, m), 3.18 (1H, m), 2.87 (2H, m), 2.37 (1H, m), 2.13 (1H, m), 2.03 (1H, m), 1.75 (2H, m), 1.51 (4H, m), 1.34 (1H, m), 0.83 (3H, t).

EXAMPLE 12

1S-[1α,2β,3β,4α(1S*,2R*)]]-4-[7-[(2-Phenylcyclopropyl)amino]-5-(propylthio)-3H-1,2,3-triazolo[4,5-d]pyrimidin-3-yl]-cyclopentane-1,2,3-triol a) (1S-cis)-4-[[6-Chloro-5-nitro-2-(propylthio)-pyrimidin-4-yl]amino]-2-cyclopentene-1-ol To a solution of 4,6-dichloro-5-nitro-2-propylthiopyrimidine (prepared as described in WO 9703084) (4.00 g) and triethylamine (2.00 ml) in dry tetrahydrofuran (THF) (100 ml) was added a solution of [1S-cis]-4-amino-2-cyclopenten-1-ol (prepared as described by S. F. Martin et al., Tetrahedron Lett., 1992, 33, 3583) (1.48 g) in THF/1,4-dioxane 2:1 (150 ml) dropwise over 1 hour. The reaction mixture was filtered, concentrated and purified (SiO$_2$, ethyl acetate:isohexane 1:4 to 1:1 as eluant) to afford the subtitle compound (3.18 g).

MS (APCI) 313 (M−H$_2$O+H+, 100%)

b) (1S-cis)-4-[[5-Amino-6-chloro-2-(propylthio)-pyrimidin-4-yl]amino]-2-cyclopentene-1-ol Iron powder (2.30 g) was added to a stirred solution of the product of step (a) (2.61 g) in acetic acid (100 ml). The reaction mixture was stirred at room temperature for 2 hours, concentrated to half volume, diluted with ethyl acetate and washed with water. The organic phase was dried and concentrated to afford the subtitle compound (2.28 g).

NMR δH (d$_6$-DMSO) 7.03 (1H, d), 5.93–5.90 (1H, m), 5.85–5.82 (1H, m), 5.05 (1H, d), 4.91–4.85 (2H, m), 4.66–4.60 (1H, m), 2.94 (2H, t), 2.77–2.68 (1H, m), 1.69–1.57 (2H, sextuplet), 1.48–1.42 (1H, quintuplet), 0.94 (3H, t).

c) (1S-cis)-4-[7-Chloro-5-(propylthio)-3H-1,2,3-triazolo[4,5-d]pyrimidin-3-yl]-2-cyclopentene-1-ol Prepared according to the method of example 6, step b) using the product of step b).

MS (APCI) 312 (M+H+), 224 (100%)

d) (1R-trans)-N-[(2,4-Dimethoxyphenyl)methyl]-2-phenyl-cyclopropanamine

A solution of (1R-trans)-2-phenyl-cyclopropanamine, [R-(R*,R*)]-2,3-dihydroxybutanedioate (1:1) (prepared as described by L. A. Mitscher et al., J. Med. Chem. 1986, 29, 2044) (1.92 g) in 1N aqueous NaOH (50 ml) was stirred for 10 minutes and extracted with dichloromethane. The extract was dried, evaporated and the residue was dissolved in methanol (30 ml). To this was added 2,4-dimethoxybenzaldehyde (1.12 g) and the pH adjusted to 5 with acetic acid. Sodium cyanoborohydride (0.46 g) was added. The mixture was stirred overnight, basified with 2N NaOH and extracted with ethyl acetate. The extract was dried, evaporated and purified (SiO$_2$, methanol:dichloromethane: 0.880 ammonia 2:98:0.1 as eluant) to afford the subtitle compound (1.10 g).

NMR δH (CDCl$_3$) 7.23–6.97 (6H, m), 6.49–6.41 (2H, m), 3.73 (3H, s), 3.69 (3H, s), 3.66 (2H, s), 2.21–2.16 (1H, m), 1.82–1.76 (1H, m), 1,01–0.87 (2H, m).

e) [1S-[1α,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-2-cyclopentene-1-ol A solution of the product from step (c) (0.73 g), the product from step (d) (0.73 g) and N,N- diisopropylethylamine (815 μl) in 1,4-dioxane (25 ml) was stirred at room temperature for 1 hour. The reaction mixture was concentrated and the residue purified (SiO$_2$, ethyl acetate:hexane 1:2 as eluant) to afford the subtitle compound (1.18 g).

MS (APCI) 559 (M+H$^+$, 100%)

f) [1S-[1α,2β,3β,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-cyclopentane-1,2,3-triol To a solution of the product of step (e) (0.50 g) in acetone (10 ml) and water (7 ml) was added N-methylmorpholine-N-oxide (0.38 g) followed by osmium tetroxide (390 μl, 2.5% solution in t-butanol). The mixture was stirred at room temperature overnight then treated with sodium hydrosulphite (0.90 g). The suspension was filtered through celite and the product purified (SiO$_2$, ethyl acetate:hexane 1:1 as eluant) to afford the subtitle compound (0.22 g).

MS (APCI) 593 (M+H$^+$,100%)

g) [1S-[1α,2β,3β,4α(1S*,2R*)]]-4-[7-[2-(Phenylcyclopropyl)amino]-5-(propylthio)-3H-1,2,3-triazolo[4,5-d]pyrimidin-3-yl]-cyclopentane-1,2,3-triol Prepared according to the method of example 2, step b) using the product of step f). Purification (HPLC, Novapak® C18 column, 0.1% aqueous ammonium acetate:acetonitrile, 60:40) afforded the title compound (0.12 g).

MS (APCI) 443 (M+H$^+$,100%)

NMR δH (d$_6$-DMSO) 7.29 (2H, m), 7.16 (3H, m), 5.11–4.91 (3H, m), 4.97 (1H, q), 4.67 (1H, m), 3.93 (1H, br s), 3.78 (1H, m), 3.22 (1H, quintet), 2.95–2.81 (2H, m), 2.58 (1H, m), 2.13 (1H, m), 1.91 (1H, m), 1.51 (3H, m), 1.31 (1H, m), 0.81 (3H, t).

EXAMPLE 13

2-[[[1S-[1α,3β,4α(1S*,2R*)]]-3-Hydroxy-4-[7-[(2-phenylcyclopropyl)amino]-5-(propylthio)-3H-1,2,3-triazolo[4,5-d]pyrimidin-3-yl]-cyclopentyl]oxy]acetic acid, hemiammonium salt a) 2-[[[1S-[1α,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-2-cyclopentenyl]oxy]acetic acid, 1,1-dimethylethyl ester To a solution of the product from example 1 step (e) (1.20 g) in toluene (10 ml) was added aqueous NaOH (5N, 10 ml) followed by tetrabutylammonium bromide (0.10 g) and the mixture stirred for 30 minutes. Dimethyl sulfoxide (670 μl) and tert-butyl bromoacetate (3.47 ml) were added and the reaction mixture stirred for 1 hour. The organic phase was washed with water and brine, dried and evaporated. The residue was purified (SiO$_2$, ethyl acetate:hexane 15:85 to 3:7 as eluant) to afford the subtitle compound (0.96 g).

MS (APCI) 673 (M+H$^+$,100%)

b) 2-[[[1S-[1α,3β,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-3-hydroxy-cyclopentyl]oxy]acetic acid, 1,1-dimethylethyl ester and 2-[[[1S-[1α,2β,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-2-hydroxy-cyclopentyl]oxy]acetic acid, 1,1-dimethylethyl ester A solution of the product from step (a) (1.08 g) in tetrahydrofuran (15 ml) at 0° C. was treated with borane-tetrahydrofuran complex (1M solution in tetrahydrofuran, 8.02 ml) dropwise. The reaction mixture was stirred at 0° C. for 16 hours. Methanol was added and the mixture was stirred at room temperature and then concentrated. The residue was dissolved in diglyme (10 ml) then treated with trimethylamine-N-oxide (0.48 g). The reaction mixture was heated at 130° C. for 2 hours then diluted with ethyl acetate and washed with brine, 1N HCl and aqueous sodium bicarbonate, dried and concentrated. Purification (SiO$_2$, ethyl acetate:hexane 3:7 as eluant) gave the two products:

(i) 2-[[[1S-[1α,3β,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-3-hydroxy-cyclopentyl]oxy]acetic acid, 1,1-dimethylethyl ester (0.33 g)

NMR δH (d$_6$-DMSO) 7.27–7.11 (5H, m), 6.98 (1H, d), 6.54 (1H, d), 6.39 (1H, m), 5.23 (2H, br m), 5.03 (1H, d), 4.80 (3H, m), 4.20 (1H, m), 3.95 (2H, s), 3.71 (3H, s), 3.66 (3H, s), 3.00–2.90 (3H, m), 2.65 (1H, m), 2.38 (1H, br m), 2.30–2.10 (2H, m), 1.95 (1H, m), 1.60 (2H, sextuplet), 1.45 (1H, m), 1.43 (9H, s), 0.90 (3H, t).

(ii) 2-[[[1S-[1α,2β,4α(1S*,2R*)]]-4-[7-[N-[(2,4-Dimethoxyphenyl)methyl]-(2-phenylcyclopropyl)amino]-5-(propylthio)-3H-1,2,3-triazolo[4,5-d]pyrimidin-3-yl]-2-hydroxy-cyclopentyl]oxy]acetic acid, 1,1-dimethylethyl ester (0.21 g)

NMR δH (d$_6$-DMSO) 7.27–7.11 (5H, m), 6.98 (1H, d), 6.54 (1H, d), 6.40–6.36 (1H, m), 5.27 (2H, m), 4.89 (1H, d), 4.25 (1H, m), 4.04 (2H, s), 3.88 (1H, m), 3.71 (3H, s), 3.65 (3H, s), 3.00–2.90 (3H, m), 2.67 (1H, m), 2.37 (1H, m), 2.30–2.10 (2H, m), 1.61 (2H, sextuplet), 1.44 (1H, m), 1.43 (9H, s), 0.91 (3H, t).

c) 2-[[[1S-1α,3β,4α(1S*,2R*)]]-3-Hydroxy-4-[7-[(2-phenylcyclopropyl)amino]-5-(propylthio)-3H-1,2,3-triazolo[4,5-d]pyrimidin-3-yl]-cyclopentyl]oxy] acetic acid, hemiammonium salt The title compound was prepared according to the method of example 2, step (b) using the product of step (b)(i).

MS (APCI) 485 (M+H$^+$,100%)

NMR δH (d$_6$-DMSO) 7.31–7.15 (5H, m), 4.78–4.68 (2H, m), 4.17 (1H, m), 3.90 (2H, s), 3.20 (1H, m), 2.97–2.81 (2H, m), 2.65–2.52 (1H, m), 2.25–2.11 (3H, m), 1.92–1.85 (1H, m), 1.55–1.45 (3H, m), 1.34 (1H, m), 0.81 (3H, t).

EXAMPLE 14

2-[[[1S-[1α,2β,4α(1S*,2R*)]]-2-Hydroxy-4-[7-[(2-phenylcyclopropyl)amino]-5-(propylthio)-3H-1,2,3-triazolo[4,5-d]pyrimidin-3-yl]-cyclopentyl]oxy] acetic acid, hemiammonium salt The title compound was prepared according to the method of example 2 step (b) using the product of step (b)(ii).

MS (APCI) 485 (M+H$^+$,100%)

NMR δH (d$_6$-DMSO) 7.31–7.16 (5H, m), 5.21 (1H, quintet), 4.28 (1H, m), 4.03–3.92 (2H, m), 3.82 (1H, m), 3.19 (1H, m), 2.96–2.83 (2H, m), 2.64 (1H, m), 2.41 (1H, m), 2.16–2.08 (3H, m), 1.54–1.47 (3H, m), 1.33 (1H, m), 0.82 (3H, t).

EXAMPLE 15

2-[[[1S-(1α,2β,3β,4α)]-4-[7-(Butylamino)-5-(propylthio)-3H-1,2,3-triazolo[4,5-d]pyrimidin-3-yl]-2,3-dihydroxy-cyclopentyl]oxy]acetic acid a) 5,7-Bis(propylthio)-1H-1,2,3-triazolo[4,5-d]pyrimidine A mixture of 4,5-diamino-2,6-dimercaptopyrimidine (25 g), potassium hydroxide (36.9 g) and propyl iodide (62.9 ml)

in water (710 ml) was stirred for 72 hours. The product was collected by filtration, washed with water and dried. The material was taken into water (710 ml)/glacial acetic acid (710 ml), cooled to 5° C. and a solution of sodium nitrite (9.38 g) in water (109 ml) added, maintaining the temperature below 5° C. The mixture was allowed to reach room temperature and the product was collected by filtration, washed with water and dried (28.9 g).

MS (EI) 269 (M+)

b) Mixture of (1S-cis)-4-[5,7-bis(propylthio)-3H-1,2,3-triazolo[4,5-d]pyrimidin-3-yl]-2-cyclopentene-1-ol and (1S-cis)-4-[5,7-bis(propylthio)-2H-1,2,3-triazolo[4,5-d]pyrimidin-2-yl]-2-cyclopentene-1-ol To a solution of the product from step (a) (3.7 g), (1S-cis)-4-acetoxy-2-cyclopenten-1-ol (2.0 g) and triethylamine (6 ml) in THF (100 ml) at 60° C. was added tetrakis(triphenylphosphine)palladium (0) (2.0 g), as a suspension in THF (50 ml). The reaction mixture was stirred at 60° C. for 4.5 hours and purified ($SiO_2$, ethyl acetate:hexane 1:3 as eluant) to give the product as a 2:1 isomeric mixture.

MS (APCI) 352 (M+H+,100%)

c) [3aR-(3aα,4α,6α,6aα)]-6-[5,7-Bis(propylthio)-3H-1,2,3-triazolo[4,5-d]pyrimidin-3-yl]-tetrahydro-2,2-dimethyl-4H-cyclopenta-1,3-dioxol-4-ol A mixture of the product from step (b) (2.0 g), 4-methylmorpholine-N-oxide (1.27 g) and osmium tetroxide (2.5% solution in tert-butanol, 2.9 ml) in acetone (110 ml) and water (25 ml) was stirred at room temperature for 16 hours. Sodium hydrosulfite (2.0 g) was added and the mixture was stirred for 1 hour then filtered through celite, washing with ethyl acetate. The combined filtrates were concentrated and the residue dissolved in acetone (75 ml). Tosic acid (1.08 g) and 1,1-dimethoxypropane (6 ml) were added and the mixture was stirred for 1 hour. The solution was concentrated and the residue was partitioned between dichloromethane and water. The organic phase was dried and concentrated and the residue purified ($SiO_2$, ethyl acetate:hexane 1:4 as eluant) to give the subtitle compound (1.08 g).

MS (APCI) 426 (M+H+,100%)

d) 2-[[[3aR-(3aα,4α,6α,6aα)]-6-[5,7-Bis(propylthio)-3H-1,2,3-triazolo[4,5-d]pyrimidin-3-yl]-tetrahydro-2,2-dimethyl-4H-cyclopenta-1,3-dioxol-4-yl]oxy]acetic acid, 1,1-dimethylethyl ester To a solution of the product from step (c) (0.36 g) in THF (10 ml) at 0° C. was added sodium hydride (60% in oil, 37 mg). The mixture was stirred at 0° C. for 15 minutes and tert-butyl bromoacetate (0.14 ml) was added. The mixture was stirred at room temperature for 24 hours and purified ($SiO_2$, ethyl acetate:hexane 1:10 as eluant) to give the subtitle compound (0.16 g).

MS (APCI) 482 (M+H+,100%)

e) 2-[[[3aR-(3aα,4α,6α,6aα)]-6-[7-(Butylamino)-5-(propylthio)-3H-1,2,3-triazolo[4,5-d]pyrimidin-3-yl]-tetrahydro-2,2-dimethyl-4H-cyclopenta-1,3-dioxol-4-yl]oxy]acetic acid, 1,1-dimethylethyl ester A mixture of the product from step (d) (0.15 g) and n-butylamine (5 ml) in 1,4-dioxane (10 ml) was stirred at room temperature for 1 hour, concentrated and purified ($SiO_2$, ethyl acetate:hexane 1:5 as eluant) to give the subtitle compound (0.14 g).

MS (APCI) 537 (M+H+,100%)

f) 2-[[[1S-(1α,2β,3β,4α)]-4-[7-(Butylamino)-5-(propylthio)-3H-1,2,3-triazolo[4,5-d]pyrimidin-3-yl]-2,3-dihydroxy-cyclopentyl]oxy]acetic acid The product was prepared according to the method of example 2, step (b) using the product of step (e).

MS (ESI) 441 (M+H+, 100%)

NMR δH ($d_6$-DMSO) 9.01 (1H, t), 4.94 (1H, q), 4.53 (1H, m), 4.04 (2H, m) 4.00 (1H, m), 3.85 (1H, m), 3.50 (2H, q), 3.08 (2H, m), 2.64 (1H, m), 2.08 (1H, m), 1.65 (4H, m), 1.34 (2H, m), 0.99 (3H, t), 0.91 (3H, t).

EXAMPLE 16

2-[[[1S-(1α,2β,3β,4α)]-4-[7-(Butylamino)-5-(propylthio)-3H-1,2,3-triazolo[4,5-d]pyrimidin-3-yl]-2,3-dihydroxycyclopentyl]oxy]acetamide To a solution of the product of example 15 (0.21 g) in N,N-dimethylformamide (25 ml) was added a solution of ammonia in acetonitrile (5 ml) and bromo-tris-pyrrolidino-phosphonium hexafluorophosphate (0.35 g). The mixture was stirred for 10 minutes and N,N-diisopropylethylamine (300 μl) was added. The reaction mixture was stirred at room temperature for 2 hours, concentrated and purified (Sep-pak® C18 silica, water to acetonitrile gradient elution followed by HPLC, Nova-pak® C18 column, 0.1% aqueous trifluoroacetic acid:acetonitrile 50:50) to give the title compound (0.09 g).

MS (APCI) 440 (M+H+,100%)

NMR δH ($d_6$-DMSO) 8.99 (1H, t), 7.33 (1H, br s), 7.18 (1H, br s), 5.20–5.10 (2H, br s), 4.95 (1H, q), 4.57–4.53 (1H, m), 4.04–4.02 (1H, m), 3.88 (2H, s), 3.81–3.79 (1H, m), 3.49 (2H, q), 3.11–3.06 (2H, m), 2.70–2.60 and 2.15–2.01 (1H, m), 1.70 (2H, sextet), 1.63 (2H, quintet), 1.34 (2H, sextet), 0.99 (3H, t), 0.91 (3H, t).

EXAMPLE 17

[1S-[1α,2β,3β,4α(1S*,2R*)]]-4-[[5-(Methylthio)-7-[(2-phenylcyclopropyl)amino]-3H-1,2,3-triazolo[4,5d]pyrimidin-3-yl]-cyclopentane-1,2,3-triol a) [1S-[1α,2β,3β,4α(1S*,2R*)]]-4-[7-[(2-Phenylcyclopropyl)amino]-5-(propylsulphonyl)-3H-1,2,3-triazolo[4,5-d]pyrimidin-3-yl]-cyclopentane-1,2,3-triol Prepared according to the method of example 4, step (a) using the product of example 12.

MS (APCI) 475 (M+H+, 100%)

b) [1S-[1α,2β,3β,4α(1S*,2R*)]]-4-[[5-(Methylthio)-7-[(2-phenylcyclopropyl)amino]-3H-1,2,3-triazolo[4,5-d]pyrimidin-3-yl]-cyclopentane-1,2,3-triol Sodium thiomethoxide (0.11 g) was added to a solution of the product of step a) (0.34 g) in THF (20 ml) and the reaction stirred for 1 hour. The reaction mixture was concentrated and the residue purified ($SiO_2$, ethyl acetate as eluant) to give the title compound (0.20 g).

MS (APCI) 415 (M+H+,100%)

NMR δH ($d_6$-DMSO) 9.36 (1H, d), 7.31–7.16 (5H, m), 5.11–5.10 (1H, m), 5.04–5.01 (1H, m), 4.97 (1H, d), 4.94–4.93 (1H, m), 4.68–4.63 (1H, m), 3.94–3.92 (1H, m), 3.79 (1H, s), 3.21–3.18 (1H, m), 2.62–2.57 (1H, m), 2.32

(3H, s), 2.15–2.11 (1H, m), 2.14–2.10 (2H, m), 1.94–1.87 (1H, m), 1.51–1.47 (1H, m), 1.36–1.32 (1H, m)

EXAMPLE 18

[1S-[1α,2β,3β,4α(1S*,2R*)]]-4-[5-[(Methylethyl)thio]-7-[(2-phenylcyclopropyl)amino]-3H-1,2,3-triazolo[4,5-d]pyrimidin-3-yl]-cyclopentane-1,2,3-triol Prepared according to the method of example 4, step (b) using the product of example 17, step (a).

MS (APCI) 443 (M+H$^+$,100%)

NMR δH (d$_6$-DMSO) 9.38 (1H, d), 7.31–7.16 (5H, m), 5.11 (1H, d), 5.04–4.96 (1H, m), 4.93–4.91 (1H, m), 4.67–4.63 (1H, m), 3.94–3.92 (1H, m), 3.79 (1H, s), 3.61 (1H, sept) 3.20–3.16 (1H, m), 2.62–2.57 (1H, m), 2.11–2.07 (1H, m), 1.93–1.89 (1H, m), 1.60–1.54 (1H, m), 1.38–1.30 (1H, m), 1.13 (3H, d), 1.07 (3H, d)

EXAMPLE 19

[1S-1α,2β,3β,4α(1S*,2R*)]]-4-[7-[[2-(4-Fluorophenyl)cyclopropyl]amino]-5-(propylthio)-3H-1,2,3-triazolo[4,5-d]pyrimidin-3-yl]-cyclopentane-1,2,3-triol a) (1R-cis)-Bis(1,1-dimethylethyl)-4-hydroxy-2-cyclopentenylimidodicarbonate To a suspension of ether washed sodium hydride (60% dispersion in oil; 0.31 g) in THF (30 ml) was added imidodicarbonic acid bis-(1,1-dimethylethyl)ester (1.84 g). The mixture was stirred at 40° C. for 1 hour. To the mixture, at ambient temperature, was then added (1S-cis)-4-acetoxy-2-cyclopenten-1-ol (0.5 g) and tetrakis(triphenylphosphine)palladium (0) (0.185 g). The reaction mixture was stirred for 24 hours then purified (SiO$_2$, ethyl acetate:hexane 1:9 as eluant) to give the subtitle compound as a colourless solid (0.9 g).

NMR δH (d$_6$-DMSO) 1.43 (18H, s), 1.61 (1H, ddd, J=12.3, 7.7, 6.4 Hz), 2.54 (1H, dt, J=12.6, 7.4 Hz), 4.51–4.57 (1H, m), 4.86 (1H, tq, J=8.0, 1.8 Hz), 4.91 (1H, d, J=5.4 Hz), 5.71–5.77 (2H, m).

b) [1R-(1α,2β,3β,4α)]-2,3,4-Trihydroxy-cyclopentenylimidodicarbonic acid, bis(1,1-dimethylethyl) ester The subtitle compound was prepared according to the method of example 12, step (f) using the product of step (a).

NMR δH (d$_6$-DMSO) 1.44 (18H, s), 1.46–1.60 (1H, m), 1.97–2.05 (1H, m), 3.55–3.58 (1H, m), 3.66–3.73 (1H, m), 4.11–4.21 (2H, m), 4.54 (1H, d, J=4.8 Hz), 4.56 (1H, d, J=5.9 Hz), 4.82 (1H, d, J=4.6 Hz)

c) [1S-(1α,2β,3β,4α)]-4-[[6-Chloro-5-nitro-2-(propylthio)-pyrimidin-4-yl]amino]-2-cyclopentane-1,2,3-triol A mixture of the product of step (b) (0.68 g), methanol (10 ml) and hydrochloric acid (2M; 5 ml) was stirred for 24 hours then concentrated under reduced pressure. To the residue was added THF (10 ml) and N,N-diisopropylethylamine (1.78 ml) followed by 4,6-dichloro-5-nitro-2-(propylthio)pyrimidine (prepared as described in WO 9703084) (0.82 g). The mixture was heated at reflux for 20 hours then cooled and concentrated under reduced pressure. The residue was purified (SiO$_2$, ethyl acetate:hexane 7:3 as eluant) to give the subtitle compound as a yellow solid (0.47 g).

MS (APCI) 365/367 (M+H$^+$,100%)

d) [1S-(1α,2β,3β,4α)]-4-[[5-Amino-6-chloro-2-(propylthio)-pyrimidin-4-yl]amino]-2-cyclopentane-1,2,3-triol The subtitle compound was prepared according to the method of example 12, step (b) using the product of step (c).

MS (APCI) 335/337 (M+H$^+$,100%)

e) [1S-(1α,2β,3β,4α)]-4-[7-Chloro-5-(propylthio)-3H-1,2,3-triazolo[4,5-d]pyrimidin-3-yl]-cyclopentane-1,2,3-triol The subtitle compound was prepared according to the method of example 12, step (c) using the product of step (d).

MS (APCI) 346/348 (M+H$^+$), 318 (100%)

f) [3aS-[1(E),3aα,6α,7aβ]]-1-[3-(4-Fluorophenyl)-1-oxo-2-propenyl]-hexahydro-8,8-dimethyl-3H-3a,6-methano-2,1-benzisothiazole-2,2-dioxide A mixture of 3-(4-fluorophenyl)-2-propenoic acid (3.0 g) and thionyl chloride (5.0 ml) was stirred at 70° C. for 1 hour, the reaction mixture was then concentrated under reduced pressure. The residue was azeotroped twice with dichloromethane then dissolved in toluene (10 ml). To a suspension of sodium hydride (60% dispersion in oil; 0.99 g) in toluene (40 ml) was added a solution of [3aS-(3aα,6α,7aβ)]-hexahydro-8,8-dimethyl-3H-3a,6-methano-2,1-benzisothiazole-2,2-dioxide (3.89 g) in toluene (40 ml) and the mixture stirred for 30 minutes. To the reaction mixture was then added the solution described above and the resulting suspension was stirred for 16 hours. Water (200 ml) was added, the organics collected and the aqueous extracted into dichloromethane (3×100 ml). The organics were combined, dried and concentrated. Recrystallisation (ethanol) gave the subtitle compound as colourless needles (5.92 g).

MS (APCI) 364 (M+H$^+$,100%)

g) [3aS-[1(1S*,2S*),3aa,6a,7ab]]-1-[[2-(4-Fluorophenyl)cyclopropyl]carbonyl]-hexahydro-8,8-dimethyl-3H-3a,6-methano-2,1-benzisothiazole-2,2-dioxide A solution of diazomethane (2.9 g) in ether (150 ml) (prepared as descibed in Vogel's textbook of practical organic chemistry, fifth edition, Longman scientific and technical, p432) was added to a solution of the product of step f) (5.90 g) and palladium(II) acetate (18 mg) in dichloromethane (350 ml) at 0° C. and the reaction mixture stirred at 0° C. for 5 hours. Acetic acid (5 ml) was added and the reaction mixture was then washed with saturated sodium bicarbonate solution (200 ml) and the organics filtered through a plug of silica. After concentrating in vacuo, the residue was recrystallised (ethanol) to give the subtitle compound as colourless needles (3.81 g).

MS (APCI) 378 (M+H$^+$,100%)

h) (1R-trans)-2-(4-Fluorophenyl)-cyclopropanecarboxylic acid

A suspension of the product from step g) (3.74 g) and lithium hydroxide monohydrate (4.11 g) in tetrahydrofuran (100 ml) and water (3 ml) was stirred at 50° C. for 24 hours. The reaction mixture was concentrated in vacuo, and the residue dissolved in water (100 ml), acidified with 2N HCl and extracted into dichloromethane (3×75 ml). The organics were dried and concentrated. Purification (SiO$_2$, isohexane:diethylether 2:1 as eluant) gave the subtitle compound as a colourless solid (1.78 g).

MS (APCI) 179 (M–H+,100%)

i) (1R-trans)-2-(4-Fluorophenyl)cyclopropanamine

To a solution of the product from step h) (2.6 g) and triethylamine (2.7 ml) in acetone/water (10:1, 33 ml) at 0° C. was added ethyl chloroformate (2.0 ml) over 5 min. The solution was maintained at 0° C. for 0.5 h before addition of sodium azide (1.52 g) in water (6 ml). After a further hour, water (350 ml) was added and the reaction mixture extracted with toluene (3×100 ml). The organic extracts were combined and dried, then heated at reflux for 2 hours behind a blast screen. After cooling the solution, 6N HCl (50 ml) was added and the mixture heated at reflux for 3 hours. Water (150 ml) was added and the aqueous phase basified with 2N NaOH (aq), then extracted into dichloromethane (3×100 ml). The organic phase was dried and concentrated to give the subtitle compound as a colourless oil (1.31 g).

NMR δH (CDCl$_3$) 0.88–0.95 (1H, m), 0.99–1.06 (1H, m), 1.81–1.87 (1H, m), 2.47–2.52 (1H,m), 6.90–7.00 (4H, m)

j) [1S-(1α,2β,3β,4α(1S*,2R*)]]-4-[7-[[2-(4-Fluorophenyl)cyclopropyl]amino]-5-(propylthio)-3H-1,2,3-triazolo[4,5-d]pyrimidin-3-yl] cyclopentane-1,2,3-triol The title compound was prepared according to the method of example 12, step (e) using the products of step (e) and step (i).

MS (APCI) 461 (M+H+, 100%)

NMR δH (d$_6$-DMSO) 0.99 (3H, t, J=7.2 Hz), 1.29–2.15 (6H, m), 2.55–2.63 (1H, m), 2.81–3.15 (2H, m), 3.14–3.33 (1H, m), 3.78 (1H, br s), 3.93 (1H, br s), 4.66 (1H, br s), 4.92–5.12 (4H, m), 7.11–7.26 (4H, m), 9.33 (1H, d, J=4.2 Hz)

EXAMPLE 20

[1S-[1α,2β,3β,4α(1S*,2R*)]]-4-[7-[[2-(4-Methoxyphenyl)cyclopropyl]amino]-5-(propylthio)-3H-1,2,3-triazolo[4,5-d]pyrimidin-3-yl] cyclopentane-1,2,3-triol a) [1R-(trans)]-2-(4-Methoxyphenyl)cyclopropane carboxylic acid

To a solution of dichloro(p-cymene)ruthenium (II) dimer (250 mg) and 2,6-bis[(4S)isopropyl-2-oxazolin-2-yl] pyridine (240 mg) in dichloromethane (150 ml) at room temperature was added 4-vinylanisole (25 g). To this solution was added ethyl diazoacetate (5.0 g) over 6 hr. The solution was maintained at room temperature for 18 hours then diluted with i-hexane (200 ml) and passed through a plug of silica (50 g) with a further 250 ml of 1:1 i-hexane/dichloromethane. The filtrate was concentrated and the residue dissolved in methanol (100 ml) and LiOH (4 g) in water (10 ml) added, the mixture was then refluxed for 4h. The resulting solution was concentrated to give a colourless solid which was washed with 1:1 ether/i-hexane (100 ml). The solid was then triturated with 2N HCl and the precipitate collected to give the subtitle compound (5.06 g).

MS (APCI) 191 (M–H+, 100%)

b) [1R-(trans)]-2-(4-Methoxyphenyl) cyclopropanamine, [(R-(R*,R*)]-2,3-dihydroxybutanedioate (1:1)

The amine was prepared according to the method of example 19, step i) using the product of step a). The amine was dissolved in ethanol (5 ml) and a solution of L-tartartic acid (0.75 g) in ethanol (5 ml) was added. After 20 minutes the solid was collected and recrystallised (isopropanol/water 3:1) affording the subtitle compound as colourless needles. M.p. 192–3° C.

NMR δH (d$_6$-DMSO) 7.05 (2H, d), 6.85 (2H, d), 3.91 (2H, s), 3.71 (3H, s), 2.70–2.60 (1H, m), 2.15–2.07 (1H, m) 1.22–1.08 (1H, m), 1.03 (1H, dd)

c) [1S-[1α,2β,3β,4α(1S*,2R*)]]-4-[7-[[2-(4-Methoxyphenyl)cyclopropyl]amino]-5-(propylthio)-3H-1,2,3-triazolo[4,5-d]pyrimidin-3-yl]-cyclopentane-1,2,3-triol The title compound was prepared according to the method of example 12, step (e) using the products of step (b) and the product of example 19, step (e).

MS (APCI) 473 (M+H+, 100%)

NMR δH (d$_6$-DMSO) 0.83 (3H, t, J=7.2 Hz), 1.20–2.25 (6H, m), 2.50–2.60 (1H, m), 2.81–3.04 (2H, m), 3.06–3.17 (1H, m), 3.33 (3H, s), 3.73 (1H, br s), 3.91–3.98 (1H, m), 4.60–4.70 (1H, m), 4.90–5.13 (4H, m), 6.86 (2H, d, J=8.7 Hz), 7.14 (2H, d, J=8.7 Hz), 9.30 (1H, d, J=4.2 Hz)

EXAMPLE 21

[1S-[1α,2β,3β,4α(1S*,2R*)]]-4-[7-[[2-(4-Methylphenyl) cyclopropyl]amino]-5-(propylthio)-3H-1,2,3-triazolo[4,5-d] pyrimidin-3-yl]-cyclopentane-1,2,3-triol a) (1R-trans)-2-(4-Methylphenyl)cyclopropane carboxylic acid

Prepared according to the method of Example 20, step a) using 4-methyl-1-ethenyl-benzene.

MS (APCI) 175 (M–H+, 100%)

b) (1R-trans)-2-(4-Methylphenyl)cyclopropanamine, [R-(R*,R*)]-2,3-dihydroxybutanedioate (1:1)

Prepared according to the method of Example 20, step b) using the product of step a).

NMR δH (d$_6$-DMSO)7.08 (2H, d), 7.00 (2H, d), 3.98 (2H, s), 2.75–65 (1H, m), 2.50 (3H, s), 2.30–2.20 (1H, m) 1.30–1.22 (1H, m), 1.09 (1H, dd)

c) [1S-[1α,2β,3β,4α(1S*,2R*)]]-4-[7-[[2-(4-Methylphenyl)cyclopropyl]amino]-5-(propylthio)-3H-1,2,3-triazolo[4,5-d]pyrimidin-3-yl]-cyclopentane-1,2,3-triol The title compound was prepared according to the method of example 1, step (a), using the products of step (b) and example 19, step (e).

MS (APCI) 457 (M+H+, 100%)

NMR δH (d$_6$-DMSO) 0.99 (3H, t, J=7.2 Hz), 1.30–1.40 (1H, m), 1.45–1.40 (1H, m), 1.50 and 1.70 (2H, sex, J=7.2 Hz), 1.87–1.94 (1H, m), 2.07–2.12 (1H, m), 2.27 (3H, s) 2.54–2.61 (1H, m), 2.83–2.99 (2H, m), 3.15–3.17 (1H, m), 3.78 (1H, br s), 3.93 (1H, br s), 4.66–4.67 (1H, m), 4.91–5.11 (4H, m), 7.09 (4H, br s), 9.35 (1H, br s)

EXAMPLE 22

[1S-[1α,2β,3β,4α(1S*,2R*)]]-4-[7-[[2-(4-Chlorophenyl)cyclopropyl]amino]-5-(propylthio)-3H-1,2,3-triazolo[4,5-d]pyrimidin-3-yl]-cyclopentane-1,2,3-triol a) [1R-[1α(S*),2β]]-N-[2-4Chlorophenyl) cyclopropyl]-2-methoxy-2-phenyl-acetamide and [1S-[1α(R*),2β]]-N-[2-(4-Chlorophenyl) cyclopropyl]-2-methoxy-2-phenyl-acetamide Oxalyl chloride (4.00 ml) was added to a solution of (S)-α-methoxyphenylacetic acid (2.00 g) in dichloromethane (100 ml)/DMF (10 ml). The reaction mixture was stirred at room temperature for 4 hours then concentrated and the residue azeotroped with dichloromethane (3×10 ml). The resulting oil was taken into dichloromethane (4 ml) and treated with a solution of 2-(4-chlorophenyl) cyclopropylamine (Prepared as described by C Kaiser etal J. Med. Pharm. Bul., 1962, 5, 1243) (1.86 g) in pyridine (8 ml). The reaction mixture was stirred at room temperature for 30 minutes then partitioned between dichloromethane (500 ml) and water (500 ml). The organic phase was dried and concentrated and the residue purified (SiO$_2$, isohexane:ethyl acetate:acetic acid 66:33:1) to afford [1S-[1α(R*),2β]]-N-[2-(4-Chlorophenyl)cyclopropyl]-2-methoxy-2-phenyl-acetamide (1.23 g)

MS (APCI, negative ionization) 314 (M–H$^+$, 100%)

Further elution of the column gave [1R-[1α(S*),2β]]-N-[2-(4-Chlorophenyl)cyclopropyl]-2-methoxy-2-phenyl-acetamide (1.40 g).

MS (APCI, negative ionization) 314 (M–H$^+$, 100%).

b) (1R-trans)-2-(4-Chlorophenyl)-cyclopropanamine

A solution of [1R-[1α(S*),2β]]-N-[2-(4-Chlorophenyl) cyclopropyl]-2-methoxy-2-phenyl-acetamide (1.10 g) (prepared as described in step (a)) in 1,4-dioxane (20 ml) containing 5M HCl (aq) (40 ml) was heated at reflux for 18 hours. The reaction was concentrated and the residue partitioned between water and diethyl ether. The aqueous phase was treated with 2M aqueous sodium hydroxide solution (100 ml) then extracted with diethyl ether (2×100 ml). The organic phase was concentrated to afford the subtitle compound (0.55 g). Optical rotation –138.3° (c=0.2, methanol).

c) [1S-[1α,2β,3β,4α(1S*,2R*)]]-4-[7-[[2-(4-Chlorophenyl)cyclopropyl]amino]-5-(propylthio)-3H-1,2,3-triazolo[4,5-d]pyrimidin-3-yl]-cyclopentane-1,2,3-triol The title compound was prepared according to the method of example 12, step (e), using the products of step (b) and example 19, step (e).

MS (APCI) 477/479 (M+H$^+$, 100%)

NMR δH (d$_6$-DMSO) 0.99 (3H, t, J=7.2 Hz), 1.30–1.40 (1H, m), 1.48 and 1.68 (2H, sex, J=7.2 Hz), 1.52–1.60 (1H, m), 1.87–1.94 (1H, m), 2.10–2.15 (1H, m), 2.50–2.60 (1H, m), 2.76–3.15 (2H, m), 3.13–3.21 (1H, m), 3.73 (1H, br s), 3.93 (1H, br s), 4.60–4.68 (1H, m), 4.89–5.11 (4H, m), 7.22 (2H, d, J=8.4 Hz), 7.33 (2H, d, J=8.4 Hz), 9.35 (1H, br s)

EXAMPLE 23

2-[[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl] oxy]-acetamide a) [3aR-[3aα,4α,6α(1R*,2S*),6aα)]]-6-[7-[N-[2,4-Dimethoxyphenyl)methyl-(2-phenylcyclopropyl) amino]-5-(propylthio)-3H-1,2,3-triazolo[4,5-d] pyrimidin-3-yl]-tetrahydro-2,2-dimethyl-4H-cyclopenta-1,3-dioxol-4-ol To a solution of product of example 12, step (f) (4.50 g) in acetone (100 ml), 2,2-dimethoxypropane (12.60 ml) and p-toluenesulphonic acid (2.34 g) were added and the reaction mixture stirred for 1 hour. Purification (SiO$_2$, ethyl acetate:isohexane 2:7 as eluant) afforded the subtitle compound (4.34 g).

MS (APCI) 633 (M+H$^+$,100%)

b) 2-[[[3aR-[3α,4α,6α,6aα(1R*,2S*)]]-6-[7-[N-(2, 4-Dimethoxyphenyl)methyl-(2-phenylcyclopropyl)-amino]-5-(propylthio)-3H-1,2,3-triazolo[4,5-d] pyrimidin-3-yl]-tetrahydro-2,2-dimethyl-4H-cyclopenta-1,3-dioxol-4-yl]oxy]-acetic acid, 1,1-dimethylethyl ester To a solution of product of step (a) (0.40 g) in toluene (3.00 ml) were added 5M NaOH (3.00 ml) and tetrabutylammonium bromide (31 mg). The reaction mixture was stirred for 30 minutes, then dimethylsulphoxide (0.18 ml) and 1,1-dimethylethyl-2-bromoacetate were added and stirring continued for 4 hours. The toluene layer was separated and concentrated. Purification (SiO$_2$, ethyl acetate:isohexane 1:3 as eluant) afforded the subtitle compound (0.41 g).

MS (APCI) 747 (M+H$^+$,100%)

c) 2-[[1S-[1α,2β,3β,4α(1S*,2R*)]]-2,3-Dihydroxy-4-[6-[7-(2-phenylcyclopropyl)amino]-5-(propylthio)-3H-1,2,3-triazolo[4,5-d]pyrimidin-3-yl-cyclopent-1-yl]oxy]acetic acid The subtitle compound was prepared according to the method of example 2, step (b).

MS (APCI) 501 (M+H$^+$,100%)

d) 2-[[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl] oxy]-acetamide Prepared according to the method of example 16 using the product of step (c). Purification (HPLC, Novapak® C18 column, 0.1% aqueous ammonium acetate:acetonitrile, 63:37) afforded the tide compound (0.04 g).

MS (APCI) 501 (M+H$^+$,100%)

NMR δH (d$_6$-DMSO) 9.35 (1H, d), 7.33–7.16 (7H, m), 5.20 (2H, br m), 5.00–4.90 (1H, q), 4.55 (1H, m), 4.05 (1H, br s), 3.85 (2H, s), 3.80 (1H, m), 3.20 (1H, br m), 3.15 (1H, m), 3.00–2.90 (1H, m), 1.91 (1H, m), 1.51 (3H, m), 1.31 (1H, m), 0.81 (3H, t).

EXAMPLE 24

[1S-[1α,2β,3β,4α(1S*,2R*)]]-4-[7-[[2-(3-Methoxyphenyl)cyclopropyl]amino]-5-(propylthio)-3H-1,2,3-triazolo[4,5-d]pyrimidin-3-yl]-cyclopentane-1,2,3-triol a) [3aR-(3aa,4a,6a,6aa)]-6-Amino-tetrahydro-2,2-dimethyl-4H-cyclopenta-1,3-dioxol-4-ol, hydrochloride The product from example 19, step (b) (17.37 g) in 6M HCl (100 ml) and methanol (500 ml) was stirred for 18 hours. The mixture was evaporated and then azeotroped with toluene (4×200 ml) to give a colourless powder (8.67 g). This solid was suspended in acetone (250 ml) containing 2,2-dimethoxypropane (25 ml) and conc. HCl (0.2 ml) then heated under reflux for 2 hours. The mixture was cooled, evaporated and azeotroped with toluene (3×200 ml). The residue was dissolved in 20% aqueous acetic acid and stirred for 2 hours. The mixture was evaporated and azeotroped with toluene (4×200 ml) to afford the subtitle compound (10.1 g).

MS (APCI) 174 (M+H$^+$, 100%)

b) [3aR-(3aa,4a,6a,6aa)]-6-[[6-Chloro-5-nitro-2-(propylthio)-pyrimidin-4-yl]amino]-tetrahydro-2,2-dimethyl-4H-cyclopenta-1,3-dioxol-4-ol A solution of the product from step (a) (10.0 g) and N,N-diisopropylethylamine (35 ml) in THF (600 ml) was stirred for 1 hour. The mixture was filtered and the solution was added over 1 hour to a solution of 4,6-dichloro-5-nitro-2-(propylthio)-pyrimidine (prepared as described in WO 9703084) (25.57 g) in THF (1000 ml) and stirred for a further 2 hour. The solvent volume was reduced in vacuo and ethyl acetate was added (1000 ml). The mixture was washed with water and the organic layers were dried (MgSO$_4$), evaporated and purified (SiO$_2$, isohexane-ethyl acetate as eluant) to afford the sub-title compound (14.22 g).

MS (APCI) 405 (M+H$^+$, 100%)

c) [3aR-(3aα,4a,6a,6aa)]-6-[[5-Amino-6-chloro-2-propylthiopyrimidin-4-yl]amino]-tetrahydro-2,2-dimethyl-4H-cyclopenta-1,3-dioxol-4-ol The subtitle compound was prepared according to the method of example 12, step (b) using the product of step (b).

MS (APCI) 375 (M+H$^+$, 100%)

d) [3aR-(3aα,4a,6a,6aa)]-6-[7-Chloro-5-(propylthio)-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of example 12, step (c) using the product of step (c).

MS (APCI) 386 (M+H$^+$, 100%)

e) (1R-trans)-2-(3-Methoxyphenyl) cyclopropanamine hydrochloride

The subtitle compound was prepared according to the method of example 19, step (i) using (1R-trans)-2-(3-methoxyphenyl)-cyclopropanecarboxylic acid(Prepared as described by Vallgaarda etal. J. Chem. Soc., Perkin Trans. 1, 1994, 461–70). The product was taken up in 2N HCl and freeze dried to afford the hydrochloride salt.

MS (APCI) 164 (M+H$^+$).

f) [1S-[1α,2β,3β,4α(1S*,2R*)]]-4-[7-[[2-(3-Methoxyphenyl)cyclopropyl]amino]-5-(propylthio)-3H-1,2,3-triazolo[4,5-d]pyrimidin-3-yl]-cyclopentane-1,2,3-triol To a suspension of the product from step (d) (0.40 g) and step (e) (0.28 g) in dichloromethane (20 ml) was added N,N-diisopropylethylamine (0.89 ml), the resulting solution was then stirred at room temperature for 7 hours. The reaction mixture was concentrated and the residue taken up in methanol (45 ml)/2N HCl (5 ml), this solution was then stirred at room temperature for 16 hours. The reaction mixture was concentrated and the residue partitioned between water (50 ml) and dichloromethane (50 ml), the organics were dried (MgSO4), filtered, and concentrated. The product was purified (HPLC, Novapak® C18 column, 0.1% aqueous ammonium acetate:acetonitrile, 50:50) to afford the title compound (0.44 g).

MS (APCI) 473 (M+H, 100%)

NMR δH (d$_6$-DMSO) 9.39 (1H, d, J=4.0 Hz), 7.23–6.81 (4H, m), 5.17–4.97 (4H, m), 4.7–4.69 (1H, m), 4.00 (1H, br s), 3.84 (1H, br s), 3.79 (3H, br s), 3.29–3.26 (1H, m), 3.06–2.87 (2H, m), 2.69–2.61 (1H, m), 2.19–2.14 (1H, m), 2.00–1.94 (1H, m), 1.76–1.51 (3H, m), 1.42–1.29 (1H, m), 0.87 and 1.05 (3H, t, J=7.6 Hz).

EXAMPLE 25

[1S-[1α,2β,3β,4α(1S*,2R*)]]-4-[7-[[2-(3-Methylphenyl)cyclopropyl]amino]-5-(propylthio)-3H-1,2,3-triazolo[4,5-d]pyrimidin-3-yl]-cyclopentane-1,2,3-triol a) (1R-trans)-2-(3-Methylphenyl)cyclopropane carboxylic acid Prepared according to the method of Example 20, step a) using 1-ethenyl-3-methyl-benzene.

MS (APCI) 175 (M–H$^+$, 100%)

b) (1R-trans)-2-(3-Methylphenyl)cyclopropanamine, [R-(R*,R*)]-2,3-dihydroxybutanedioate (1:1)

Prepared according to the method of Example 20, step b) using the product of step a).

NMR δH (d$_6$-DMSO) 7.17 (1H, t), 6.98 (1H, d), 6.93–6.89 (2H, m), 3.93 (2H, s), 2.70–2.66 (1H, m), 2.27 (3H, s), 2.13–2.08 (1H, m), 1.24–1.19 (1H, m), 1.19–1.09 (1H, m)

c) [1S-[1α,2β,3β,4α(1S*, 2R*)]]-4-[7-[[2-(3-Methylphenyl)cyclopropyl]amino]-5-(propylthio)-3H-1,2,3-triazolo[4,5-d]pyrimidin-3-yl]-cyclopentane-1,2,3-triol The title compound was prepared according to the method of example 24, step (f) using the products of step (b) and example 24, step (d).

MS (APCI) 457 (M+H$^+$, 100%)

NMR δH (d$_6$-DMSO) 9.33 (1H, s), 7.19–7.14 (1H, m), 7.04–6.96 (3H, m), 5.12–5.10 (1H, m), 5.03–4.97 (1H, m), 4.94–4.92 (1H, m), 4.92–4.90 (1H, m), 4.69–4.64 (1H, m), 3.9–3.92 (1H, m), 3.78 (1H, s), 3.20–3.17 (1H, m), 2.97–2.85 (2H, m), 2.62–2.58 (1H, m), 2.29 (3H, s), 2.05–2.10 (1H, m), 1.97–1.83 (1H, m), 1.54–1.47 (2H, m), 0.84–0.79 (3H, t).

EXAMPLE 26

[1S-[1α,2β,3β,4α(1S*,2R*)]]-4-[7-[[2-(3-Chlorophenyl)cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-(3-Chlorophenyl)-1-oxo-2-propenyl]-hexahydro-8,8-dimethyl-3H-3a,6-methano-2,1-benzisothiazole-2,2-dioxide The subtitle compound was prepared according to the method of example 19, step (f) using 3-(3-chlorophenyl)-2-propenoic acid.

MS (APCI) 382/380 (M+H$^+$), 153 (100%)

b) [3aS-[1(1S*,2S*),3aα,6α,7aβ]]-1-[[2-3-Chlorophenyl)cyclopropyl]carbonyl]-hexahydro-8,8-dimethyl-3H-3a,6-methano-2,1-benzisothiazole-2,2-dioxide The subtitle compound was prepared according to the method of example 19, step (g) using the product of step (a).

MS (APCI) 396/394 (M+H$^+$), 411 (100%)

c) (1R-trans)-2-(3-Chlorophenyl)-cyclopropane carboxylic acid

The subtitle compound was prepared according to the method of example 19, step (h) using the product of step (b).

MS (APCI) 195/197 (M–H$^+$), 195 (100%)

d) [1R-trans]-2-(3-Chlorophenyl)cyclopropylamine, [R-(R*,R*)]-2,3-dihydroxybutanedioate (1:1)

The subtitle compound was prepared according to the method of example 20, step (b) using the product of step (c).

NMR δH (d$_6$-DMSO) 1.13–1.23 (2H, m), 2.10–2.20 (1H, m), 2.70–2.74 (1H, m), 3.95 (2H, s), 7.08–7.32 (4H, m)

e) [1S-[1α,2β,3β,4α(1S*,2R*)]]-4-[7-[[2-(3-Chlorophenyl)cyclopropyl]amino]-5-(propylthio)-3H-1,2,3-triazolo[4,5-d]pyrimidin-3-yl]-cyclopentane-1,2,3-triol The title compound was prepared according to the method of example 24, step (f) using the products of step (d) and example 24, step (d).

MS (APCI) 477/479 (M+H⁺), 477 (100%)

NMR δH (d₆-DMSO) 7.33–7.15 (4H, m), 5.00–4.93 (1H, m), 4.68–4.65 (1H, m), 3.94 (1H, br s), 3.79 (1H, br s), 3.20 (1H, br s), 2.97–2.79 (2H, m), 2.64–2.56 (1H, m), 2.26–2.13 (1H, m), 1.92–1.88 (1H, m), 1.70–1.40 (4H, m), 0.98 (3H, t, J=7.2 Hz),

EXAMPLE 27

[1S-[1α,2β,3β,4α(1S*,2R*)]]-4-[7-[[2-(3-Nitrophenyl)cyclopropyl]amino]-5-(propylthio)-3H-1,2,3-triazolo[4,5-d]pyrimidin-3-yl]-cyclopentane-1,2,3-triol a) (1R-trans)-2-(3-Nitrophenyl)-cyclopropane carboxylic acid

Prepared according to the method of example 20, step (a) using 3-nitrostyrene.

MS (APCI) 206 (M–H⁺, 100%)

b) (1R-trans)-2-(3-Nitrophenyl)cyclopropanamine [R-(R*,R*)]-2,3-dihydroxybutanedioate (1:1)

Prepared according to the method of Example 20, step (b) using the product of step (a).

NMR δH (d₆-DMSO) 8.06–7.98 (2H, m), 7.62–7.53 (2H, m), 4.00 (2H, s), 2.84–2.77 (1H, m), 2.41–2.34 (1H, m), 1.31–32 (1H, m), 1.32–1.23 (1H, m).

c) [3aR-[3aα,4a,6a(1R*,2S*),6aα]]-6-[7-[2-[(3-Nitrophenyl)cyclopropyl]amino]-5-(propylthio)-3H-1,2,3-triazolo[4,5-d]pyrimidin-3-yl]-tetrahydro-2,2-dimethyl-4H-cyclopentan-1,3-dioxol-4-ol Prepared according to the method of Example 1, step (a) using the product of step (b) and Example 24, step (b).

d) [1S-[1α,2β,3β,4α(1S*,2R*)]]-4-[7-[[2-(3-Nitrophenyl)cyclopropyl]amino]-5-propylthio)-3H-1,2,3-triazolo[4,5-d]pyrimidin-3-yl]-cyclopentane-1,2,3-triol Prepared according to the method of Example 1, step (b) using the product of step (c).

m.p. 112–4° C.

MS (APCI) 488 (M+H⁺, 100%)

NMR δH (d₆-DMSO) 9.43 (1H, d), 8.08–8.01 (2H, m), 7.70–7.56 (1H, m), 5.13–4.87 (4H, m), 4.69–4.60 (1H, m), 3.97–3.76 (2H, m), 3.31–3.04 (1H, m), 2.93–2.77 (2H, m) 2.54–2.51 (1H, m), 2.38–2.28 (1H, m) 1.97–1.88 (2H, m), 1.63–1.38 (3H, m), 0.76 (3H, t).

EXAMPLE 28

[1S-[(1α,2β,3β,4α(1S*,2R*)]]-4-[7-[[2-(4-Phenoxyphenyl)cyclopropyl]amino]-5-(propylthio)-3H-1,2,3-triazolo[4,5-d]pyrimidin-3-yl]-cyclopentane-1,2,3-triol a) (1R-trans)-2-(4-Phenoxyphenyl)cyclopropane carboxylic acid

Prepared according to the method of Example 20, step (a) using 1-ethenyl4-phenoxy-benzene.

b) (1R-trans)-2-(4-Phenoxyphenyl) cyclopropanamine, [R-(R*,R*)]-2,3-dihydroxybutanedioate (1:1)

Prepared according to the method of Example 20, step b) using the product of step a).

c) [1S-(1α,2β,3β,4α(1S*,2R*)]-4-[7-[[2-(4-Phenoxyphenyl)cyclopropyl]amino]-5-(propylthio)-3H-1,2,3-triazolo[4,5-d]pyrimidin-3-yl]-cyclopentane-1,2,3-triol Prepared according to the method of Example 24, step (f) using the product from step (b) and the product from Example 24, step (d).

MS (APCI) 534 (M+H⁺, 100%)

NMR δH (d₆-DMSO) 9.35 (1H, d), 7.41–7.35 (2H, m), 7.25–7.22 (2H, m), 7.14–7.09 (1H, m), 6.99–6.94 (4H, m), 5.12–5.11(1H, m), 5.04–5.01(1H, m), 4.94–4.91 (2H, m), 4,67–4.64 (1H, m), 3.94–3.92 (1H, m), 3.80 (1H, s), 3.20–3.17 (1H, m), 2.99–2.87 (2H, s), 2.62–2.57 (1H, m), 2.19–2.10 (1H, m), 1.99–1.90 (1H, m), 1.56–1.49 (2H, m), 1.32–1.30 (1H, m), 0.85 (3H, t).

EXAMPLE 29

[1S-[1α,2β,3β,4α(1S*,2R*)]]-4-[7-[[2-(3-Phenoxyphenyl)cyclopropyl]amino]-5-(propylthio)-3H-1,2,3-triazolo[4,5-d]pyrimidin-3-yl]-cyclopentane-1,2,3-triol a) 1-Ethenyl-3-Phenoxy-benzene

A suspension of triphenylmethylphosphonium bromide (25.23 g) and potassium tert-butoxide (1M solution in tetrahydrofuran) (75.67 ml) was stirred at 0° C. for 0.5 h. A solution of 3-phenoxy-benzaldehyde (10.0 g) in THF (10 ml) was added to the mixture and the reaction mixture stirred at 0° C. for 4 h. Ammonium chloride solution was added and the mixture extracted with diethyl ether. The organic extracts were combined, washed with water, dried and concentrated. Purification (SiO₂, isohexane:ethyl acetate 4:1 as eluant) gave the subtitle compound (7.12 g).

NMR δH (CDCl₃) 7.78–7.65 (1H, m), 7.58–7.41 (1H, m), 7.36–7.26 (3H, m), 7.16–7.06 (2H, m), 7.04–7.00 (2H, m), 6.92–6.88 (1H, m), 6.72–6.62 (1H, m), 5.75 (1H, d) 5.27 (1H, m).

b) (1R-trans)-2-(3-Phenoxyphenyl)cyclopropane carboxylic acid

Prepared according to the method of Example 20, step a) using the product from step (a).

MS (APCI) 253 (M–H⁺, 100%)

c) (1R-trans)-2-(3-Phenoxyphenyl) cyclopropanamine, [R-(R*,R*)]-2,3-dihydroxybutanedioate (1:1)

Prepared according to the method of Example 20, step b) using the product of step b).

NMR δH (d₆-DMSO) 7.42–7.36 (2H, m), 7.31–7.25 (1H, m), 7.16–7.11 (1H, m), 7.00–6.96 (2H,m), 6.90–6.88 (1H, m), 6.81–6.77 (2H, m), 3.94 (2H, s), 2.71–2.66 (1H, m) 2.14–2.11 (1H, m), 1.26–1.20 (1H, m), 1.15–1.11 (1H, m).

d) [1S-[1α,2β,3β,4α(1S*,2R*)]]-4-[7-[[2-(3-Phenoxyphenyl)cyclopropyl]amino]-5-(propylthio)-3H-1,2,3-triazolo[4,5-d]pyrimidin-3-yl]-cyclopentane-1,2,3-triol Prepared according to the method of Example 24, step (f) using the product from step (c) and the product from Example 24, step (d).

MS (APCI) 534 (M+H⁺, 100%)

NMR δH (d₆-DMSO) 9.35 (1H, d), 7.41–7.36 (2H, m), 7.32–7.27(1H, t), 7.15–7.10 (1H, m), 7.01–6.95 (3H, m), 6.90 (1H, m), 6.82–6.79 (1H, m), 5.12–5.10 (1H, m), 5.03–5.01 (1H, m), 4.93–4.91 (2H, m), 4.68–4.64 (1H, m), 3.94–3.92 (1H, m), 3.78 (1H, s), 3.20 (1H, m), 2.97–2.85 (2H, m), 2.61–2.57 (1H, m), 2.18–2.13 (1H, m), 1.96–1.92 (1H, m) 1.55–1.47 (2H, m), 1.35–1.32 (1H, m), 0.83 (3H, t).

EXAMPLE 30

[1S-[1α,2β,3β,4α(1S*,2R*)]]-4-[7-[[2-(3-Aminophenyl)cyclopropyl]amino]-5-(propylthio)-3H-1,2,3-triazolo[4,5-d]pyrimidin-3-yl]-cyclopentane-1,2,3-triol A suspension of 5% palladium on charcoal (40 mg) and the product from example 27, step (d) (114 mg) in ethanol (10 ml) was stirred under two atmospheres pressure of hydrogen for 20 hours. The mixture was filtered and purified ($SiO_2$, isohexane:acetone, 1:1 as eluent) to give the title compound (71 mg).

m.p.105–7° C.

MS (APCI) 458 (M+H$^+$, 100%).

NMR δH (d$_6$-DMSO) 9.27 (1H, d), 6.91 (1H, t), 6.39–6.29 (3H, m), 5.16–5.07 (1H, m), 5.06–4.88 (5H, m), 4.70–4.59 (1H, m), 3.95–3.90 (1H, m), 3.84–3.75 (1H, m), 3.21–2.83 (3H, m), 2.64–2.53 (1H, m), 2.02–1.87 (2H, m), 1.72–1.11 (4H, m), 0.86 (3H, t).

EXAMPLE 31

[1S-(1α,2α,3β,5β)]-3-[7-(Butylamino)-5-(propylthio)-3H-1,2,3-triazolo[4,5-d]pyrimidin-3-yl]-5-(3-hydroxypropoxy)-cyclopentane-1,2-diol a) N-Butyl-(2,4-dimethoxyphenyl)methanamine The subtitle compound was prepared according to the method of example 12, step (d) using butylamine.

NMR δH (CDCl$_3$) 0.90 (3H, t, J=7.2 Hz), 1.33 (2H, sextet, J=7.2 Hz), 1.48 (2H, m), 2,57 (2H, m), 3.71 (2H, m), 3.80 (3H, s), 3.81 (3H, s), 6.41–6.46 (2H, m), 7.12 (1H, d, J=8.1 Hz).

b) (1S-cis)-4-[7-[N-Butyl-[(2,4-dimethoxyphenyl)methyl]amino]-5-(propylthio)-3H-1,2,3-triazolo[4,5-d]pyrimidin-3-yl]-2-cyclopentene-1-ol The subtitle compound was prepared according to the method of example 12, step (e) using the products of step (a) and example 12, step c).

MS (APCI) 499(M+H$^+$,100%)

c) [3aR-(3aα,4α,6α,6aα)]-6-[7-[N-Butyl-[(2,4-dimethoxyphenyl)methyl]amino]-5-(propylthio)-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of example 15, step (c) using the product of step (b).

MS (APCI) 573 (M+H$^+$, 100%)

d) [3aS-(3aα,4α,6α,6aα)]-N-Butyl-N-[2,4-(dimethoxyphenyl)methyl]-3-[[[(tetrahydro-2H-pyran-2-yl)oxy]propyl]oxy]-2,2-dimethyl-4H-cylopenta-1,3-dioxol-4-yl]-5-(propylthio)-3H-1,2,3-triazolo[4,5-d]pyrimidin-7-amine The subtitle compound was prepared according to the method of example 13, step (a) using the product of step (c) and 2-(3-bromopropoxy)-2H-tetrahydropyran, except that the reaction was allowed to proceed for 18 hours at reflux temperature.

MS (APCI) 715 (M+H$^+$, 100%)

e) [1S-(1α,2α,3β,5β)]-3-[7-(Butylamino)-5-(propylthio)-3H-1,2,3-triazolo[4,5-d]pyrimidin-3-yl]-5-(3-hydroxypropoxy)-cyclopentane-1,2-diol The title compound was prepared according to the method of example 2, step (b) using the product of step (d).

MS (APCI) 441 (M+H$^+$,100%)

NMR δH (d$_6$-DMSO) 0.91 (3H, t, J=7.5 Hz), 0.99 (3H, t, J=7.5 Hz), 1.34 (2H, sextet, J=7.2 Hz), 1.58–1.74 (6H, m), 2.02 (1H, m), 2.62 (1H, m), 3.08 (2H, m), 3.44–3.56 (6H, m), 3.70 (1H, m), 3.91 (1H, m), 4.40 (1H, t, J=5.1 Hz), 4.54–4.59 (1H, m), 4.95 (1H, q, J=9.0 Hz), 5.03 (1H, d, J=3.9 Hz), 5.10 (1H, d, J=6.3 Hz), 8.97 and 8.60 (1H, t, J=5.4 Hz).

EXAMPLE 32

[1S-[1α,2α,3β,5β(1S*,2R*)]]-3-(2-Hydroxyethoxy)-5-[7-[(2-phenylcyclopropyl)amino]-5-(propylthio)-3H-1,2,3-triazolo[4,5-d]pyrimidin-3-yl]-cyclopentane-1,2-diol a) N-[2,4-(Dimethoxyphenyl)methyl]-N-(2-phenylcyclopropyl)-3-[[3aS-[3aα,4α(1S*,2R*),6α,6aα]]-[[[(tetrahydro-2H-pyran-2-yl)oxy]ethyl]oxy]-2,2-dimethyl-4H-cyclopenta-1,3-dioxol4-yl]-5-(propylthio)-3H-1,2,3-triazolo[4,5-d]pyrimidin-7-amine The subtitle compound was prepared according to the method of example 31, step (d) using the product of example 23, step (a) and 2-(2-bromoethoxy)-2H-tetrahydropyran (prepared according to the method of K. F. Bernady etal. J. Org. Chem., 1979, 44, 1438.)

MS (APCI) 761 (M+H$^+$,100%)

b) [1S-[1α,2α,3β,5β(1S*,2R*)]]-3-(2-Hydroxyethoxy)-5-[7-[(2-phenylcyclopropyl)amino]-5-(propylthio)-3H-1,2,3-triazolo[4,5d]pyrimidin-3-yl]-cyclopentane-1,2-diol The title compound was prepared according to the method of example 2, step (b) using the product of step (a).

MS (APCI) 487 (M+H$^+$,100%)

NMR δH (DMSO-d$_6$) 9.36 (1H, d, 4.0 Hz), 7.31–7.27 (2H, m), 7.20–7.16 (3H, m), 5.13 (1H,d, J=6.4 Hz), 5.06 (1H,d, J=4.0 Hz), 4.97 (1H, q, J=9.2 Hz ), 4.63–4.55 (2H, m), 3.94 (1H, br), 3.75 (1H, m), 3.52–3.47 (4H, m), 3.21 (1H, m), 2.96–2.93 (1H, m), 2.85–2.82 (1H, m), 2.58–2.70 (1H, m), 2.13 (1H, m), 2.03 (1H, m), 1.54–1.46 (3H, m), 1.36–1.31 (1H, m), 0.80 (3H, t, J=7.6 Hz).

EXAMPLE 33

[1S-[1α,2α,3β,5β(1S*,2R*)]]-3-(Hydroxymethyl)-5-[7-[[2-(4-methoxyphenyl)cyclopropyl]amino]-5-(propylthio)-3H-1,2,3-triazolo[4,5-d]pyrimidin-3-yl]-cyclopentane-1,2-diol a) [3aR-[3aα,4α,6α(1R*,2S*),6aα]-Tetrahydro-6-[7-[[2-(4-methoxyphenyl)cyclopropyl]amino]-5-(propylthio)-3H-1,2,3-triazolo[4,5-d]pyrimidin-3-yl]-2,2-dimethyl-4H-cyclopenta-1,3-dioxole-4-methanol Prepared according to the method of Example 1, step a) using the product of Example 20, step (b).

MS (APCI) 527 (M+H$^+$, 100%).

b) [1S-[1α,2α,3β,5β(1S*,2R*)]]-3-
(Hydroxymethyl)-5-[7-[[2-(4-methoxyphenyl)
cyclopropyl]amino]-5-(propylthio)-3H-1,2,3-triazolo
[4,5-d]pyrimidin-3-yl]-cyclopentane-1,2-diol Prepared according to the method of Example 1, step b) using the product of step a).

MS (APCI) 487 (M+H$^+$, 100%)

NMR δH (d$_6$-DMSO) 9.28 (1H, d), 7.14 (4H, d), 6.85 (2H, d), 5.00–4.95 (2H, m), 4,75–4.68 (2H, m), 4.47–4.40 (1H, m), 3.88 (1H, q), 3.73 (3H, s), 3.50–3.40 (2H, m), 3.13–2.80 (3H, m), 2.27–2.02 (3H, m), 1.90–1.77 (1H, m), 1.60–1.40 (3H, m), 1.28–1.20 (1H, m), 0.85 (3H, t).

EXAMPLE 34

[1R-[1a,2a,3b(1R*,2S*),5b]]-3-[7-[[(2-(4-
Chlorophenyl)cyclopropyl)]amino]-5-(propylthio)-
3H-1,2,3-triazolo[4,5-d]pyrimidin-3-yl]-5-
(hydroxymethyl)-cyclopentane-1,2-diol a) [3aR-[3aα,4α,6α(1R*,2S*),6aα]-6-[7-[[2-(4-
Chlorophenyl)cyclopropyl]amino]-5-(propylthio)-
3H-1,2,3triazolo[4,5-d]pyrimidin-3-yl]-tetrahydro-2,
2-dimethyl-4H-cyclopenta-1,3-dioxole-4-methanol Prepared according to the method of Example 1, step a) using the product of Example 22, step b) and 1,4-dioxane as solvent.

MS (APCI) 531 (M+H$^+$, 100%)

NMR δH (CDCl$_3$) 7.31–7.13 (4H, m), 5.28–5.15 (2H, m), 4.72–4.69 (1H, m), 3.82–3.65 (2H, t), 3.06–3.01 (2H, m), 2.62–2.45 (2H, m), 2.45–2.28 (1H, m), 2.21–2.07 (1H, m), 2.01–2.00 (1H, m), 1.68–1.60 (1H, m), 1.58 (3H, s), 1.40–1.35 (2H, m), 1.33 (3H, s), 0.94 (3H, t)

b) [1R-[1a,2a,3b(1R*,2S*),5b]]-3-[7-[[(2-(4-
Chlorophenyl)cyclopropyl)]amino]-5-(propylthio)-
3H-1,2,3-triazolo[4,5-d]pyrimidin-3-yl]-5-
(hydroxymethyl)-cyclopentane-1,2-diol Prepared according to the method of Example 1, step b), using the product of step b).

MS (APCI) 491 (M+H$^+$, 100%)

NMR δH (d$_6$-DMSO) 9.33 (1H, d), 7.35–7.21 (4H, dd), 5.00–4.95 (2H, m), 4.73–4.70 (2H, m), 4.43–4.40 (1H, m), 3.88–3.87 (1H, m), 3.45 (2H, m), 3.15–3.05 (1H, m), 3.00–2.80 (2H, m), 2.27–2.00 (1H, m), 2.17–2.00 (2H, m), 1.90–1.80 (1H, m), 1.60–1.40 (4H, m), 1.40–1.30 (1H, m), 0.82 (3H, t).

EXAMPLE 35

[1R-[1α,2α,3β(1S*,2R*),5β]]-3-[7-[[2-(3-
Chlorophenyl)cyclopropyl]amino]-5-(propylthio)-
3H-1,2,3-triazolo[4,5-d]pyrimidin-3yl]-5-
(hydroxymethyl)-cyclopentane-1,2-diol a) [3aR-[3aα4α,6α(1R*,2S*),6aα]-6-[7-[[2-(3-
Chlorophenyl)cyclopropyl]amino]-5-(propylthio)-
3H-1,2,3-triazolo[4,5-d]pyrimidin-3-yl]-tetrahydro-
2,2-dimethyl-4H-cyclopenta-1,3-dioxole-4-methanol Prepared according to the method of Example 1, step a) using the product of Example 26, step d) and 1,4-dioxane as solvent.

MS (APCI) 531 (M+H$^+$, 100%).

b) [1R-[1α,2α,3β(1S*,2R*),5β]]-3-[7-[[2-(3-
Chlorophenyl)cyclopropyl]amino]-5-(propylthio)-
3H-1,2,3-triazolo[4,5-d]pyrimidin-3-yl]-5-
(hydroxymethyl)-cyclopentane-1,2-diol Prepared according to the method of Example 1, step b) using the product of step a).

MS (APCI) 491 (M+H$^+$, 100%)

NMR δH (d$_6$-DMSO) 9.34 (1H, d), 7.28–7.10 (4H, m), 5.05–4.93 (2H, m), 4.78–4.71 (2H, m), 4.48–4.40 (1H, m), 3.86–3.80 (1H, m), 4.50–4.40 (2H, m), 3.24–3.18 (1H, m), 3.00–2.80 (2H, m), 2.34–2.21 (1H, m), 2.20–2.00 (2H, m), 1.90–1.80 (1H, m), 1.60–1.38 (4H, m), 0.82 (3H, t).

EXAMPLE 36

[1S-[1α,2α,3β,5β(1S*,2R*)]]-3-(Methoxymethyl)-
5-[7-[(2-phenylcyclopropyl)amino]-5-(propylthio)-
3H-1,2,3-triazolo[4,5-d]pyrimidin-3-yl]-
cyclopentane-1,2-diol a) [3aR-[3aa,4a,6a(1R*,2S*),6aa]]-6-[7-[(2,4-
Dimethoxyphenyl)methyl(2-phenylcyclopropyl)
amino]-5-(propylthio)-3H-1,2,3-triazolo[4,5-d]
pyrimidin-3-yl]-tetrahydro-2,2-dimethyl-4H-
cyclopenta-1,3-dioxole4-methanol Prepared according to the method of Example 1, step a) using the product of Example 12, step d).

MS (APCI) 647 (M+H$^+$, 100%).

b) [3aS-[3aa,4a(1S*,2R*),6a,6aa]]-N-[(2,4-
Dimethoxyphenyl)methyl]-3-[6-(methoxymethyl)-2,
2-dimethyl-tetrahydro-4H-cyclopenta-1,3-dioxolan-
4-yl]-N-(2-phenylcyclopropyl)-5-(propylthio)-3H-1,
2,3-triazolo4,5-d]pyrimidine-7-amine Sodium hydride (31 mg, 60% in oil) was added to a solution of the product from step (a) (0.26 g) and methyl iodide (0.15 ml) in N,N-dimethylformamide (1.5 ml) and the resultant mixture was stirred for 2 hours. Water was added and the mixture was extracted with ethyl acetate and the extracts washed with water, dried, concentrated and purified (SiO$_2$, ethyl isohexane:acetone, 4:1 as eluant) to afford the subtitle compound (0.12 g).

MS (APCI) 661 (M+H$^+$, 100%).

c) [1S-[1α,2α,3β,5β(1S*,2R*)]]-3-
(Methoxymethyl)-5-[7-[(2-phenylcyclopropyl)
amino]-5-(propylthio)-3H-1,2,3-triazolo[4,5-d]
pyrimidin-3-yl]-cyclopentane-1,2-diol Prepared according to the method of Example 2, step b) using the product of step b).

m.p. 149–150° C.

MS (APCI) 471 (M+H$^+$, 100%).

NMR δH (d$_6$-DMSO) 9.33 (1H, d), 7.20 (5H, m), 5.02 (1H, m), 4.81 (1H, m), 4.41 (1H, m), 3.85 (1H, m), 3.40 (2H, m), 3.28 (3H, m), 3.20 (1H, m), 2.90 (2H, m), 2.25 (2H, m), 2.13 (1H, m), 1.86 (2H, m), 1.52 (2H, m), 1.49–1.32 (2H, m), 0.83 (3H, t, J=7 Hz).

EXAMPLE 37

[1S-[1α,2α,3β,5β(1S*,2R*)]]-3-(Hydroxymethyl)-5-
[5(methylthio)-7-[(2-phenylcyclopropyl)amino]-3H-
1,2,3-triazolo[4,5-d]pyrimidin-3-yl]-cyclopentane-1,
2-diol a) [1S-[1α,2α,3β,5β(1S*,2R*)]]-3-
(Hydroxymethyl)-5-[7-(2-phenylcyclopropyl)
amino]-5-(propylsulfonyl)-3H-1,2,3-triazolo[4,5-d]
pyrimidin-3-yl]-cyclopentane-1,2-diol Prepared according to the method of Example 4, step (a) using the product of Example 1, step (b).

MS (APCI) 489 (M+H$^+$, 100%)

b) [1S-[1α,2α,3β,5β(1S*,2R*)]]-3-(Hydroxymethyl)-5-[5-(methylthio)-7-[(2-phenylcyclopropyl)amino]-3H-1,2,3-triazolo[4,5-d]pyrimidin-3-yl]-cyclopentane-1,2-diol Prepared according to the method of Example 17, step (b) using the product of step (a).

MS (APCI) 429 (M+H$^+$, 100%)

NMR δH (d$_6$-DMSO) 9.33 (1H, d), 7.31–7.15 (5H, m), 5.03–4.97 (2H, m), 4.74–4.71 (2H, m), 4.47–4.40 (1H, m), 3.91–3.878 (1H, m), 3.51–3.46 (2H, m), 3.19–3.18 (1H, m), 2.33 (3H, s), 2.29–2.24 (1H, m), 2.14–2.10 (2H, m), 1.92–1.80 (1H, m), 1.51–1.47 (1H,m), 1.35–1.32(1H, m).

EXAMPLE 38

[1S-[1α,2α,3β,5β(1S*,2R*)]]-3-(Hydroxymethyl)-5-[7-[(2-phenylcyclopropyl)amino]-5-[(1-methylethyl)thio]-3H-1,2,3-triazolo[4,5-d]pyrimidin-3-yl]-cyclopentane-1,2-diol The title compound was prepared according to the method of Example 4, step b) using the product of Example 37, step a) and 1-methylethanethiol.

MS (APCI) 457 (M+H$^+$, 100%)

NMR δH (d$_6$-DMSO) 9.35 (1H, s), 7.26–7.19 (5H, m), 5.00–4.97 (2H, m), 4.72 (2H, s), 4.41 (1H, s), 3.87 (1H, s), 3.60–3.64 (1H, m), 3.47 (2H, s), 3.17 (1H, s), 2.23–2.27 (1H, m), 2.09 (2H, s), 1.83–1.85 (1H, m), 1.53–1.55 (1H, m), 1.23–1.36 (1H, m), 1.15 (3H, d), 1.09 (3H, d)

EXAMPLE 39

[1S-[1α,2α,3β,5β(1S*,2R*)]]-3-(Hydroxymethyl)-5-[7-(2-phenylcyclopropyl)amino]-5-prop-2-enylthio)-3H-1,2,3-triazolo[4,5-d]pyrimidin-3-yl]-cyclopentane-1,2-diol a) [1S-[1α,2α,3β,5β(1S*,2R*)]]-3-(Hydroxymethyl)-5-[7-[(2-phenylcyclopropyl)amino]-5-(prop-2-enylthio)-3H-1,2,3-triazolo[4,5-d]pyrimidin-3-yl]-cyclopentane-1,2-diol The title compound was prepared according to the method of Example 4, step (b) using the product of Example 37, step (a) and 2-propene-1-thiol.

MS (APCI) 455 (M+H$^+$, 100%)

NMR δH (d$_6$-DMSO) 9.00 (1H, s), 7.30–7.16 (5H, m), 5.95–5.80 (1H, m), 5.22 (1H, d), 5.04–4.98 (2H, m), 4.67 (1H, d), 4.47–4.38 (3H, m), 3.91 (1H, q), 3.75–3.65 (2H, m), 3.55–3.48 (2H, m), 2.30–2.12 (3H, m), 1.93–1.86 (1H, m), 1.50–1.45 (1H, m), 1.34–1.28 (1H, m).

EXAMPLE 40

[1S-[1α,2α,3β,5β(1S*,2R*)]]-3-(Hydroxymethyl-5-[5-(4-methylphenylthio)-7-[(2-phenylcyclopropyl)amino]-3H-1,2,3-triazolo[4,5-d]pyrimidin-3-yl]cyclopentane-1,2-diol Prepared according to the method of Example 4, step (b) using the product of Example 37, step (a) and p-thiocresol.

MS (APCI) 505 (M+H$^+$, 100%)

NMR δH (d$_6$-DMSO) 9.28 (1H, d), 7.48–7.44 (2H, m), 7.32–7.11 (7H, m), 4.94–4.88 (2H, m),4.64–4.60 (2H, m), 4.32–4.27 (1H, m), 3.30–3.20 (2H, m), 3.13–3.10 (1H, m), 2.34 (3H, s), 2.22–2.15 (2H, m), 2.02–1.98 (1H, m), 1.70–1.60 (1H, m), 1.42–1.38 (1H, m), 1.20–1.15 (1H, m).

EXAMPLE 41

[1S-[1α,2α,3β,5β(1S*,2R)]]-3-(Hydroxymethyl)-5-[7-[[2-(4-methylphenyl)cyclopropyl]amino]-5-(propylthio)-3H-1,2,3-triazolo[4,5-d]pyrimidin-3-yl]-cyclopentane-1,2-diol a) [3aR-[3aα,4α,6α(1R*,2S),6aα]-Tetrahydro-2,2-dimethyl-6-[7-[[2-(4-methylphenyl)cyclopropyl]amino]-5-(propylthio)-3H-1,2,3-triazolo[4,5-d]pyrimidin-3-yl]-4H-cyclopenta-1,3-dioxole4-methanol Prepared according to the method of Example 1, step a) using the product of Example 21, step b) and 1,4-dioxane as solvent.

MS (APCI) 511 (M+H$^+$, 100%).

b) [1S-[1α,2α,3β,5β(1S*,2R*)]]-3-(Hydroxymethyl)-5-[7-[[2-4-methylphenyl)cyclopropyl]amino]-5-(propylthio)-3H-1,2,3-triazolo[4,5-d]pyrimidin-3-yl]-cyclopentane-1,2-diol Prepared according to the method of Example 1, step b) using the product of step a).

MS (APCI) 471 (M+H$^+$, 100%)

NMR δH (d$_6$-DMSO) 9.30 (1H, d), 7.09 (4H, s), 5.03–4.92 (2H, m), 4.71 (2H, s), 4.42–4.36 (1H, m), 3.84 (1H, s), 3.56–3.41 (2H, m), 3.20–3.10 (1H, m), 3.00–2.80 (2H, m), 2.27 (3H, s), 2.25–2.20 (1H, m), 2.15–2.05 (2H, m), 1.89–1.81 (1H, m), 1.60–1.40 (3H, m), 1.28 (1H, dd), 0.84 (3H, t).

EXAMPLE 42

[1S-[1α,2α,3β,(R*),5β(1S*,2R*)]]-3-(1-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol Sodium borohydride (0.50 g) was added to a solution of the product of example 8 (2. 10 g) in methanol (100 ml). The mixture was stirred for 1 hour then poured into water (300 ml). The mixture was extracted with diethyl ether, washed with water, dried and concentrated. Purification (HPLC, Chiralpak AD, isohexane:ethanol, 8:2 as eluant) afforded the title compound (0.16 g). Secondary alcohol stereochemistry determined by the method of B Trost etal J. Org. Chem., 1986, 51, 2370.

MS (APCI) 471 (M+H$^+$, 100%)

NMR δH (d$_6$-DMSO) 9.31 (1H, d), 7.31–7.15 (5H, m), 4.91 (2H, m), 4.62 (1H, d), 4.57 (1H, d), 4.37 (1H, m), 3.84 (1H, m), 3.74 (1H, m), 3.18 (1H, m), 2.96–2.81 (2H, m), 2.11 (3H, m), 1.96 (1H, m), 1.54 (3H, m), 1.35 (1H, m), 1.01 (3H, d), 0.79 (3H, t).

EXAMPLE 43

[1S-[1α,2α,3β,(S*),5β(1S*,2R*)]]-3-(1-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol Prepared according to the method of Example 42, further elution (HPLC, Chiralpak AD, isohexane:ethanol, 8:2) afforded the title compound (0.18 g). Secondary alcohol stereochemistry determined by the method of B Trost etal J. Org. Chem., 1986, 51, 2370.

MS (APCI) 471 (M+H$^+$, 100%)

NMR δH (d$_6$-DMSO) 9.33 (1H, d), 7.30–7.16 (5H, m), 4.95 (2H, m), 4.68 (1H, m), 4.62 (1H, d), 4.37 (1H, m), 4.02 (1H, m), 3.62 (1H, m), 3.21 (1H, m), 2.96–2.82 (2H, m), 2.13 (2H, m), 1.89 (2H, m), 1.48 (3H, m), 1.33 (1H, m), 1.15 (3H, d), 0.82 (3H, t).

EXAMPLE 44

[1R-[1α,2α,3β(1R*,2S*),5β]]-3-[5-(Ethylthio)-7-[[2-phenylcyclopropyl]amino]-3H-1,2,3-triazolo[4,5-d]pyrimidin-3-yl]-5-(hydroxymethyl)-cyclopentane-1,2-diol a) 3aR-[3aα,4α,6α(1R*,2S*),6aα]-6-5-(Ethylthio)-7[[-2-phenylcyclopropyl]amino]-3H-1,2,3-triazolo[4,5-d]pyrimidin-3-yl]-tetrahydro-2,2-dimethyl-4H-cyclopenta-1,3-dioxole4-methanol Prepared according to the method of Example 4, step (b) using the product of Example 37, step (a) and ethanethiol.

MS (APCI) 483 (M+H$^+$, 100%)

b) [1R-[1α,2α,3β(1R*,2S*),5β]]-3-[5-(Ethylthio)-7-[[2-phenylcyclopropyl]amino]-3H-1,2,3-triazolo[4,5-d]pyrimidin-3-yl]-5-(hydroxymethyl)-cyclopentane-1,2-diol Prepared according to the method of Example 1, step (b) using the product of step (a).

MS (APCI) 443 (M+H$^+$, 100%)

NMR δH (d$_6$-DMSO) 9.34 (1H, d), 7.31–7.15 (5H, m), 5.01–4.97 (2H, m), 4.73–4.70 (2H, m), 4.45–4.41 (1H, m), 3.88 (1H, q), 3.51–3.45 (2H, m), 3.21–3.17 (1H, m), 2.90–2.86 (2H, m), 2.28–2.23 (1H, m), 2.11–2.08 (2H, m), 1.90–1.82 (1H, m), 1.54–1.51 (1H, m), 1.35–1.30 (1H, m), 1.09 (3H, t).

EXAMPLE 45

[1R-[1α,2α,3β(1R*,2S*),5β]]-3-[7-[[2-[(1,1'-Biphenyl)-4-yl]cyclopropyl]amino]-5-(propylthio)-3H-1,2,3-triazolo[4,5-d]pyrimidin-3-yl]-5-(hydroxymethyl)-cyclopentane-1,2-diol a) (1R-trans)-2-[(1,1'-Biphenyl)-4-yl]cyclopropane carboxylic acid Prepared according to the method of Example 20, step (a) using 1-ethenyl-4-phenyl-benzene.

NMR δH (CDCl$_3$) 7.50–7.30 (7H, m), 7.19 (2H, d), 2.70–2.60 (1H, m), 1.99–1.93 (1H, m), 1.75–1.68 (1H, m), 1.47–1.41 (1H, m).

b) (1R-trans)-2-[(1,1'-Biphenyl)-4-yl] cyclopropanamine, [R-(R*,R*)]-2,3-dihydroxybutanedioate (1:1)

Prepared according to the method of Example 20, step (b) using the product of step (a).

MS (APCI) 210 (M+H$^+$, 100%).

c) [3aR-[3aα,4α,6α(1R*,2S*),6aα]-6-[7-[[2-[(1,1'-Biphenyl)-4-yl]cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 1, step (a) using the product of step (b) and 1,4-dioxane as solvent.

MS (APCI) 573 (M+H$^+$, 100%).

d) [1R-[1α,2α,3β(1R*,2S*),5β]]-3-[7-[[2-[(1,1'-Biphenyl)-4-yl]cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 1, step (b) using the product of step (c).

MS (APCI) 433 (M+H$^+$, 100%)

NMR δH (d$_6$-DMSO) 9.38 (1H, d), 7.64 (2H, d), 7.59 (2H, d), 7.46 (2H, t), 7.33 (1H, t), 7.27 (2H, d), 5.10–5.00 (2H, m), 4.78 (2H, s), 4.47–4.40 (1H, m), 3.92–3.83 (1H, m), 3.50–3.40 (2H, m), 3.27–3.20 (1H, m), 3.00–2.80 (2H, m), 2.35–2.04 (3H, m), 1.89–1.80 (1H, m), 1.70–1.39 (4H, m), 0.79 (3H, t).

EXAMPLE 46

[1R-(1α,2α,3β,5β)]-3-[7-(Butylamino)-5-(cyclopentylthio)-3H-1,2,3-triazolo[4,5-d]pyrimidin-3-yl]-5-(hydroxymethyl)-cyclopentane-1,2-diol Prepared according to the method of Example 4, step (b) using the product of Example 4, step (a) and cyclopentanethiol, followed by the method of Example 2, step (b)

m. p. 187–8° C.

MS (APCI) 437 (M+H$^+$,100%)

NMR δH (d$_6$-DMSO) 8.96 (1H, t), 4.98–4.96 (2H, dd), 4.73–4.69 (2H, m), 4.46–4.39 (1H, m), 3.90–3.85 (1H, m), 3.47 (1H, br s), 3.52–3.43 (4H, m), 2.25–1.28 (17H, m), 0.91 (3H, t).

EXAMPLE 47

[1S-[1α,2α,3β,5β(1S*,2R*)]]-3-(Hydroxyethyl)-5-[7-[(2-phenylcyclopropyl)amino]-5-[4-(trifluoromethyl)-phenylthio]-3H-1,2,3-triazolo[4,5-d]pyrimidin-3-yl]-cyclopentane-1,2-diol The title compound was prepared according to the method of Example 4, step (b) using the product of Example 37, step (a) and 4-(trifluoromethyl)thiophenol.

m. p. 100–102 ° C.

MS (APCI) 559 (M+H$^+$, 100%)

NMR δH (d$_6$-DMSO) 9.44 (1H, d), 7.83 (2H, d), 7.61 (2H, d), 7.29–7.08 (5H, m), 4.90 (2H, m), 4.62 (2H, m), 4.32 (1H, m), 3.75 (1H, m), 3.39–3.27 (2H, m), 3.06 (1H, m) 2.21 (2H, m), 2.01 (1H, m), 1.72 (1H, m). 1.40 (1H, m). 1.19 (1H, m).

EXAMPLE 48

[1S-[1α,2α,3β,5β(1S*,2R*)]]-3-(Hydroxymethyl)-5-[7-[[2-(4-phenoxyphenyl)cyclopropyl]amino]-5-(propylthio)-3H-1,2,3-triazolo[4,5-d]pyrimidin-3-yl]-cyclopentane-1,2-diol a) [1R-(1α,2α,3β,5β)]-3-[7-Chloro-5-(propylthio)-3H-1,2,3-triazolo[4,5-d]pyrimidin-3-yl]-5-(hydroxymethyl)-cyclopentane-1,2-diol A solution of [3aR-(3aα,4α,6α,6aα)]-6-[7-chloro-5-(propylthio)-3H-1,2,3-triazolo[4,5-d]pyrimidin-3-yl]-tetrahydro-2,2-dimethyl-4H-cyclopenta-1,3-dioxole-4-methanol (0.50 g) in acetonitrile (20 ml) was stirred with Dowex® 50WX8-200 (H$^+$-form) ion-exchange resin (0.49 g) at 60° C. for 7 hours then at room temperature overnight. The resin was removed by filtration and the filtrate concentrated. The crude product was purified by chromatography (SiO$_2$, ethyl acetate as eluant) to afford the subtitle compound as a colourless solid (0.31 g).

MS (APCI) 360 (M+H$^+$, 100%).

b) [1S-[1α,2α,3β,5β(1S*,2R*)]]-3-(Hydroxymethyl)-5-[7-[[2-(4-phenoxyphenyl)cyclopropyl]amino]-5-(propylthio)-3H-1,2,3-triazolo[4,5-d]pyrimidin-3-yl]-cyclopentane-1,2-diol Prepared according to the method of Example 1, step (a) using the products of step (a) and Example 28, step (b), and acetonitrile as solvent.

MS (APCI) 549 (M+H$^+$, 100%).

NMR δH (d$_6$-DMSO) 9.33 (1H, d), 7.42–7.34 (2H, m), 7.27–7.17 (2H, m), 7.12 (1H, t), 7.01–6.92 (4H, m), 5.06–4.95 (2H, m), 4.75–4.68 (2H, m), 4.48–4.38 (1H, m), 3.91–3.85 (1H, m), 3.56–3.40 (2H, m), 3.21–3.13 (1H, m), 3.05–2.83 (2H, m), 2.32–2.19 (1H, m), 2.18–2.03 (2H, m), 1.91–1.79 (1H, m), 1.61–1.46 (3H, m), 1.36–1.26 (1H, m), 0.85 (3H, t).

EXAMPLE 49

[1R-[1α,2α,3β(1S*,2R*),5β]]-3-[7-[[2-(2-Chlorophenyl)cyclopropyl]amino]-5-(propylthio)-3H-1,2,3-triazolo[4,5-d]pyrimidin-3-yl]-5-(hydroxymethyl)-cyclopentane-1,2-diol a) (1R-trans)-2-(2-Chlorophenyl)-cyclopropane carboxylic acid Prepared according to the method of Example 20, step (a) using 2-chloro-1-ethenyl-benzene.

MS (APCI) 195 (M–H, 100%)

b) (1R-trans)-2-(2-Chlorophenyl)cyclopropanamine, [R-(R*,R*)]-2,3-dihydroxybutanedioate (1:1)

Prepared according to the method of Example 20, step (b) using the product of step a).

MS (APCI) 166 (M+H$^+$, 100%)

c) [3aR-[3aα,4α,6α(1R*,2S*),6aα]-6-[7-[[2-(2-Chlorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 1, step (a) using the product of step (b) and 1,4-dioxane as solvent.

MS (APCI) 531 (M+H$^+$, 100%).

d) [1R-[1α,2α,3β(1S*,2R*),5β]]-3-[7-[[2-(2-Chlorophenyl)cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 1, step (b) using the product of step (c).

MS (APCI) 471 (M+H$^+$, 100%)

NMR δH (d$_6$-DMSO) 9.38 (1H, d), 7.43 (1H, d), 7.30–7.22 (3H, m), 5.03–4.95 (2H, m), 4.75–4.70 (2H, m), 4.45–4.38 (1H, m), 3.91–3.82 (1H, m), 3.52–3.40 (2H, m), 3.00–2.80 (2H, m), 2.60–2.40 (3H, m), 2.13–2.02 (1H, m), 1.93–1.81 (1H, m), 1.70–1.35 (4H, m), 0.80 (3H, t).

EXAMPLE 50

[1S-[1α,2α,3β,5β(1S*,2R*)]]-3-(2-Hydroxyethoxymethyl)-5-[7-[(2-phenylcyclopropyl)amino]-5-(propylthio)-3H-1,2,3-triazolo[4,5-d]pyrimidin-3-yl]-cyclopentane-1,2-diol a) [3aR-[3aα,4α,6α(1R*,2S*),6aα]-N-[(2,4-Dimethoxyphenyl)methyl]-3-[6-[[2-[(1,1-dimethylethyl)dimethylsilyl]oxy]ethoxymethyl]-tetrahydro-2,2-dimethyl-4H-cyclopenta-1,3-dioxol-4-yl]-N-(2-phenylcyclopropyl)-5-(propylthio)-3H-1,2,3-triazolo[4,5-d]pyrimidine-7-amine Sodium hydride (35 mg, 60% dispersion in oil) and (2-bromoethoxy)-tert-butyldimethylsilane (0.2 ml) were added to a solution of the product from example 36, step (b) (333 mg) in toluene (3 ml) and the reaction mixture heated at 65° C. for 6 h then at 100° C. for 16 hours. Further sodium hydride (35 mg) and silane (0.2 ml) were added and the mixture heated for 6 hours. Ammonium chloride solution was added and the mixture was extracted with ethyl acetate. The organic extracts were dried, concentrated and purified (SiO$_2$, petrol:ether 2:1 and petrol:ethyl acetate 4:1 as eluant) to give the subtitle compound (77 mg).

NMR δH (CDCl$_3$) 7.27–7.12 (6H, m), 6.40–6.28 (2H, m), 5.37–5.17 (3H, m), 3.79 (1H, m), 3.78–3.73 (5H, m), 3.6–3.51 (7H, m), 3.1–2.95 (2H, m), 2.6–2.1 (2H, m), 1.68–1.61 (2H, m), 1.59–1.57 (6H, m), 1.48–1.41 (1H, m), 1.30–1.21 (5H, m), 0.94 (3H, t), 0.86 (9H, s), 0.06 (6H, s).

b) [1S-[1α,2α,3β,5β(1S*,2R*)]]-3-(2-Hydroxyethoxymethyl)-5-[7-[(2-phenylcyclopropyl)amino]-5-(propylthio)-3H-1,2,3-triazolo[4,5-d]pyrimidin-3-yl]cyclopentane-1,2-diol Prepared according to the method of example 2, step (b) using the product of step (a). Purification (HPLC, Novapak® C18 column, 0.1% aqueous ammonium acetate:acetonitrile, isocratic elution 35% MeCN over 30 minutes) afforded the title compound (33 mg).

MS (APCI) 501 (M+H$^+$, 100%)

NMR δH (d$_6$-DMSO) 9.35 (1H, s), 7.38–7.05 (5H, m), 5.09–4.92 (2H, m), 4.81 (1H, d), 4.63–4.54 (1H, m), 4.47–4.38 (1H, m), 3.90–3.84 (1H, m), 3.6–3.3 (8H, m), 3.24–3.16 (1H, m), 3.01–2.79 (2H, m), 2.35–2.08 (3H, m), 1.90–1.78 (1H, m), 1.56–1.44 (2H, m), 1.37–1.27 (1H, m), 0.80 (3H, t).

EXAMPLE 51

[1R-[1α,2β,3β,4α(1R*,2S*)]]-3-Hydroxy-2-methoxy-4-[7-[(2-phenylcyclopropyl)amino]-5-(propylthio)-3H-1,2,3-triazolo[4,5-d]pyrimidin-3-yl]-cyclopentanemethanol (a) [1R-[1a,2a,3b(1R*,2S*),5b]]-3-[7-[N-(2,4-Dimethoxyphenylmethyl)-(2-phenylcyclopropyl)amino]-5-(propylthio)-3H-1,2,3-triazolo[4,5-d]pyrimidin-3-yl]-5-(hydroxymethyl)-cyclopentane-1,2-diol A solution of the product from Example 36, step (a) (1.39 g) in trifluoroacetic acid (1.5 ml)/methanol (15 ml) was stirred for two days. Ethyl acetate was added and the mixture was concentrated. Sodium hydrogen carbonate solution was added and the mixture was extracted with ethyl acetate. The organic extracts were dried, concentrated and purified (SiO$_2$, petrol:acetone 1:1 as eluant) to give the subtitle compound (1.11 g).

MS (APCI) 607 (M+H+, 100%)

(b) [1S-[(1α,2α,3β5β(1S*,2R*)]]-5-[7-[N-(2,4-Dimethoxyphenylmethyl)-[(2-phenylcyclopropyl)amino]]-5-(propylthio)-3H-1,2,3-triazolo[4,5-d]pyrimidin-3-yl]-3-[[[(1,1-dimethylethyl)diphenylsilyl]oxy]methyl]-cyclopentane-1,2-diol A solution of the product of step (a) (1.11 g), imidazole (417 mg) and tert-butylchorodiphenylsilane (0.75 ml) in dry DMF (4 ml) was stirred for 18 hours. Water was added and the mixture was extracted with ethyl acetate. The organic extracts were dried, concentrated and purified (SiO$_2$, petrol:acetone 3:1 as eluant) to give the subtitle compound (1.16 g).

NMR δH (CDCl$_3$) 7.70–7.04 (16H, m), 6.44–6.30 (2H, m), 5.83–5.63 (2H, m), 5.45–5.31 (1H, m), 5.04–4.78 (1H, m), 4.50–4.40 (1H, m), 4.32–4.27 (1H, m), 3.86–3.52 (8H, m), 3.13–2.63 (4H, m), 2.53–2.17 (3H, m), 1.79–1.40 (4H, m), 1.01 (9H, s), 0.97 (3H, t).

(c) [1S-[1α,2α,3β,5β(1S*,2R*)]]-5-[7-[N-(2,4-Dimethoxyphenylmethyl)-[(2-phenylcyclopropyl)amino]]-5-(propylthio)-3H-1,2,3-triazolo[4,5-d]pyrimidin-3-yl]-3-[[[(1,1-dimethylethyl)diphenylsilyl]oxy]methyl]-2-methoxy-cyclopentanol Sodium hydride (65.3 mg) was added to a solution of the diol from step (b) (1.23 g) and methyl iodide (0.13 ml) in DMF (4 ml) and the mixture was stirred for 4 h. Ammonium chloride solution was added and the mixture was extracted with ethyl acetate. The organic extracts were dried, concentrated and purified (SiO$_2$, petrol:acetone 4:1 and petrol:ethyl acetate 2:1 as eluants) to give the subtitle compound (676 mg) as a 1:2.5 mixture with the regioisomeric [1R-[1α,2α,3β,5β(1R*,2S*)]]-3-[7-[N-(2,4-dimethoxyphenylmethyl)-(2-phenylcyclopropyl)amino]]-5-propylthio-3H-1,2,3-triazolo[4,5d]pyrimidin-3-yl]-5-[[[(1,1-dimethylethyl)diphenylsilyl]oxy]methyl]-2-methoxycyclopentanol compound.

NMR δH (CDCl$_3$) 7.5–7.0 (16H, m), 6.43–6.31 (2H, m), 5.84–4.60 (4H, m), 4.35–4.27 (1H, m), 3.82–3.12 (11H, m), 3.15–2.85 (2H, m), 2.64–2.58 (1H, m), 2.53–1.97 (2H, m), 1.77–1.22 (5H, m), 1.01 (9H, s), 0.97 (3H, t).

(d) [1R-[1α,2β,3β,4α(1R*,2S*)]]-3-Hydroxy-2-methoxy-4-[7-[(2-phenylcyclopropyl)amino]-5-(propylthio)-3H-1,2,3triazolo-[4,5-d]pyrimidin-3-yl]cyclopentanemethanol A solution of the mixture of compounds from step (c) (676 mg) in trifluoroacetic acid-water (9:1) (3 ml) was stirred for 20 hours. The solvent was removed in vacuo and the residue was dissoved in (1 ml) and treated with tetrabutylammonium fluoride in THF (2 ml, 1M solution) and stirred for 4 hours. The solvent was removed in vacuo and the residue purified (SiO$_2$, petrol:acetone 2:1, dichloromethane:methanol 29:1 and petrol:ethyl acetate 1:2 as eluants) to give two fractions:—

Fraction 1, 161 mg, [1R-[1α,2β,3β,4α(1R*,2S*)]]-3-hydroxy-2-methoxy-4-[7-[(2-phenylcyclopropyl)amino]-5-(propylthio)-3H-1,2,3-triazolo[4,5-d]pyrimidin-3-yl]cyclopentanemethanol.

Fraction 2, 330 mg, [1R-[1α,2β,3β,4α(1R*,2S*)]]-2-hydroxy-3methoxy-4-[7-[(2-phenylcyclopropyl)amino]-5-propylthio-3H-1,2,3-triazolo[4,5-d]pyrimidin-3-yl]cyclopentanemethanol; further purified in example 52.

Further purification of fraction 1 (HPLC, Novapak® C18 column, 0.1% aqueous ammonium acetate:acetonitrile, isocratic elution 45% MeCN over 40 minutes) afforded the title compound (58.9 mg).

MS (APCI) 471 (M+H+, 100%)

NMR δH (d$_6$-DMSO) 9.33 (1H, bs), 7.34–7.13 (5H, m), 5.10–4.69 (3H, m), 4.60–4.49 (1H, m), 3.68–2.79 (6H, m), 3.37 (3H, s), 2.32–2.07 (3H, m), 1.92–1.80 (1H, m), 1.60–1.47 (3H, m), 1.38–1.28 (1H, m), 0.80 (3H, t).

EXAMPLE 52

[1R-[1α,2β,3β,4α(1R*,2S*)]]-2-Hydroxy-3-methoxy-4-[7-[(2-phenylcyclopropyl)amino]-5-(propylthio)-3H-1,2,3-triazolo[4,5-d]pyrimidin-3-yl]-cyclopentanemethanol Purification of fraction 2 from Example 51 (HPLC, Novapak® C18 column, 0.1% aqueous ammonium acetate:acetonitrile, isocratic elution 45% MeCN over 40 minutes) afforded the title compound (133.5 mg).

MS (APCI) 471 (M+H+, 100%)

NMR δH (d$_6$-DMSO) 9.35 (1H, s), 7.34–7.13 (5H, m), 5.14 (1H, q), 4.79 (1H, s), 4.23–4.05 (2H, m), 3.57–3.25 (5H, m), 3.25–3.18 (1H, m), 3.04–2.79 (2H, m), 2.37–2.06 (3H, m), 1.92–1.80 (1H, m), 1.60–1.47 (3H, m), 1.38–1.28 (1H, m), 0.83 (3H, t).

EXAMPLE 53

[1S-[1α,2α,3β(E),5β(1S*,2R*)]]-3-(3-Hydroxy-prop-1-enyl)-5-[7-[(2-phenylcyclopropyl)amino]-5-(propylthio)-3H-1,2,3-triazolo[4,5-d]pyrimidin-3-yl]-cyclopentane-1,2-diol a) 3-[[3aR-[3aα,4α(E),6α(1R*,2S*),6aα]]-6-[7-[(Cyclopropyl)amino]-5-(propylthio)-3H-1,2,3-triazolo[4,5-d]pyrimidin-3-yl]-tetrahydro-2,2-dimethyl-4H-cyclopenta-1,3-dioxol-4-yl]-2-propenoic acid, methyl ester A solution of the product of Example 1, step (a) (1.6 g) in dimethylsulphoxide (15 ml) was treated with pyridine (0.25 g) followed by trifluoroacetic acid (0.18 g). To this mixture was added 1,3-dicyclohexylcarbodiimide (1.99 g). After stirring for 5 hours at the reaction mixture was treated with methyl(triphenylphosphoranylidene)acetate (1.72 g) and then stirred for a further 18 hours. The mixture was poured into ethyl acetate (300 ml) and treated with oxalic acid (1.59 g). After stirring for 30 minutes the mixture was filtered and the ethyl acetate solution was washed with dilute aqueous sodium bicarbonate and then with dilute aqueous brine, before being dried and concentrated. Purification (SiO$_2$, ethyl acetate:isohexane 1:4 as eluant) afforded the subtitle compound (1.5 g).

MS (APCI) 551 (M+H+, 100%)

b) 3-[[1R-[1α(E),2β,3β,4α(1R *,2S*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-2-propenoic acid, methyl ester Prepared according to the method of Example 2, step (b) using the product of step (a).

MS (APCI) 511 (M+H+, 100%)

c) [1S-[1α,2α,3β(E),5β(1S*,2R*)]]-3-(3-Hydroxyprop-1-enyl)-5-[7-[(2-phenylcyclopropyl)amino]-5-propylthio-3H-1,2,3-triazolo[4,5-d]pyrimidin-3-yl]-cyclopentane-1,2-diol A solution of the product from step (b) (0.7 g) in tetrahydrofuran (25 ml) at −78° C. was treated with DIBAL-H®

(1.5 M solution in toluene, 8.2 ml). The mixture was then stirred at 0° C. for 1 hour before being quenched with methanol (1 ml) and then poured into dilute aqueous sodium hydroxide (50 ml). This mixture was extracted with ethyl acetate (200 ml), the extract was dried and concentrated. Purification (SiO$_2$, ethyl acetate as eluant) afforded the title compound (0.2 g).

MS (APCI) 483 (M+H$^+$, 100%)

NMR δH (d$_6$-DMSO) 9.34 (1H, d), 7.31–7.15 (5H, m), 5.80–5.70 (1H, m), 5.66 –5.58 (1H, m), 5.09 (1H, d), 4.98 (1H, q), 4.88 (1H, d), 4.67 (1H, t), 4.33 (1H, q), 3.93 (2H, t), 3.84 (1H, q), 3.22–3.18 (1H, m), 3.00–2.80 (2H, m), 2.65–2.60 (1H, m), 2.42–2.38 (1H, m), 2.15–2.10 (1H, m), 2.00–1.85 (1H, m),1.55–1.47 (3H, m), 1.35–1.30 (1H, m), 0.85–0.80 (3H, m).

EXAMPLE 54

[1S-[1α,2α,3β,5β(1S*,2R*)]]-3-(3-Hydroxypropyl)-5-[7-[(2-phenylcyclopropyl)amino]-5-(propylthio)-3H-1,2,3-triazolo[4,5-d]pyrimidin-3-yl]-cyclopentane-1,2-diol A solution of the product of Example 53, step (c) (0.2 g) and triisopropylbenzenesulphonylhydrazide (0.3 g) in tetrahydrofuran (10 ml) was heated at 70° C. for 4 hours. The mixture was then purified (SiO$_2$, ethyl acetate as eluant) to afford the title compound (0.13 g).

MS (APCI) 485 (M+H$^+$, 100%)

NMR δH (d$_6$-DMSO) 9.32 (1H, d), 7.31–7.15 (5H, m), 5.00–4.95 (2H, m), 4.71 (1H, d), 4.42–4.36 (2H, m), 3.73 (1H, q), 3.41 (2H, q), 3.20–3.17 (1H, m), 2.97–2.83 (2H, m), 2.37–2.33 (1H, m), 2.13–2.11 (1H, m), 1.95–1.85 (1H, m), 1.77–1.31 (9H, m), 0.83 (3H,t).

EXAMPLE 55

1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-2-methoxyethanone Boron trifluoride etherate (1.0 ml) was added to a solution of the diazoketone, prepared as described in Example 8 (0.60 g) in methanol (50 ml), and the solution heated at 50° C. for 1 hour. The reaction mixture was extracted into ethyl acetate and the extracts washed with water then dried and concentrated. Purification (SiO$_2$, ethyl acetate:dichloromethane 2:3 as eluant) afforded the title compound (0.16 g).

MS (APCI) 499 (M+H$^+$, 100%)

NMR δH (d$_6$-DMSO) 9.36 (1H, d), 7.31–7.16 (5H, m), 5.25 (2H, m), 4.99 (1H, m), 4.30 (1H, m), 4.24 (2H, m), 4.13 (1H, m), 3.21 (3H, s), 3.19 (1H, m), 3.13 (1H, m), 2.96–2.83 (2H, m), 2.35 (2H, m), 2.14 (1H, m), 1.51 (3H, m), 1.34 (1H, m), 0.81 (3H, t).

EXAMPLE 56

[1S-(1α,2α,3β,5β)]-3-(Hydroxymethyl)-5-[7-[[(trans)-2-(3,4-methylenedioxyphenyl)cyclopropyl]amino]-5-(propylthio)-3H-1,2,3-triazolo[4,5-d]pyrimidin-3-yl]-cyclopentane-1,2-diol a) [3aR-[3aα,4α,6α,6aα]-Tetrahydro-2,2-dimethyl-6-[7-[[(trans)-2-(3,4-methylenedioxyphenyl)cyclopropyl]amino]-5-(propylthio)-3H-1,2,3-triazolo[4,5-d]pyrimidin-3-yl]-4H-cyclopenta-1,3-dioxole-4-methanol Prepared according to the method of Example 1, step (a) using (trans)-2-(3,4-methylenedioxyphenyl)cyclopropanamine hydrochloride.

MS (APCI) 541 (M+H$^+$, 100%).

b) [1S-(1α,2α,3β,5β)]-3-Hydroxymethyl-5-[7-[[(trans)-2-(3,4-methylenedioxyphenyl)cyclopropyl]amino]-5-(propylthio)-3H-1,2,3-triazolo[4,5-d]pyrimidin-3-yl]-cyclopentane-1,2-diol Prepared according to the method of Example 1, step (b) using the product of step a).

MS (APCI) 501 (M+H$^+$, 100%)

NMR δH (d$_6$-DMSO) 9.28 (1H, d), 6.84–6.80 (2H, m), 6.71–6.69 (1H, m), 5.96 (2H, s), 5.01–4.97 (2H, m), 4.73–4.71 (2H, m), 4.44–4.40 (1H, m), 3.87 (1H, q), 3.51–3.44 (2H, m), 3.10–3.07 (1H, m), 3.00–2.90 (2H, m), 2.27–2.23 (1H, m), 2.08–2.05 (2H, m), 1.86–1.83 (1H, m), 1.59–1.53 (2H, m), 1.45–1.42 (1H, m), 1.29–1.24 (1H, m), 0.86 (3H, t).

EXAMPLE 57

[1S-[1α,2α,3β,5β(1S*,2R*)]]-3-(Hydroxymethyl)-5-[7-[[2-(3-methoxyphenyl)cyclopropyl]amino]-5-(propylthio)-3H-1,2,3-triazolo[4,5-d]pyrimidin-3-yl]-cyclopentane-1,2-diol a) [3aR-[3aα4α,6α(1R*,2S*),6aα]-Tetrahydro-6-[7-[[2-(3-methoxyphenyl)cyclopropyl]amino]-5-(propylthio)-3H-1,2,3-triazolo[4,5-d]pyrimidin-3-yl]-2,2-dimethyl-4H-cyclopenta-1,3-dioxole-4-methanol Prepared according to the method of Example 1, step (a) using the product of Example 24, step (e).

MS (APCI) 527 (M+H$^+$, 100%).

b) [1S-[1α,2α,3β,5β(1S*,2R*)]]-3-(Hydroxymethyl)-5-[7-[[2-(3-methoxyphenyl)cyclopropyl]amino]-5-(propylthio)-3H-1,2,3-triazolo[4,5-d]pyrimidin-3-yl]-cyclopentane-1,2-diol A solution of the product from step (b) (0.29 g) in 80% aqueous acetic acid (10 ml) was heated at 80° for 1 hour. The solution was concentrated in vacuo and purified by chromatography (SiO$_2$, methanol:dichloromethane, 5:95 as eluant) to give the crude product. Further purification (HPLC, Novapak® C18 column, 0.1% aqueous ammonium acetate:acetonitrile, isochratic elution 45% MeCN over 15 minutes) afforded the title compound as a colourless solid (0.19 g).

MS (APCI) 487 (M+H$^+$, 100%).

NMR δH (d$_6$-DMSO) 9.32 (1H, d), 7.19 (1H, t), 6.78–6.72 (3H, m), 5.04–4.95 (2H, m), 4.75–4.69 (2H, m), 4.47–4.38 (1H, m), 3.91–3.84 (1H, m), 3.75 (3H, s), 3.55–3.41 (2H, m), 3.24–3.17 (1H, m), 3.01–2.92 (1H, m), 2.90–2.81 (1H, m), 2.31–2.19 (1H, m), 2.14–2.04 (2H, m), 1.90–1.79 (1H, m), 1.59–1.45 (3H, m), 1.37–1.30 (1H, m), 0.83 (3H, t).

EXAMPLE 58

[1S-[1α,2α,3β,5β(1S*,2R*)]]-3-(Hydroxymethyl)-5-[7-[[2-(4-hydroxyphenyl)cyclopropyl]amino]-5-(propylthio)-3H-1,2,3-triazolo[4,5-d]pyrimidin-3-yl]-cyclopentane-1,2-diol a) (1R-trans)-2-(4-Hydroxyphenyl)cyclopropanamine, hydrobromide A solution of the free base of the product from Example 20, step (b), (300 mg) in 47% aqueous hydrobromic acid (9 ml) was heated at 100° C. for 2 hours. The reaction mixture was concentrated and the residue azeotroped with toluene (3×30 ml). The residue was then taken into ethanol (30 ml) and the product precipitated by the slow addition of ether (100 ml) to afford the subtitle compound (290 mg).

NMR δH (D$_2$O) 6.98 (2H, m), 6.74 (2H, m), 2.68 (1H, m), 2.25 (1H, m), 1.25 (1H, m), 1.14 (1H, m).

b) [3aR-[3aα,4α,6α(1R*,2S*),6aα]-Tetrahydro-6-[7-[[2-(4-hydroxyphenyl)cyclopropyl]amino]-5-(propylthio)-3H-1,2,3-triazolo[4,5-d]pyrimidin-3-yl]-2,2-dimethyl-4H-cyclopenta-1,3-dioxole-4-methanol Prepared according to the method of Example 1, step (a) using the product of step (a) and tetrahydrofuran as solvent.
MS (APCI) 513 (M+H$^+$, 100%).

c) [1S-[1α,2α,3β,5β(1S*,2R*)]]-3-(Hydroxymethyl)-5-[7-[[2-(4-hydroxyphenyl)cyclopropyl]amino]-5-(propylthio)-3H-1,2,3-triazolo[4,5-d]pyrimidin-3-yl]-cyclopentane-1,2-diol Prepared according to the method of Example 57, step (b) using the product of step (b).
MS (APCI) 473 (M+H$^+$, 100%).
NMR δH (d$_6$-DMSO) 9.25 (1H, d), 7.05 (2H, dd), 6.69 (2H, dd), 6.62 (4H, m), 5.00 (1H, m), 4.41 (1H, m), 3.87 (1H, m), 3.45 (2H, m), 3.05 (1H, m), 2.95 (2H, m), 2.27 (1H, m), 2.06 (2H, m), 1.86 (1H, m), 1.54 (2H, m), 1.39 (1H, m), 1.20 (1H,m), 0.87 (3H, t).

EXAMPLE 59

[1S-[1α,2α,3β,5β(1S*,2R*)]]-3-(Hydroxymethyl)-5-[7-[[2-(3-methylphenyl)cyclopropyl]amino]-5-(propylthio)-3H-1,2,3-triazolo[4,5-d]pyrimidin-3-yl]-cyclopentane-1,2-diol a) [3aR-[3aα,4α,6α(1R*,2S*),6aα]-Tetrahydro-6-[7-[[2-(3-methylphenyl)cyclopropyl]amino]-5-(propylthio)-3H-1,2,3-triazolo[4,5-d]pyrimidin-3-yl]-2,2-dimethyl-4H-cyclopenta-1,3-dioxole-4-methanol Prepared according to the method of Example 1, step (a) using the product of Example 25, step (b).
MS (APCI) 511 (M+H$^+$, 100%).

b) [1S-[1α,2α,3β,5β(1S*,2R*)]]-3-(Hydroxymethyl)-5-[7-[[2-(3-methylphenyl)cyclopropyl]amino]-5-(propylthio)-3H-1,2,3-triazolo[4,5-d]pyrimidin-3-yl]-cyclopentane-1,2-diol Prepared according to the method of Example 57, step (b) using the product of step (a).
MS (APCI) 471 (M+H$^+$, 100%).
NMR δH (d$_6$-DMSO) 9.31 (1H, d), 7.17 (1H, t), 7.07–6.93 (3H, m), 5.06–4.94 (2H, m), 4.76–4.68 (2H, m), 4.48–4.38 (1H, m), 3.91–3.81 (1H, m), 3.56–3.40 (2H, m), 3.21–3.13 (1H, m), 3.03–2.81 (2H, m), 2.29 (3H, s), 2.27–2.18 (1H, m), 2.16–2.02 (2H, m), 1.92–1.78 (1H, m), 1.60–1.43 (3H, m), 1.37–1.26 (1H, m), 0.84 (3H, t).

EXAMPLE 60

[1S-[1a,2a,3b,5b(1S*,2R*)]]-3-(Hydroxymethyl)-5-[7-[[2-(3-phenoxyphenyl)cyclopropyl]amino]-5-(propylthio)-3H-1,2,3-triazolo[4,5-d]pyrimidin-3-yl]-cyclopentane-1,2-diol a) [3aR-[3aα,4α,6α(1R*,2S*),6aα]-Tetrahydro-2,2-dimethyl-6-[7-[[2-(3-phenoxyphenyl)cyclopropyl]amino]-5-(propylthio)-3H-1,2,3-triazolo[4,5-d]pyrimidin-3-yl]4H-cyclopenta-1,3-dioxole4methanol Prepared according to the method of Example 1, step (a) using the product of Example 29, step (c).

MS (APCI) 589 (M+H$^+$, 100%).

b) [1S-[1α,2α,3β,5β(1S*,2R*)]]-3-(Hydroxymethyl)-5-[7-[[2-(3-phenoxyphenyl)cyclopropyl]amino]-5-(propylthio)-3H-1,2,3-triazolo[4,5-d]pyrimidin-3-yl]-cyclopentane-1,2-diol Prepared according to the method of Example 57, step (b) using the product of step (a).
MS (APCI) 549 (M+H$^+$, 100%).
NMR δH (d$_6$-DMSO) 9.32 (1H, d), 7.41–7.38 (2H, m), 7.30 (1H, t), 7.01–6.96 (3H, m), 6.95 (1H, s), 6.80 (1H, dd), 5.01–4.96 (2H, m), 4.73–4.70 (2H, m), 4.45–4.38 (1H, m), 3.51 –3.45 (2H, m), 3.20–3.18 (1H, m), 3.03–2.81 (2H, m), 2.31–2.22 (1H, m), 2.15–2.06 (2H, m), 1.89–1.91 (1H, m), 1.56–1.49 (3H, m), 1.33–1.30 (1H, m), 0.84 (3H, t).

EXAMPLE 61

[1R-[1α,2α,3β(1R*,2S*),5β]]-3-[7-[[2-(4-Fluorophenyl)cyclopropyl]amino]5-(propylthio)-3H-1,2,3-triazolo[4,5-d]pyrimidin-3-yl]-5-(hydroxymethyl)-cyclopentane-1,2-diol a) [3aR-[3aα,4α,6α(1R*,2S*),6aα]-6-[7-[[2-(4-Fluorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4methanol Prepared according to the method of Example 1, step (a) using the product of Example 19, step (i).
MS (APCI) 515 (M+H$^+$, 100%).

b) [1R-[1α,2α,3β(1R*,2S*),5β]]-3-[7-[[2-(4-Fluorophenyl)cyclopropyl]amino]-5-(propylthio)-3H-1,2,3-triazolo[4,5-d]pyrimidin-3-yl]-5 (hydroxymethyl)-cyclopentane-1,2-diol Prepared according to the method of Example 57, step (b) using the product of step (a).
MS (APCI) 475 (M+H$^+$, 100%).
NMR δH (d$_6$-DMSO) 9.33 (1H, d), 7.29–7.17 (2H, m), 7.17–7.07 (2H, m), 5.05–4.95 (2H, m), 4.76–4.68 (2H, m), 4.48–4.38 (1H, m), 3.92–3.84 (1H, m), 3.55–3.41 (2H, m), 3.18–3.05 (1H, m), 3.01–2.81 (2H, m), 2.31–2.19 (1H, m), 2.18–2.04 (2H, m), 1.91–1.79 (1H, m), 1.58–1.46 (3H, m), 1.36–1.28 (1H, m), 0.83 (3H, t).

EXAMPLE 62

[1S-[1α,2α,3β,5β(1S*,2R*)]]-3-(Hydroxymethyl)-5-[7-[[2-(3-nitrophenyl)cyclopropyl]amino]-5-(propylthio)-3H-1,2,3-triazolo[4,5-d]pyrimidin-3-yl]-cyclopentane-1,2-diol a) [3aR-[3aα,4α, 6α(1R*,2S*),6aα]-Tetrahydro-2,2-dimethyl-6-[7-[[2-(3-nitrophenyl)cyclopropyl]amino]-5-(propylthio)-3H-1,2,3-triazolo[4,5-d]pyrimidin-3-yl]-4H-cyclopenta-1,3-dioxole-4-methanol Prepared according to the method of Example 1, step (a) using the product of Example 27, step (b).
MS (APCI) 542 (M+H$^+$, 100%).

b) [1S-[1α,2α,3β,5β(1S*,2R*)]]-3-(Hydroxymethyl)-5-[7-[[2-(3-nitrophenyl)cyclopropyl]amino]-5-(propylthio)-3H-1,2,3-triazolo[4,5-d]pyrimidin-3-yl]-cyclopentane-1,2-diol Prepared according to the method of Example 57, step (b) using the product of step (a).

MS (APCI) 502 (M+H+, 100%).

NMR δH (d6-DMSO) 8.10–8.00 (2H, m), 7.71–7.55 (2H, m), 5.06–4.92 (2H, m), 4.82–4.64 (2H, br), 4.47–4.37 (1H, m), 3.91–3.83 (1H, m), 3.55–3.41 (2H, m), 3.28–3.20 (1H, m), 2.97–2.72 (2H, m), 2.37–2.17 (2H, m), 2.16–2.03 (1H, m), 1.92–1.77 (1H, m), 1,74–1.60 (1H, m), 1.59–1.39 (3H, m), 0.78 (3H, t).

EXAMPLE 63

[1R-[1α,2α,3β,5β(1R*,2S*)]]-3-[7-[[2-(3-Aminophenyl)cyclopropyl]amino]-5-(propylthio)-3H-1,2,3-triazolo[4,5-d]pyrimidin-3-yl]-5-(hydroxymethyl)-cyclopentane-1,2-diol Prepared by the method of Example 30, using the product of Example 62.

MS (APCI) 472 (M+H+, 100%).

NMR δH (d6-DMSO) 6.91 (1H, t), 6.42–6.29 (3H, m), 5.07–4.86 (1H, m), 4.49–4.38 (1H, m), 3.91–3.85 (1H, m), 3.56–3.40 (2H, m), 3.23–3.15 (1H, m), 3.14–2.84 (2H, m), 2.32–2.18 (1H, m), 2.17–2.05 (1H, m), 2.05–1.96 (1H, m), 1.91–1.78 (1H, m), 1.64–1.50 (2H, m), 1.46–1.36 (1H, m), 1.25–1.13 (1H, m), 0.87 (3H, t).

EXAMPLE 64

[1S-[1α,2β,3β,4α(1S*,2R*)]]-4-[7-[[2-(3,5-Dimethoxyphenyl)cyclopropyl]amino]-5-(propylthio)-3H-1 2,3-triazolo[4,5-d]pyrimidin-3-yl]-cyclopentane-1,2,3-triol a) 3-(3,5-Dimethoxyphenyl)-2-propenoic acid

To a solution of 3,5-dimethoxybenzaldehyde (12.5 g) in pyridine (20 ml) was added malonic acid (8.61 g) and piperidine (1 ml). The resulting solution was heated at 100° C. for 16 hours, cooled to room temperature, poured onto ice and acidified using conc. HCl. The resulting precipitate was collected, extracted into sodium bicarbonate solution and washed with isohexane. The aqueous phase was acidified using conc. HCl to yield a white precipitate which was filtered off, washed with water and dried to afford the subtitle compound (11.07 g).

MS (APCI) 207 (M–H+, 100%)

b) 3aS-[1(E),3aα,6α,7aβ]]-1-[3-(3,5-Dimethoxyphenyl)-1-oxo-2-propenyl]-hexahydro-8,8-dimethyl-3H-3a,6-methano-2,1-benzisothiazole-2,2-dioxide The subtitle compound was prepared according to the method of Example 19, step (f) using the product from step (a).

MS (APCI) 406 (M+H+100%).

c) [3aS-[1(1S*,2S*),3aa,6a,7ab]]-1-[[2-(3,5-Dimethoxyphenyl)cyclopropyl]carbonyl]-hexahydro-8,8-dimethyl-3H-3a,6-methano-2,1-benzisothiazole-2,2-dioxide The subtitle compound was prepared according to the method of Example 19, step (g) using the product of step (b).

MS (APCI) 418 (M–H+, 100%)

d) (1R-trans)-2-(3,5-Dimethoxyphenyl)-cyclopropane carboxylic acid

The subtitle compound was prepared according to the method of Example 19, step (h) using the product of step (c).

MS (APCI) 221 (M–H+, 100%)

e) [1R-trans]-2-(3,5-Dimethoxyphenyl) cyclopropanamine, [R-(R*,R*)]-2,3-dihydroxybutanedioate (1:1)

The subtitle compound was prepared according to the method of Example 20, step (b) using the product of step (d).

NMR δH (d6-DMSO) 6.32–6.31 (1H, m), 6.26–6.25 (2H, m), 3.92 (2H, s), 3.71 (6H, s), 2.73–2.66 (2H, m), 2.10–2.03 (1H, m), 1.23–1.08 (2H, m).

f) [1S-[1α,2β,3β,4α(1S*,2R*)]]-4-[7-[[2-(3,5-Dimethoxyphenyl)cyclopropyl]amino]-5-(propylthio)-3H-1,2,3-triazolo[4,5-d]pyrimidin-3-yl]-cyclopentane-1,2,3-triol The title compound was prepared according to the method of Example 24, step (f), using the products of step (e) and Example 24, step (d).

MS (APCI) 503 (M+H+, 100%)

NMR δH (d6-DMSO) 6.35–6.30 (3H, m), 5.10 (1H, bs), 5.00–4.91 (3H, m), 4.67–4.63 (1H, m), 3.93 (1H, s), 3.78–3.77 (1H, m), 3.73 (6H, s), 3.22–3.17 (1H, m), 3.01–2.84 (2H, m), 2.62–2.61 (1H, m), 2.08–2.05 (1H, m), 1.91–1.87 (1H, m), 1.53–1.46 (2H, m), 1.35–1.32 (1H, m), 0.85–0.80 (3H, s).

EXAMPLE 65

[1S-[1a,2a,3b,5b(1S*,2R*)]]-3-[(2-Hydroxy-2,2-dimethyl)ethoxy]-5-[7-[(2-phenylcyclopropyl) amino]-5(propylthio)3H-1,2,3-triazolo[4,5-d] pyrimidin-3-yl]-cyclopentane-1,2-diol.

a) 2-[[[3aR-[3aα,4α(1R*,2S*),6α,6aα]]-6-[7-[N-[(2,4-Dimethoxyphenyl)methyl]-2-(phenylcyclopropyl) amino]-5(propylthio)-3H-1,2,3-triazolo[4,5-d] pyrimidin-3-yl]-tetrahydro-2,2-dimethyl4H-cyclopenta-1,3-dioxol-4-yl]oxy]-1,1-dimethyl-ethanol To a solution of the product from Example 23, step (b) (1.15 g) in tetrahydrofuran (25 ml) at 0° C. was added methylmagnesium bromide (0.45 ml, 3M solution in THF). The reaction was stirred for 1 hour then quenched with 10% ammonium chloride solution and the reaction mixture partitioned between ethyl acetate and water. The organic phase was separated dried and concentrated. Purification (SiO2, ethyl acetate: hexane 1:3 to as eluent) afforded the subtitle compound (0.80 g).

MS (APCI) 705 (M+H+, 100%)

b) [1S-[1a,2a,3b,5b(1S*,2R*)]]-3-[(2-Hydroxy-2,2-dimethyl)ethoxy]-5-[7-[(2-phenylcyclopropyl) amino]-5-(propylthio)-3H-1,2,3-triazolo[4,5-d] pyrimidin-3-yl]-cyclopentane-1,2-diol.

The title compound was prepared according to the method of Example 2, step (b) using the product of step (a).

MS (APCI) 705 (M+H+, 100%)

NMR δH (d6-DMSO) 9.35 (1H, t, J=4.5 Hz), 7.31–7.27 (2H, m), 7.21–7.15 (3H, m), 5.13 (1H, d, J=6.3 Hz), 5.05 (1H, d, J=3.9 Hz), 4.98 (1H, q, J=9.0 Hz) 4.63–4.56 (1H, m), 3.94 (1H, s), 3.74 (1H, s), 3.27 (1H, d, J=8.7 Hz), 3.21 (1H, d, J=9.0 Hz), 3.21 (1H, m), 2.97–2.81 (2H, m), 2.63 (1H, m), 2.13 (1H, m), 2.04 (1H, m), 1.52 (2H, m), 1.48 (1H, m), 1.34 (1H, m), 1.10 (3H, s), 1.09 (3H, s), 0.81 (3H, t, J=7.5 Hz)

EXAMPLE 66

[1S-[1α,2α,3β,5β(1S*,2R*)]]-3-(Hydroxymethyl)-5-[7-[[2-[4-(1-methylethyloxy)phenyl]cyclopropyl]amino]-5-(propylthio)-3H-1,2,3-triazolo[4,5-d]pyrimidin-3-yl]-cyclopentane-1,2-diol a) 1-Ethenyl-4-(1-methylethoxy)benzene

Prepared according to the method of Example 29, step (a) using 4-(1-methylethoxy)-benzaldehyde.

MS (EI) 162 (M+, 100%)

b) (1R-trans)-2-[4-(1-Methylethoxy)phenyl]-cyclopropane carboxylic acid

Prepared according to the method of Example 20, step (a) the product of step (a).

MS (APCI) 219 (M–H+, 100%).

c) (1R-trans)-2-[4-(1-Methylethoxy)phenyl]-cyclopropanamine

Prepared according to the method of Example 19, step i) using the product of step (b).

NMR δH (d$_6$-DMSO) 7.00 (2H, d), 6.76 (2H, d), 4.51 (1H, sept), 2.30–2.25 (1H, m), 1.67–1.61 (1H, m), 1.21 (6H, d), 0.85–0.75 (2H, m).

d) [3aR-[3aα,4a,6a(1R*,2S*),6aα]-Tetrahydro-2,2-dimethyl-6-[7-[[2-[4-(1-methylethoxy)phenyl]cyclopropyl]amino]-5-(propylthio)-3H-1,2,3-triazolo[4,5-d]pyrimidin-3-yl]4H-cyclopenta-1,3dioxole4-methanol Prepared according to the method of Example 1, step (a) using the product of step (c).

MS (APCI) 219 (M+H+, 100%).

e) [1S-[1α,2α,3β,5β(1S*,2R*)]]-3-(Hydroxymethyl)-5-[7-[[2-[4-(1-methylethyloxy)phenyl]cyclopropyl]amino]-5-(propylthio)-3H-1,2,3-triazolo[4,5-d]pyrimidin-3-yl]-cyclopentane-1,2-diol Prepared according to the method of Example 57, step (b) using the product of step (d).

NMR δH (d$_6$-DMSO) 9.28 (1H, d), 7.11 (2H, d), 6.83 (2H, m), 5.01–4.97 (2H, m), 4.74–4.70 (2H, m), 4.55 (1H, sept), 4.46–4.39 (1H, m), 3.89–3.85 (1H, m), 3.51–3.45 (2H, m), 3.14–3.07 (1H, m), 3.03–2.82 (2H, m), 2.30–2.20 (1H, m), 2.09–2.06 (2H, m), 1.89–1.79 (1H, m), 1.59–1.49 (1H, m), 1.47–1.41 (1H, m), 1.24 (7H, m), 0.99 (3H, t).

EXAMPLE 67

[1S-[1a,2a,3b,5b(1S*,2R*)]]-3-(3-Hydroxypropoxy)-5-[7-[(2-phenylcyclopropyl)amino]-5-(propylthio)-3H-1,2,3-triazolo[4,5-d]pyrimidin-3-yl]-cyclopentane-1,2-diol a) [3aS-[3aα,4α(1S*,2R*),6α,6aα]]-N-[2,4-(Dimethoxyphenyl)methyl]-3-[2,2-dimethyl-6-[[[3-(tetrahydro-2H-pyran-2-yl)oxy]propyl]oxy]-4H-cyclopenta-1,3-dioxol-4-yl]-N-(2-phenylcyclopropyl)-5-(propylthio)-3H-1,2,3-triazolo[4,5-d]pyrimidin-7-amine.

The subtitle compound was prepared according to the method of Example 31, step (d) using the product of Example 23, step (a) and 2-(3-bromopropoxy)-2H-tetrahydropyran.

MS (APCI) 775 (M+H+, 100%)

b) [1S-[1a,2a,3b,5b(1S*,2R*)]]-3-(3-Hydroxypropoxy)-5-[7-[(2-phenylcyclopropyl)amino]-5-(propylthio)-3H-1,2,3-triazolo[4,5-d]pyrimidin-3-yl]-cyclopentane-1,2-diol The title compound was prepared according to the method of Example 2, step (b) using the product of step (a).

MS (APCI) 501 (M+H+, 100%)

NMR δH (d$_6$-DMSO) 9.34 (1H, d, J=4,0 Hz), 7.32–7.25 (2H, m), 7.22–7.15 (3H, m), 5.11 (1H,d, J=3.3 Hz), 5.04 (1H,d, J=3.8 Hz), 4.97 (1H, q, J=9.1 Hz), 4.62–4.52 (1H, m), 4.40 (1H, t, 5.2 Hz), 3.95–3.92 (1H, m), 3.75–3.66 (1H, m), 3.59–3.41 (4H, m), 3.25–3.14 (1H, m), 3.13–2.78 (2H, m), 2.70–2.55 (1H, m), 2.30–1.95 (2H, m), 1.73–1.61 (2H, m), 1.57–1.28 (4H, m), 0.82 (3H, t, J=7.5 Hz).

EXAMPLE 68

[1S-[1α,2β,3β,4α(1S*,2R*)]]4-[7-[[2-(3,4-Difluorophenyl)cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-(3,4-Difluorophenyl)-1-oxo-2-propenyl]-hexahydro-8,8-dimethyl-3H-3a,6-methano-2,1-benzisothiazole-2,2-dioxide The subtitle compound was prepared according to the method of Example 19, step (f) using 3-(3,4-difluorophenyl)-2-propenoic acid.

MS (APCI) 382 (M+H+, 100%)

b) [3aS-[1(1S*,2S*),3aα,6a,7ab]]-1-[[2-(3,4-Difluorophenyl)cyclopropyl]carbonyl]-hexahydro-8,8-dimethyl-3H-3a,6-methano-2,1-benzisothiazole-2,2-dioxide The subtitle compound was prepared according to the method of Example 19, step (g) using the product of step (a).

MS (APCI) 396 (M+H+, 100%)

c) (1R-trans)-2-(3,4-Difluorophenyl)-cyclopropane carboxylic acid

The subtitle compound was prepared according to the method of Example 19, step (h) using the product of step (b).

NMR δH (CDCl$_3$) 7.68 (1H, dd, J=10.0, J=8.5 Hz), 7.46–7.31 (2H, m), 3.12–3.03(1H, m), 2.37 (1H,dt, J=8.5, J=4.4 Hz), 2.17 (1H,dt, J=9.2, J=4.8 Hz), 1.86 (1H, ddd, J=8.5, J=6.9, J=5.2 Hz).

d) (1R-trans)-2-(3,4-Difluorophenyl)cyclopropanamine, [R-(R*,R*)]-2,3-dihydroxybutanedioate (1:1)

The subtitle compound was prepared according to the method of Example 20, step (b) using the product of step (c).

MS (APCI) 170 (M+H+, 100%)

e) [1S-[1α,2β,3β,4α(1S*,2R*)]]-4-[7-[[2-(3,4-Difluorophenyl)cyclopropyl]amino]-5-(propylthio)-3H-1,2,3triazolo[4,5-d]pyrimidin-3-yl]-cyclopentane1,2,3-triol The title compound was prepared according to the method of Example 24, step (f) using the products of step (d) and Example 24, step (d).

MS (APCI) 479 (M+H⁺, 100%)

NMR δH (d₆-DMSO) 9.36 (1H, d, J=4.2 Hz), 7.40–7.22 (2H, m), 7.10–7.00 (1H, m), 5.13–4.90 (4H, m), 4.68–4.60 (1H, m), 3.97–3.90 (1H, m), 3.82–3.76 (1H, m), 3.20–2.80 (3H, m), 2.62–2.50 (1H, m), 2.32–2.04 (1H, m), 1.96–1.83 (1H, m), 1.75–1.36 (4H, m), 0.82 (3H, t, J=7.5 Hz).

EXAMPLE 69

[1R-[1α,2α,3β(1S*,2R*),5β]]-3-[7-[[2-(3,4-Difluorophenyl)cyclopropyl]amino]-5-propylthio)-3H-1,2,3-triazolo[4,5-d]pyrimidin-3-yl]-5-(hydroxymethyl)-cyclopentane-1,2-diol a) [3aR-[3aα,4α,6α(1R*,2S*),6aα]-6-[7-[[2-(3,4-Difluorophenyl)cyclopropyl]amino]-5-propylthio)-3H-1,2,3-triazolo[4,5-d]pyrimidin-3-yl]-tetrahydro-2,2-dimethyl4H-cyclopenta-1,3-dioxole-4-methanol Prepared according to the method of Example 1, step (a) using the product of Example 68, step (d).

MS (APCI) 533 (M+H⁺, 100%).

b) [1R-[1α,2α,3β(1S*,2R*), 5β]]-3-[7-[[2-(3,4-Difluorophenyl)cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 57, step (b) using the product of step (a).

NMR δH (d₆-DMSO) 9.36 (1H, d), 7.39–7.27 (2H, m), 7.10–7.05 (1H, m), 5.05–4.95 (2H, m), 4.74–4.71 (2H, m), 4.46–4.39 (1H, m), 3.90–3.86 (1H, m), 3.53–3.41 (2H, m), 3.18–3.12 (1H, m), 3.00–2.81 (2H, m), 2.31–2.21 (1H, m), 2.16–2.06 (2H, m), 1.90–1.79 (1H, m), 1.58–1.46 (3H, m), 1.41–1.34 (1H, m), 0.83 (3H, t).

EXAMPLE 70

[1S-[α,2β,3β,4α(1S*,2R*)]]-4-[7-[[2-(3,5-Difluorophenyl)cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-(3,5-Difluorophenyl)-1-oxo-2-propenyl]-hexahydro-8,8-dimethyl-3H-3a,6-methano-2,1-benzisothiazole-2,2-dioxide The subtitle compound was prepared according to the method of Example 19, step (f) using 3-(3,5-difluorophenyl)-2-propenoic acid.

MS (APCI) 382 (M+H⁺, 100%)

b) [3aS-[1(1S*,2S*),3aα,6α,7ab]]-1-[[2-(3,5-Difluorophenyl)cyclopropyl]carbonyl]-hexahydro-8,8-dimethyl-3H-3a,6-methano-2,1-benzisothiazole-2,2-dioxide The subtitle compound was prepared according to the method of Example 19, step (g) using the product of step (a).

MS (APCI) 396 (M+H⁺, 100%)

c) (1R-trans)-2-(3,5-Difluorophenyl)-cyclopropane carboxylic acid

The subtitle compound was prepared according to the method of Example 19, step (h) using the product of step (b).

MS (APCI) 197 (M–H⁺, 100%)

d) [1R-(trans)]-2-(3,5-Difluorophenyl) cyclopropanamine, [R-(R*,R*)]-2,3-dihydroxybutanedioate (1:1)

The subtitle compound was prepared according to the method of Example 20, step (b) using the product of step (c).

NMR δH (d₆-DMSO) 7.00–6.84 (3H, m), 3.98 (2H, s), 2.75–2.69 (1H, m), 2.16–2.10 (1H, m), 1.28–1.15 (2H, m).

[1S-[1α,2β,3β,4α(1S*,2R*)]]4-[7-[[2-(3,5-Difluorophenyl)cyclopropyl]amino]-5-(propylthio)-3H-1,2,3-triazolo[4,5-d]pyrimidin-3-yl]-cyclopentane-1,3-triol The title compound was prepared according to the method of Example 24, step (f) using the products of step (d) and Example 24, step (d).

MS (APCI) 479 (M+H⁺, 100%)

NMR δH (d₆-DMSO) 9.38 (1H, d, J=4.2 Hz), 7.01–6.95 (3H, m), 5.11–4.91 (4H, m), 4.68–4.64 (1H, m), 3.94–3.91 (1H, m), 3.77 (1H, bs), 3.20–2.80 (3H, m), 2.65–2.55 (1H, m), 2.20–2.10 ( 1H, m), 1.95–1.85 (1H, m), 1.63–1.43 (4H, m), 0.81 (3H, t, J=7.5 Hz).

EXAMPLE 71

[1S-[1α,2β,3β,4α(1S*,2R*)]]-4-[7-[[2-[[1,1'-Biphenyl]-3-yl]cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-[[1,1'-Biphenyl]-3-yl]-1-oxo-2-propenyl]-hexahydro-8,8-dimethyl-3H-3a,6-methano-2,1-benzisothiazole-2,2-dioxide The subtitle compound was prepared according to the method of Example 19, step (f) using 3-(3,5-difluorophenyl)-2-propenoic acid.

MS (APCI) 422 (M+H⁺, 100%)

b) [3aS-[1(1S*,2S*),3aα,6a,7ab]]-1-[[2-[[1,1'-Biphenyl]-3-yl]cyclopropyl]carbonyl]-hexahydro-8,8-dimethyl-3H-3a,6-methano-2,1-benzisothiazole-2,2-dioxide The subtitle compound was prepared according to the method of Example 19, step (g) using the product of step (a).

MS (APCI) 436 (M+H⁺, 100%)

c) (1R-trans)-2-[[1,1'-Biphenyl]-3-yl]-cyclopropane carboxylic acid

The subtitle compound was prepared according to the method of Example 19, step (h) using the product of step (b).

MS (APCI) 237 (M–H⁺, 100%)

d) [1R-(trans)]-2-[[1,1'-Biphenyl]-3-yl] cyclopropanamine, [R-(R*,R*)]-2,3-dihydroxybutanedioate (1:1)

The subtitle compound was prepared according to the method of Example 20, step (b) using the product of step (c).

MS (APCI) 210 (M–H⁺, 100%)

e) [1S-[1 α,2β,3β,4α(1S*, 2R*)]]-4-[7-[[2-[[1,1'-Biphenyl]-3-yl]cyclopropyl]amino]-5-(propylthio)-3H-1,2,3-triazolo[4,5-d]pyrimidin-3-yl-cyclopentane-1,2,3-triol The title compound was prepared according to the method of Example 24, step (f) using the products of step (d) and Example 24, step (d).

MS (APCI) 519 (M+H+, 100%)

NMR δH (d$_6$-DMSO) 9.37 (1H, d, J=4.2 Hz), 7.70–7.18 (9H, m), 5.12–4.91 (4H, m), 467–4.64 (1H, m), 3.94–3.93 (1H, m), 3.78 (1H, bs), 3.28–2.80 (3H, m), 2.62–2.50 (1H, m), 2.25–2.15 (1H, m), 1.95–1.85 (1H, m), 1.59–1.41 (4H, m), 0.75 (3H, t,J=7.5 Hz).

EXAMPLE 72

[1R-[1α,2α,3β(1R*,2S*),5β]]-3-[7-[[2-[1,1'-Biphenyl]-3-yl]cyclopropyl]amino]-5-(propylthio)-3H-1,2,3-triazolo[4,5-d]pyrimidin-3-yl]-5-(hydroxymethyl)-cyclopentane-1,2-diol a) [3aR-[3aα,4α,6α(1R*,2S*),6aα]-6-[7-[[2-[1,1'-Biphenyl]-3-yl]cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 1, step (a) using the product of Example 71, step (d).

MS (APCI) 573 (M+H+, 100%).

b) [1R-[1α,2α,3β(1R*,2S*),5β]]-3-[7-[[2-[1,1'-Biphenyl]-3-yl]cyclopropyl]amino]-5-(propylthio)-3H-1,2,3-triazolo[4,5-d]pyrimidin-3-yl]-5 (hydroxymethyl)-cyclopentane-1,2-diol Prepared according to the method of Example 57, step (b) using the product of step (a).

5 MS (APCI) 533 (M+H+, 100%).

NMR δH (d$_6$-DMSO) 9.35 (1H, d), 7.68 (2H, dd), 7.49–7.44 (4H, m), 7.41–7.33 (2H, m), 7.19 (1H, d), 6.80 (1H, dd), 5.05–4.95 (2H, m), 4.74–4.71 (2H, m), 4.46–4.39 (1H, m), 390–3.87 (1H, m), 3.51–3.45 (2H, m), 3.27–3.20 (1H, m), 3.00–2.77 (2H, m), 2.30–2.17 (2H, m), 2.12–2.04 (1H, m), 1.90–1.79 (1H, m), 1.60–1.53 (1H, m), 1.50–1.41 (3H, m), 0.77 (3H, t).

EXAMPLE 73

N-Ethyl-[[[1S-[1α,2β,3β,4α(1S*,2R*)]]-2,3-dihydroxy-4-[7-[(2-phenylcyclopropyl)amino]-5-(propylthio)-3H-1,2,3-triazolo[4,5-d]pyrimidin-3-yl]-cyclopentyl]oxy]-acetamide a) [1S-[1α,4α(1S*,2R*)]]-2-[[4-[7-[(2-Phenylcyclopropyl)amino]-5-(propylthio)-3H-1,2,3-triazolo[4,5-d]pyrimidin-3-yl]-2-cyclopentenyl]oxy] acetic acid The subtitle compound was prepared according to the method of Example 2, step (b) using the product of example 13, step (a).

MS (APCI) 467 (M+H+, 100%)

b) N-Ethyl-2-[[[1S-[1α,4α(1S*,2R*)]]-4-[7-[(2-phenylcyclopropyl)amino]-5-(propylthio)-3H-1,2,3-triazolo[4,5-d]pyrimidin-3yl]-2-cyclopentenyl]oxy]-acetamide.

The subtitle compound was prepared according to the method of Example 16, using the product of step (a) and 40% aqueous ethylamine.

MS (APCI) 494 (M+H+, 100%).

c) N-Ethyl-[[[1S-[1α,2β,3β,4α(1S*,2R*)]]-2,3-dihydroxy-4-[7-[(2-phenylcyclopropyl)amino]-5-(propylthio)-3H-1,2,3-triazolo[4,5-d]pyrimidin-3-yl]-cyclopentyl]oxy]-acetamide The title compound was prepared according to the method of Example 12, step (f) using the product of step (b).

MS (APCI) 528 (M+H+, 100%).

NMR δH (d$_6$-DMSO) 9.36 (1H, m), 7.75–7.68 (1H, m), 7.31–7.26 (2H, m), 7.21–7.15 (3H, m), 5.23–5.18 (2H, m), 5.00–4.92 (1H, m), 4.60–4.53 (1H, m), 4.05–4.01 (1H, m), 3.93–3.78 (3H, m), 3.24–3.08 (3H, m), 2.98–2.90 (1H, m), 2.87–2.79 (1H, m), 2.69–2.61 (1H, m), 2.30–2.06 (2H, m), 1.72–1.29 (4H, m), 1.04 (3H, t, J=7.1 Hz), 0.80 (3H, t, J=7.2 Hz).

EXAMPLE 74

[1S-[1α,2β,3β,4α(1S*,2R*)]]-4-[7-[[2-(3-Methoxy-4-methylphenyl)cyclopropyl]amino]-5-(propylthio)-3H-1,2,3-triazolo[4,5-d]pyrimidin-3-yl]-cyclopentane-1,2,3-triol a) 3-(3-Methoxy-4-methylphenyl)-2-propenoic acid The subtitle compound was prepared according to the method of Example 64, step (a) using (3-methoxy-4-methyl) benzaldehyde.

MS (APCI) 191 (M−H+, 100%)

b) [3aS-[1(E),3aα,6α,7aβ]]-Hexahydro-1-[3-(3-methoxy-4-methylphenyl)-1-oxo-2-propenyl]-8,8-dimethyl-3H-3a,6-methano-2,1-benzisothiazole-2,2-dioxide The subtitle compound was prepared according to the method of Example 19, step (f) using the product of step (a).

MS (APCI) 390 (M+H+, 100%)

c) [3aS-[1(1S*,2S*),3aa,6a,7ab]]-Hexahydro-1-[[2-(3-methoxy-4-methylphenyl)cyclopropyl]carbonyl]-8,8-dimethyl-3H-3a,6-methano-2,1-benzisothiazole-2,2-dioxide The subtitle compound was prepared according to the method of Example 19, step (g) using the product of step (b).

MS (APCI) 404 (M+H+, 100%)

d) (1R-trans)-2-(3-Methoxy-4-methylphenyl) cyclopropane carboxylic acid

The subtitle compound was prepared according to the method of Example 19, step (h) using the product of step (c).

NMR δH (CDCl$_3$) 7.04 (1H, d, J=7.3 Hz), 6.60 (1H, s), 6.59 (1H, d, J=7.3 Hz), 3.82 (3H, s), 2.63–2.55 (1H, m), 2.18 (3H, s), 1.89 (1H, ddd, J=9.2, J=5.2, J=4.2 Hz), 1.64 (1H, dt, J=9.4, J=4.6 Hz ), 1.40 (1H, ddd, J=11.3, J=6.7, J=4.6 Hz ).

e) [1R-(trans)]-2-(3-Methoxy-4-methylphenyl) cyclopropanamine, [R-(R*,R*)]-2,3-dihydroxybutanedioate (1:1)

The subtitle compound was prepared according to the method of Example 20, step (b) using the product of step (d).

MS (APCI) 178 (M+H+, 100%)

f) [1S-[1α,2β,3β,4α(1S*,2R*)]]-4-[7-[[2-(3-Methoxy-4-methylphenyl)cyclopropyl]amino]-5-(propylthio)-3H-1,2,3-triazolo[4,5-d]pyrimidin-3-yl]-cyclopentane-1,2,3-triol The title compound was prepared according to the method of Example 24, step (f) using the products of step (e) and Example 24, step (d).

MS (APCI) 487 (M+H+, 100%)

NMR δH (d$_6$DMSO) 9.31 (1H, d, J=4.2 Hz), 7.03 (1H, d, J=7.7 Hz), 6.77 (1H, m), 6.64 (1H, dd, J=7.7, J=1.2 Hz), 5.12–4.89 (4H, m), 4.70–462 (1H, m)3.97–3.89 (1H, m), 3.80 (3H, s), 3.81–3.76 (1H, m), 3.22–2.80 (3H, m), 2.64–2.53 (1H, m), 2.10 (3H, s), 2.27–2.06 (1H, m), 1.96–1.87 (1H, m), 1.73–1.27 (4H, m), 0.82 (3H, t, J=7.5 Hz).

EXAMPLE 75

[1R-[1α,2α,3β(1R*,2S*),5β]]-3-[7-[[2-(4-N,N-Dimethylaminophenyl)cyclopropyl]amino]-5-(propylthio)-3H-1,2,3-triazolo[4,5-d]pyrimidin-3-yl]-5-hydroxymethyl-cyclopentane-1,2-diol a) [3aS-[1(E),3aα,6α,7aβ]]-1-[3-(4-N,N-Dimethylaminophenyl)1-oxo-2-propenyl]-hexahydro-8,8-dimethyl-3H-3a,6-methano-2,1-benzisothiazole-2,2-dioxide Prepared according to the method of Example 19, step (f) using (E)-3-(4-N,N-dimethylaminophenyl)2-propenoyl chloride (Prepared by the method of K. Venkataraman et al., Tetrahedron Lett., 1979, 32, 3037).

MS (APCI) 389 (M+H$^+$, 100%)

b) [3aS-[1(1S*2S*)3aa,6a,7ab]]-1-[[2-(4-N,N-Dimethylaminophenyl)cyclopropyl]carbonyl]-hexahydro-8,8-dimethyl-3H-3a,6-methano-2,1-benzisothiazole-2,2-dioxide Prepared according to the method of Example 19, step (g) using the product of step (a).

MS (APCI) 403 (M+H$^+$, 100%)

c) (1R-trans)-2-(4-N,N-Dimethylaminophenyl)-cyclopropane carboxylic acid

Prepared according to the method of Example 19, step (h) using the product of step (b).

MS (APCI) 206 (M+H$^+$, 100%)

d) (1R-trans)-2-(4-N,N-Dimethylaminophenyl) cyclopropanamine, [R-(R*,R*)]-2,3-dihydroxybutanedioate (1:1)

Prepared according to the method of Example 20, step (b) using the product of step (c).

NMR δH (d$_6$-DMSO) 6.95 (2H, d), 6.64 (2H, d), 3.91 (2H, s), 2.84 (6H, s), 2.61–2.56 (1H, m), 2.12–2.05 (1H, m), 1.21–1.14 (1H, m), 1.06–0.98 (1H, m).

e) [3aR-[3aα,4α,6α(1R*,2S*),6aα]-6-[7-[[2-(4-N,N-Dimethylaminophenyl)cyclopropyl]amino]-5-(propylthio)-3H-1,2,3-triazolo[4,5-d]pyrimidin-3-yl]-tetrahydro-2,2-dimethyl-4H-cyclopenta-1,3dioxole-4-methanol Prepared according to the method of Example 1, step (a) using the product of step (d).

MS (APCI) 540 (M+H$^+$, 100%)

f) [1R-[1α,2α,3β(1R*,2S*),5β]]-3-[7-[[2-(4-N,N-dimethylaminophenyl)cyclopropyl]amino]-5-(propylthio)-3H-1,2,3-triazolo[4,5-d]pyrimidin-3-yl]-5-hydroxymethyl-cyclopentane-1,2-diol Prepared according to the method of Example 1, step (b) using the product of step (e).

MS (APCI) 500 (M+H$^+$, 100%)

NMR δH (d$_6$-DMSO) 9.25 (1H, d), 7.04 (2H, d), 6.67 (2H, d), 5.01–4.96 (2H, m), 4.73–4.70 (2H, m), 4.46–4.41 (1H, m), 3.88 (1H, q), 3.51–3.44 (2H, m), 3.10–2.90 (3H, m), 2.85 (6H, s), 2.27–2.23 (1H, m), 2.08–2.01 (2H, m), 1.87–1.82 (1H, m), 1.60–1.53 (2H m), 1.40–1.37 (1H, m), 1.21–1.18 (1H, m), 0.86 (3H, t).

EXAMPLE 76

[1R-[1α,2α,3β(1R*,2S*),5β]]-3-[7-[[2-(3-Fluoro-4-methoxyphenyl)cyclopropyl]amino]-5-(propylthio)-3H-1,2,3-triazolo[4,5-d]pyrimidin-3-yl]-5-(hydroxymethyl)-cyclopentane-1,2-diol a) [3aS-[1(E),3aα,6α,7aβ]]-1-[3-Flouro-4-methoxyphenyl)-1-oxo-2-propenyl]-hexahydro-8,8-dimethyl-3H-3a,6-methano-2,1-benzisothiazole-2,2-dioxide Prepared according to the method of Example 19, step (f) using (E)-3-(3-fluoro-4-methoxyphenyl)-2-propenoic acid.

MS (APCI) 394 (M+H$^+$, 100%)

b) [3aS-[1(1S*,2S*),3aa,6a,7ab]]-1-[[2-(3-Flouro-4-methoxyphenyl)cyclopropyl]carbonyl]-hexahydro-8,8-dimethyl-3H-3a,6-methano-2,1-benzisothiazole-2,2-dioxide Prepared according to the method of Example 19, step (g) using the product of step (a).

MS (APCI) 408 (M+H$^+$, 100%)

c) (1R-trans)-2-(3-Fluoro-4-methoxyphenyl)-cyclopropane carboxylic acid

Prepared according to the method of Example 19, step (h) using the product of step (b).

NMR δH (CDCl$_3$) 6.91–6.81 (3H, m), 3.87 (3H, s), 2.58–2.51 (1H, m) 1.86–180 (1H, m), 1.66–1.60 (1H, m), 1.37–1.25 (1H, m).

d) [1R-(trans)]-2-(3-Fluoro-4-methoxyphenyl) cyclopropanamine, [R-(R*,R*)]-2,3-dihydroxybutanedioate (1:1)

Prepared according to the method of Example 20, step (b) using the product of step (c).

NMR δH (d$_6$-DMSO) 7.08–6.91 (3H, m), 3.93 (2H, s), 3.79 (3H, s), 2.67–2.62 (1H, m), 2.14–2.08 (1H, m), 1.23–1.17 (1H, m), 1.11–1.05 (1H, m).

e) [3aR-[3aα,4α,6α(1R*,2S*),6aα]-6-[7-[[2-(3-Flouro-4-methoxyphenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 1, step (a) using the product of step (d).

MS (APCI) 545 (M+H$^+$, 100%)

f) [1R-[1α,2α,3β(1R*,2S*),5β]]-3-[7-[[2-(3-Fluoro-4-methoxyphenyl)cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 1, step (b) using the product of step (e).

MS (APCI) 505 (M+H$^+$, 100%)

NMR δH (d$_6$-DMSO) 9.30 (1H, d), 7.11–6.98 (3H, m), 5.04–4.97 (2H, m), 4.73–4.70 (2H, m), m), 4.46–4.39 (1H, m), 3.89–3.86 (1H, m), 3.81 (3H, s), 3.51–3.45 (2H, m), 3.11–3.09 (1H, m), 3.00–2.85 (2H, m), 2.27–2.20 (1H, m), 2.09–2.06 (2H, m), 1.90–1.83 (1H, m) 1.57–1.47 (3H, m), 1.33–1.27 (1H, m), 0.84 (3H, t).

EXAMPLE 77

[1S-[1α,2α,3β,5β(1S*,2R*)]]-3-(Hydroxymethyl)-5-[7-[[2-(4-methoxy-3-methylphenyl)cyclopropyl]amino]-5-(propylthio)-3H-1,2,3-triazolo[4,5-d]pyrimidin-3-yl]-cyclopentane-1,2-diol a) [3aS-[1(E),3aα,6α,7aβ]]-1-[3-(4-Methoxy-3-methylphenyl)-1-oxo-2-propenyl]-hexahydro-8,8-dimethyl-3H-3a,6-methano-2,1-benzisothiazole-2,2-dioxide Prepared according to the method of Example 19, step (f) using (E)-3-(4-methoxy-3-methylphenyl)-2-propenoic acid.
MS (APCI) 390 (M+H+, 100%)

b) [3aS-[1(1S*,2S*),3aa,6a,7ab]]-1-[[2-(4-Methoxy-3-methylphenyl)cyclopropyl]carbonyl]-hexahydro-8,8-dimethyl-3H-3a,6-methano-2,1-benzisothiazole-2,2-dioxide Prepared according to the method of Example 19, step (g) using the product of step (a).
MS (APCI) 404 (M+H+, 100%)

c) (1R-trans)-2-(4-Methoxy-3-methylphenyl)-cyclopropane carboxylic acid

Prepared according to the method of Example 19, step (h) using the product of step (b).
NMR δH (CDCl₃) 6.94–6.89 (2H, m), 6.74 (1H, d), 3.81 (3H, s), 2.57–2.51 (1H, m), 2.19 (3H, s), 1.85–1.79 (1H, m), 1.63–1.57 (1H, m), 1.38–1.32 (1H, m).

d) (1R-trans)-2-(4-Methoxy-3-methylphenyl)cyclopropanamine, [R-(R*,R*)]-2,3-dihydroxybutanedioate (1:1)

Prepared according to the method of Example 20, step (b) using the product of step (c).
NMR δH (d₆-DMSO) 6.93–6.90 (2H, m), 6.83–6.80 (1H, m), 3.92 (2H, s), 3.74 (3H, s), 2.64–2.59 (1H, m), 2.13–2.07 (4H, m), 1.22–1.16 (1H, m), 1.08–1.01 (1H, m).

e) [3aR-[3aα,4α,6α(1R*,2S*),6aα]-6-[7-[(2-[4-Methoxy-3-methylphenyl]cyclopropyl)amino]-5-(propylthio)-3H-1,2,3-triazolo[4,5-d]pyrimidin-3-yl]-tetrahydro-2,2-dimethyl4H-cyclopenta-1,3-dioxole-4-methanol Prepared according to the method of Example 1, step (a) using the product of step (d).
MS (APCI) 541 (M+H+, 100%)

f) [1S-[1α,2α,3β,5β(1S*,2R*)]]-3-(Hydroxymethyl)-5-[7-[[2-(4-methoxy-3-methylphenyl)cyclopropyl]amino]-5-(propylthio)-3H-1,2,3-triazolo[4,5-d]pyrimidin-3-yl]-cyclopentane-1,2-diol Prepared according to the method of Example 1, step (b) using the product of step (e).
MS (APCI) 501 (M+H+, 100%)
NMR δH (d₆-DMSO) 9.27 (1H, d), 7.04–6.98 (2H, m), 6.83 (1H, d), 5.01–4.97 (2H, m), 4.73–4.71 (2H, m), 4.46–4.42 (1H, m), 3.88 (1H, q), 3.75 (3H, s), 3.51–3.45 (2H, m), 3.09–3.06 (1H, m), 3.02–2.99 (1H, m), 2.91–2.88 (1H, m), 2.27–2.24 (1H, m), 2.14 (3H, s), 2.13–2.03 (2H, m), 1.90–1.81 (1H, m), 1.59–1.53 (2H, m), 1.43–1.41 (1H, m), 1.25–1.22 (1H, m), 0.85 (3H, t).

EXAMPLE 78

[1R-[1a,2a,3b(1R*,2S*),5b]]-3-[7-[[2-(3,4-Dichlorophenyl)cyclopropyl]amino]-5-(propylthio)-3H-1,2,3-triazolo[4,5-d]pyrimidin-3-yl]-5-(hydroxymethyl)-cyclopentene-1,2-diol a) [3aS-[1(E),3aα,6α,7aβ]]-1-[3-(3,4-Dichlorophenyl)-1-oxo-2-propenyl]-hexahydro-8,8-dimethyl-3H-3a,6-methano-2,1-benzisothiazole-2,2-dioxide Prepared according to the method of Example 19, step (f), using (E)-3-(3,4-dichlorophenyl)-2-propenoic acid.
m. p .198–200° C.
MS (APCI) 414 (M+H+, 100%)

b) [3aS-[1(1S*,2S*),3aa,6a,7ab]]-1-[[2-(3,4-Dichlorophenyl)cyclopropyl]carbonyl]-hexahydro-8,8-dimethyl-3H-3a,6-methano-2,1-benzisothiazole-2,2-dioxide Prepared according to the method of Example 19, step (g) using the product of step (a).
m.pt. 162–163° C.
MS (APCI) 429 (M+M+, 100%)

c) (1R-trans)-2-(3,4-Dichlorophenyl)-cyclopropane carboxylic acid

Prepared according to the method of Example 19, step (h) using the product of step (b).
NMR δH (CDCl₃) 7.40–7.30 (2H, m), 7.20 (1H, d), 6.96–6.93 (1H, dd), 2.57–2.51 (1H, m), 1.92–1.85 (1H, m), 1.71–1.65 (1H, m), 1.41–1.34 (1H, m).

d) (1R-trans)-2-(3,4-Dichlorophenyl)cyclopropanamine, [R-(R*,R*)]-2,3-dihydroxybutanedioate (1:1)

Prepared according to the method of Example 20, step (b) using the product of step (c).
NMR δH (d₆-DMSO) 7.53–7.51 (1H, d), 7.41–7.40 (1H, d), 7.14–7.11 (1H, dd) 3.77 (2H, s), 2.73–2.68 (1H, m), 2.16–2.10 (1H, m), 1.27–1.14 (2H, m).

e) [3aR-[3aα,4α,6α(1R*,2S*),6aα]-6-[7-[[2-(3,4-Dichlorophenyl)cyclopropyl]amino]-tetrahydro-2,2-dimethyl-5-(propylthio)-3H-1,2,3-triazolo[4,5-d]pyrimidin-3-yl]-4H-cyclopenta-1,3-dioxole-4-methanol Prepared according to the method of Example 1, step (a) using the product of step (d).
MS (APCI) 565 (M+H+, 100%)
NMR δH (CDCl₃) 7.40–7.33 (2H, m), 7.20–7.01 (1H, m), 5.21–5.15 (2H, m), 4.73–4.70 (1H, m), 3.80–3.75 (2H, m), 3.20–3.00 (3H, m), 2.61–2.34 (4H, m), 2.21–2.09 (1H, m) 2.03–1.93 (1H, m), 1.75–1.61 (1H, m), 1.58 (3H, s), 1.45–1.35 (2H, m), 1.28 (3H, s), 1.05–0.82 (4H, m).

f) [1R-[1a,2a,3b(1R*,2S*),5b]]-3-[7-[[2-(3,4-Dichlorophenyl)cyclopropyl]amino]-5-(propylthio)-3H-1,2,-triazolo[4,5-d]pyrimidin-3-yl]-5-(hydroxymethyl)-cyclopentane-1,2-diol Prepared according to the method of Example 1, step (b) using the product of step (e).

MS (APCI) 526 (M+H⁺, 100%)

NMR δH (d₆-DMSO) 9.38–9.36 (1H, d), 7.55–7.52 (2H, m), 7.22–7.19 (1H, dd), 5.01–4.70 (2H, m), 4.72–4.70 (2H, m), 4.42–4.40 (1H, m), 3.90–3.85 (1H, m), 3.50–3.40 (2H, m), 3.20–3.16 (1H, m), 3.02–2.70 (2H, m), 2.71–2.43 (1H, m), 2.14–2.09 (1H, m), 2.18–2.03 (1H, m), 1.90–1.81 (1H, m), 1.90–1.41 (4H, m), 0.80 (3H, t).

EXAMPLE 79

1S-[1α,2α,3β,5β(1S*,2R*)]-3-[(2-Amino)ethoxy]-5-[7-(2-phenylcyclopropyl)amino]-5-propylthio-3H-[1,2,3]-triazolo[4,5-d]pyrimidin-3-yl]-cyclopentane-1,2-diol.

To a solution of the product from Example 23 (0.50 g) in tetrahydrofuran (20 ml) was added diborane (10 ml, 1M solution in THF). The reaction was refluxed for 1 hour, cooled and methanol (5 ml) added. The solvent was evaporated and the residue dissolved in methanol (25 ml)/conc. hydrochloric acid (0.50 ml) then heated at reflux for 1 hour. The solvent was evaporated and the residue purified (HPLC, Nova-pak® C18 column, 0.1% aqueous trifluoroacetic acid-:methanol 50:50) to give the title compound (198 mg).

MS (APCI) 486 (M+H⁺, 100%)

NMR δH (d₆-DMSO) 9.37 (1H, d, J=4.2 Hz), 7.83 (3H, s), 7.29 (2H, m), 7.16 (3H, m), 4.96 (1H, q, J=8.7 Hz), 4.57–4.53 (1H, m), 4.00 (1H, m), 3.66 (2H, m), 3.21 (1H, m), 3.03 (2H, m), 3.01–3.92 (2H, m), 2.82 (1H, m), 2.10 (1H, m), 2.05 (1H, m), 1.55–1.44 (3H, m), 1.32 (1H, q, J=7.8 Hz), 0.80 (3H, t, J=7.5 Hz).

EXAMPLE 80

[1R-(1α,2α,3β(1R*,2S*),5β)]-3-[7-[[2-(3,4-Dimethylphenyl)cyclopropyl]amino]-5-(propylthio)-3H-1,2,3-triazolo[4,5-d]pyrimidin-3-yl]-5-(hydroxymethyl)-cyclopentane-1,2-diol a) 3-(3,4-Dimethylphenyl)prop-2-enoic acid

Prepared according to the method of example 64, step (a), using 3,4-dimethyl-benzaldehyde.

MS (APCI) 175 (M–H⁺, 100%)

b) [3aS-[1(E),3aα,6α,7aβ]]-1-[3-(3,4-Dimethylphenyl)-1-oxo-2-propenyl]-hexahydro-8,8-dimethyl-3H-3a,6-methano-2,1-benzisothiazol-2,2-dioxide The subtitle compound was prepared according to the method of Example 19, step (f) using the product from step (a).

MS (APCI) 374 (M+H⁺, 100%).

c) [3aS-[1(1S*,2S*),3aα,6α,7aβ]]-1-[[2-(3,4-Dimethylphenyl)cyclopropyl]carbonyl]-hexahydro-8,8-dimethyl-3H-3a,6-methano-2,1-benzisothiazole-2,2-dioxide The subtitle compound was prepared according to the method of Example 19, step (g) using the product of step (b).

MS (APCI) 388 (M–H⁺, 100%)

d) (1R-trans)-2-(3,4-Dimethylphenyl)cyclopropanecarboxylic acid

The subtitle compound was prepared according to the method of Example 19, step (h) using the product of step (c).

MS (APCI) 189 (M–H⁺, 100%)

e) (1R-trans)-2-(3,4-Dimethylphenyl)cyclopropanamine, [R-(R*,R*)]-2,3-dihydroxybutanedioate (1:1)

The subtitle compound was prepared according to the method of Example 20, step (b) using the product of step (d).

NMR δH (d₆-DMSO) 7.03–7.01 (1H, m), 6.88 (1H, s), 6.8–6.81 (1H, m), 3.92 (2H, s), 2.67–2.61 (1H, m), 2.18 (3H, s), 2.16 (3H, s), 2.13–2.06 (1H, m), 1.24–1.17 (1H, m), 1.10–1.03 (1H, m).

f) [1R-(1α,2α,3β(1R*,2S*),5β)]-3-[7-[[2-(3,4-Dimethylphenyl)cyclopropyl]amino]-5-(propylthio)-3H-1,2,3-triazolo[4,5-d]pyrimidin-3-yl]-5-hydroxymethyl)-cyclopentane-1,2-diol The title compound was prepared according to the method of Example 1, step (a), using the products of step (e), followed by the method of example 1 step (b).

MS (APCI) 485 (M+H⁺, 100%)

NMR δH (d₆-DMSO) 9.29–9.28 (1H, d), 7.04–7.01 (2H, m), 6.91–6.88 (1H, m), 5.01 (2H, m), 4.73–4.70 (2H, m), 4.43–4.41 (1H, m), 3.88–3.86 (1H, m), 3.51–3.45 (2H, m), 3.13–3.11 (1H, m), 2.98–2.85 (2H, m), 2.26–2.21 (1H, m), 2.20 (3H, s), 2.17 (3H, s), 2.08–2.04 (2H, m), 1.91–1.82 (1H, m), 1.53–1.42 (2H, m), 1.27–1.23 (1H, m), 0.85–0.80 (3H, s).

EXAMPLE 81

[1S-[1α,2β,3β,4α(1S*,2R*)]]-4-[7-[[2-(3,4-Dimethylphenyl)cyclopropyl]amino]-5-(propylthio)-3H-1,2,3-triazolo[4,5-d]pyrimidin-3-yl]-cyclopentane-1,2,3-triol a) [3aR-[3aα,4α,6α(1R*,2S*),6aα]]-6-[7-[2-[(3,4-Dimethylphenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of example 1, step (a) using the product from example 24, step (d) and the product of example 80, step (e).

MS (APCI) 511 (M+H⁺, 100%)

b) [1S-[1α,2β,3β,4α(1S*,2R*)]]-4-[7-[[2-(3,4-Dimethylphenyl)cyclopropyl]amino]-5-(propylthio)-3H-1,2,3-triazolo[4,5-d]pyrimidin-3-yl]-cyclopentane-1,2,3-triol The title compound was prepared according to the method of example 1, step (b) using the product of step (a).

M.p. 175–176° C.

MS (APCI) 471 (M+H⁺, 100%)

NMR δH (d₆-DMSO) 9.29 (1H, d), 7.03–6.87 (3H, m), 5.09(1H, d), 5.02 (1H,d), 4.95 (1H, d), 4.90 (1H, d), 4.68 (1H, m), 3.93 (1H, m), 3.77 (1H, m), 3.13 (1H,m) 3.01–2.81 (2H, m), 2.61 (1H, m), 2.19 (3H, s), 2.16 (3H, s), 2.06 (1H, m) 1.90 (1H, m), 1.52–1.42 (2H,m,), 1.43 (1H, m), 1.26 (1H, m) 0.81 (3H, t).

EXAMPLE 82

[1R-(1α,2β,3α,5β)]-3-[7-(Cyclopropylamino)-5-[[4-(trifluoromethyl)phenyl]thio]-3H-1,2,3-triazolo[4,5-d]pyrimidin-3yl]-5-(hydroxymethyl)-cyclopentane-1,2-diol a) [3aR-(3aα,4α,6α,6aα)]-6-[7-(Cyclopropylamino)-5-(propylsulfonyl)-3H-1,2,3-triazolo [4,5-d]pyrimidin-3yl]-tetrahydro-2,2-dimethyl-4H-cyclopenta-1,3-dioxole-4-methanol Prepared by the method of example 4, step (a) using the product of Example 2, step (a).

MS (APCI) 453 (M+H⁺, 100%)

b) [3aR-(3aα,4α,6α,6aα)]-6-[7-(Cyclopropylamino)-5-[[4-(trifluoromethyl)phenyl]thio]-3H-1,2,3-triazolo[4,5-d]pyrimidin-3-yl]-tetrahydro-2,2-dimethyl-4H-cyclopenta-1,3-dioxole-4-methanol Prepared by the method of example 4, step (b) using the product of step (a).

MS (APCI) 523 (M+H⁺, 100%)

c) [1R-(1α,2α,3β,5β)]-3-[7-(Cyclopropylamino)-5-[[4-(trifluoromethyl)phenyl]thio]-3H-1,2,3-triazolo[4,5-d]pyrimidin-3-yl]-5-(hydroxymethyl)-cyclopentane-1,2-diol Prepared by the method of example 1, step (b) using the product of step (b).

MS (APCI) 483 (M+H⁺, 100%)

NMR δH (d₆-DMSO) 9.23 (1H, d), 7.90 (2H, d),7.70 (2H, d), 4.95–4.90 (2H, m), 4.67–4.60 (2H, m), 4.32–4.30 (1H, m), 3.72–3.70 (1H, m), 3.32 (2H, m), 2.81–2.79 (1H, m), 2.22–2.16 (1H, m), 2.05–2.00 (1H, m),1.80–1.60 (1H, m),1.00–0.60 (2H, m).

EXAMPLE 83

[1S-[1α,2β,3β,4α(1S*,2R*)]]-4-[7-[[2-(3,5-Dichlorophenyl)cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-(3,5-Dichlorophenyl)-1-oxo-2-propenyl]-hexahydro-8,8-dimethyl-3H-3a,6-methano-2,1-benzisothiazole-2,2-dioxide The subtitle compound was prepared according to the method of example 19, step (f) using 3-(3,5-dichlorophenyl)-2-propenoic acid.

MS (APCI) 414/416/418 (M+H⁺), 153 (100%)

b) [3aS-[1(1S*,2S*),3aα,6α,7aβ]]-1-[[2-(3,5-Dichlorophenyl)cyclopropyl]carbonyl]-hexahydro-8,8-dimethyl-3H-3a,6-methano-2,1-benzisothiazole-2,2-dioxide The subtitle compound was prepared according to the method of example 19, step (g) using he product of step (a).

MS (APCI) 428/430/432 (M+H⁺), 364 (100%)

c) (1R-trans)-2-(3,5-Dichlorophenyl)-cyclopropanecarboxylic acid

The subtitle compound was prepared according to the method of example 19, step (h) using the product of step (b).

NMR δH (CDCl₃) 1.26–1.42 (1H, m), 1.65–1.72 (1H, m), 1.89–1.95 (1H, m), 2.51–2.58 (1H, m), 6.99 (2H, d, J=1.8 Hz), 7.22 (1H, t, J=1.8 Hz)

d) (1R-trans)-2-(3,5-Dichlorophenyl) cyclopropanamine, [R-(R*,R*)]-2,3-dihydroxybutanedioate (1:1)

The subtitle compound was prepared according to the method of example 20, step (b) using the product of step (c).

NMR δH (d₆-DMSO) 1.19–1.29 (2H, m), 2.13–2.20 (1H, m), 2.71–2.81 (1H, m), 4.00 (2H, s), 7.22 (2H, d, J=1.8 Hz), 7.40 (1H, t, J=1.8 Hz)

e) [1S-[1α,2β,3β,4α(1S*,2R*)]]-4-[7-[[2-(3,5-Dichlorophenyl)cyclopropyl]amino]-5-(propylthio)-3H-1,2,3-triazolo[4,5-d]pyrimidin-3yl]-cyclopentane-1,2,3-triol The title compound was prepared according to the method of example 24, step (f) using the products of step (d) and example 24, step (d).

MS (APCI) 511/513/515 (M+H⁺), 511 (100%)

NMR δH (d₆-DMSO) 9.39 (1H, d, J=4.2 Hz), 7.40 (1H, t, J=1.8 Hz), 7.30 (2H, d, J=1.8 Hz), 5.11–4.91 (4H, m), 4.68–4.62 (1H, m), 3.93 (1H, br s), 3.78 (1H, br s), 3.20 (1H, br s), 2.99–2.78 (2H, m), 2.64–2.54 (1H, m), 2.17–2.10 (1H, m), 1.95–1.85 (1H, m), 1.62–1.45 (4H, m), 0.81 (3H, t, J=7.2 Hz),

EXAMPLE 84

[1R-[1α(1S*,2R*),2β,3β,4α]]-N-[3-[2-[[3-(2,3,4-Trihydroxy-cyclopentyl)-5-(propylthio)-3H-1,2,3-triazolo[4,5-d]pyrimidin-7-yl]amino]cyclopropyl]phenyl]-methanesulfonamide a) (1R-trans)-N-[2-(3-Nitrophenyl)cyclopropyl]-carbamic acid,1,1-dimethylethyl ester A solution of the acid from example 27 step (a) (1.72 g), diphenylphosphoryl azide (2.1 ml) and triethylamine (1.4 ml) in tert-butanol (15 ml) and toluene (35 ml) was heated at 85° C. for 5 hours. Water was added and the mixture was extracted with ether. The organic layers were dried, evaporated and purified (SiO₂, petrol:ether 1:1 as eluent) to give the subtitle compound as a colourless solid (1.91 g).

NMR δH (CDCl₃) 8.03 (1H, d), 7.98–7.95 (1H, m), 7.55–7.50 (1H, m), 7.43 (1H, t), 4.83 (1H, s), 2.78–2.75 (1H, m), 2.21–2.12 (1H, m), 1.46 (9H, s), 1.29–1.23 (2H, m).

b) (1R-trans)-N-[2-(3-Aminophenyl)cyclopropyl]-carbamic acid,1,1-dimethylethyl ester A suspension of platinum on charcoal (5%, 374 mg) and the product from step (a) (1.90 g) in ethanol (40 ml) was stirred under 1.1 atmospheres pressure of hydrogen for 4 hours. The mixture was filtered and purified (SiO₂, isohexane:ether, 1:3 as eluent) to give the subtitle compound (1.60 g).

NMR δH (CDCl₃) 7.04 (1H, t), 6.53–6.45 (3H, m), 4.81 (1H, s), 3.61 (2H, s), 2.72–2.70 (1H, m), 1.98–1.91 (1H, m), 1.46 (9H, s), 1.19–1.06 (2H, m).

c) (1R-trans)-N-[2-[3-[(Methylsulfonyl)amino]-phenyl]cyclopropyl]-carbamic acid,1,1-dimethylethyl ester A solution of the product from step (b) (592 mg), methanesulfonyl chloride (0.225 ml) and pyridine (0.35 ml) in dichloromethane (5 ml) was stirred for 3 hours. Water was added and the mixture extracted with dichloromethane. The organic layers were dried, evaporated and purified (SiO₂, isohexane:ether, 1:3 as eluent) to give the subtitle compound (724 mg).

MS (APCI) 325 (M−H⁻, 100%)

d) (1S-trans)-N-3-[(2-Aminocyclopropyl)phenyl]-methanesulfonamide, [R-(R*,R*)]-2,3-dihydroxybutanedioate (1:1)

A solution of the product from step (c) (722 mg) in trifluoroacetic acid (3 ml) was stirred for 3 hours. The solvent was removed in vacuo and the residue basified with sodium bicarbonate solution and extracted with ethyl acetate. The organic layers were dried and evaporated. The resulting amine was dissolved in ethanol (10 ml) and a solution of L-tartaric acid (332 mg) in ethanol (20 ml) was added. The solvent was removed in vacuo to give the subtitle compound (867 mg).

NMR δH (d$_6$-DMSO) 7.30–6.81 (4H, m), 4.05 (2H, s), 2.97 (3H, s), 2.74–2.70 (1H, m), 2.23–2.18 (1H, m), 1.34–1.27 (1H, m), 1.17–1.05 (1H, m).

e) [3aS-[3aα,4α(1R*,2S*),6α,6aα]-N-[3-[2-[[3-(2,2-Dimethyl-6-hydroxy-tetrahydro-4H-cyclopenta-1,3-dioxol-4-yl)-5-(propylthio)-3H-1,2,3-triazolo[4,5-d]pyrimidin-7-yl]amino]cyclopropyl]-phenyl]-methanesulfonamide The subtitle compound was prepared according to the method of Example 1, step (a) using the products of step (b) and Example 24, step (d).

MS (APCI) 576 (M+H$^+$, 100%), f) [1R-[1α(1S*,2R*),2β,3β,4α]]-N-[3-[2-[[3-(2,3,4-Trihydroxy-cyclopentyl)-5-propylthio)-3H-1,2,3-triazolo[4,5-d]pyrimidin-7-yl]amino]cyclopropyl]phenyl]-methanesulfonamide Prepared according to the method of Example 1, step (b) using the product of step (e)

m.p. 170–2° C.

MS (APCI) 536 (M+H$^+$, 100%),

NMR δH (d$_6$-DMSO) 9.67 (1H, s), 9.34 (1H, d), 7.25 (1H, t), 7.06–6.98 (2H, m) 6.92 (1H, d), 5.11 (1H, d), 5.04–4.98 (1H, m), 4.94–4.91 (2H, m), 4.68–4.61 (1H, m), 3.95–3.90 (1H, m), 3.80–3.75 (1H, m), 3.24–3.20 (1H, m), 2.98 (3H, s), 2.97–2.85 (2H, m), 2.62–2.57 (1H, m), 2.18–2.06 (1H, m), 1.97–1.87 (1H, m), 1.54–1.22 (4H, m), 0.82 (3H, t).

EXAMPLE 85

[1S-[1α,2β,3β,4α(1S*,2R*)]]-4-[7-[[2-(3,4-Dimethoxyphenyl)cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-(3,4-Dimethoxyphenyl)-1-oxo-2-propenyl]-hexahydro-8,8-dimethyl-3H-3a,6-methano-2,1-benzisothiazole-2,2-dioxide The subtitle compound was prepared according to the method of example 19, step (f) using 3-(3,4-dimethoxyphenyl)-2-propenoic acid

MS (APCI) (M+H$^+$), 153 (100%)

b) [3aS-[1(1S*,2S*),3aα,6α,7aβ]]-1-[[2-(3,4-Dimethoxyphenyl)cyclopropyl]carbonyl]-hexahydro-8,8-dimethyl-3H-3a,6-methano-2,1-benzisothiazole-2,2-dioxide The subtitle compound was prepared according to the method of example 19, step (g) using the product of step (a).

MS (APCI) 420 (M+H$^+$, 100%)

c) (1R-trans)-2-(3,4-Dimethoxyphenyl)-cyclopropanecarboxylic acid

The subtitle compound was prepared according to the method of example 19, step (h) using the product of step (b).

NMR δH (CDCl$_3$) 1.34–1.41 (1H, m), 1.60–1.66 (1H, m), 1.83–1.88 (1H, m), 2.54–2.61 (1H, m), 3.86 (3H, s), 3.88 (3H, s), 6.65–6.67 (2H, m), 6.79 (1H, d, J=8.7 Hz)

d) (1R-trans)-2-(3,4-Dimethoxyphenyl) cyclopropanamine, [R-(R*,R*)]-2,3-dihydroxybutanedioate (1:1)

The subtitle compound was prepared according to the method of example 20, step (b) using the product of step (c).

NMR δH (d$_6$-DMSO) 1.03–1.22 (2H, m), 2.08–2.14 (1H, m), 2.63–2.68 (1H, m), 3.70 (3H, s), 3.74 (3H, s), 3.91 (2H, s), 6.23 (1H, dd, J=8.1 Hz, J'=1.8 Hz), 6.70 (1H, d, J=1.8 Hz), 6.84 (1H, d, J=8.1 Hz)

e) [1S-[1α,2β,3β,4α(1S*,2R*)]]-4-[7-[[2-(3,4-Dimethoxyphenyl)cyclopropyl]amino]-5-(propylthio)-3H-1,2,3-triazolo[4,5-d]pyrimidin-3-yl]-cyclopentane-1,2,3-triol The title compound was prepared according to the method of example 24, step (f) using the products of step (d) and example 24, step (d).

MS (APCI) 503 (M+H$^+$, 100%)

NMR δH (d$_6$-DMSO) 9.28 (1H, d, J=4.5 Hz), 6.86 (1H, d, J=8.4 Hz), 6.81 (1H, d, J=2.1 Hz), 6.70 (1H, dd, J=8.4 Hz, J'=2.1 Hz), 5.10–4.90 (4H, m), 4.68–4.64 (1H, m), 3.93 (1H, s), 3.76 (3H, s), 3.74 (1H, s), 3.71 (3H, s), 3.13–3.10 (1H, m), 3.05–2.82 (2.65–2.55 (1H, m), 2.10–2.00 (1H, m), 1.95–1.85 (1H, m), 1.56–1.27 (4H, m), 0.82 (3H, t, J=7.2 Hz).

EXAMPLE 86

[1S-[1α,2β,3β,4α(1S*,2R*)]]-4-[7-[[2-(4-Methoxy-3-methylphenyl)cyclopropyl]amino]-5-(propylthio)-3H-1,2,3-triazolo[4,5-d]pyrimidin-3-yl]-cyclopentane-1,2,3triol a) [3aR-[3aα,4α,6α(1R*,2S*),6aα]]-Tetrahydro-6-[7-[2-[(4-methoxy-3-methylphenyl)cyclopropyl]amino]-5-(propylthio)-3H-1,2,3-triazolo[4,5-d]pyrimidin-3-yl]-2,2-dimethyl-4H-cyclopenta-1,3-dioxol-4-ol The subtitle compound was prepared according to the method of example 1, step (a) using the products from example 24, step (d) and example 77, step (d).

MS (APCI) 527 (M+H$^+$, 100%)

b) [1S-[1α,2β,3β,4α(1S*,2R*)]]-4-[7-[[2-(4-Methoxy-3-methylphenyl)cyclopropyl]amino]-5-(propylthio)-3H-1,2,3-triazolo[4,5-d]pyrimidin-3-yl]-cyclopentane-1,2,3-triol The title compound was prepared according to the method of example 1, step (b) using the product of step (a).

M.p. 135–136° C.

MS (APCI) 487 (M+H$^+$, 100%)

NMR δH (d$_6$-DMSO) 9.28 (1H, d), 7.01–6.80 (3H, m), 5.09(1H, d), 5.01 (1H,d), 4.98 (1H, d), 4.90 (1H, d), 4.66 (1H, m), 3.91 (1H, m), 3.76 (1H, m), 3.73 (3H, s), 3.06 (1H,m) 3.01–2.81 (2H, m), 2.58 (1H, m), 2.12 (3H, s), 2.02 (1H, m) 1.88 (1H, m), 1.56–1.49 (2H, m,), 1.42 (1H, m), 1.23 (1H, m) 0.80 (3H, t).

EXAMPLE 87

[1R-[1α(1S*,2R*),2β,3β,4α]]-N-[3-[2-[[3-(2,3,4-Trihydroxy-cyclopentyl)-5-(propylthio)-3H-1,2,3-triazolo[4,5-d]pyrimidin-7-yl]amino]cyclopropyl]phenyl]-acetamide a) (1R-trans)-N-[2-(3-Acetamidophenyl) cyclopropyl]-carbamic acid,1,1-dimethylethyl ester A solution of the product from Example 84, step (b) (582 mg), acetic anhydride (0.27 ml) and pyridine (0.35 ml) in dichloromethane (5 ml) was stirred for 18 hours. Water was added and the mixture was extracted with dichloromethane. The organic layers were dried, evaporated and purified (SiO$_2$, isohexane:acetone, 2:1 as eluent) to give the subtitle compound (703 mg).

MS (APCI) 325 (M–H$^+$, 100%)

b) (1S-trans)-N-4-[(2-Aminocyclopropyl)phenyl]-acetamide, [R-(R*,R*)]-2,3-dihydroxybutanedioate (1:1)

A solution of the product from step (a) (703 mg) in trifluoroacetic acid (3 ml) was stirred for 3 hours. The solvent was removed in vacuo and the residue basified with sodium bicarbonate solution then extracted with ethyl acetate. The organic layers were dried and evaporated. The amine was dissolved in ethanol (10 ml) and a solution of L-tartaric acid (349 mg) in ethanol (25 ml) was added. The solvent was removed in vacuo to give the subtitle compound (828 mg).

NMR δH (d$_6$-DMSO) 7.45–7.05 (3H, m), 6.82 (1H, d), 4.19 (2H, s), 2.77–2.71 (1H, m), 2.30–2.23 (1H, m), 2.03 (3H, s), 1.39–1.31 (1H, m), 1.18–1.08 (1H, m).

c) [3aS-[3aα,4α(1R*,2S*),6α,6aα]]-N-[3-[2-[[3-(2,2-Dimethyl-6-hydroxy-tetrahydro-4H-cyclopenta-1,3-dioxol-4-yl)-5-(propylthio)-3H-1,2,3-triazolo[4,5-d]pyrimidin-7-yl]amino]cyclopropyl]phenyl]-acetamide Prepared according to the method of Example 12, step (e) using the product of step (b).

d) [1R-[1α(1S*,2R*),2β,3β,4α]]-N-[3-[2-[[3-(2,3,4-Trihydroxy-cyclopentyl)-5-(propylthio)-3H-1,2,3-triazolo[4,5-d]pyrimidin-7-yl]amino]cyclopropyl]phenyl]-acetamide Prepared according to the method of Example 1, step (b) using the product of step (c).

m.p. 147–8° C.

MS (APCI) 500 (M+H$^+$, 100%),

NMR δH (d$_6$-DMSO) 9.87 (1H, s), 9.35 (1H, d), 7.41–7.34 (2H, m), 7.18 (1H, t), 6.84 (1H, d), 5.13–4.91 (4H, m), 4.66–4.61 (1H, m), 3.93–3.91 (1H, m), 3.82–3.75 (1H, m), 3.23–2.78 (4H, m), 2.62–2.51 (1H, m), 2.17–2.08 (1H, m), 2.02 (3H, s), 1.97–1.85 (1H, m), 1.72–1.61 (1H, m), 1.57–1.09 (3H, m), 0.80 (3H, t).

EXAMPLE 88

[1S-[1α,2β,3β,4α(1S*,2R*)]]-4-[7-[[(2-(3,4-Dichlorophenyl)cyclopropyl]amino]-5-(propylthio)-3H-1,2,3-triazolo[4,5-d]pyrimidin-3-yl]-cyclopentane-1,2,3-triol a) [3aR-[3aα,4α,6α(1R*,2S*),6aα]]-6-[7-[2-[(3,4-Dichlorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of Example 1, step (a) using the products of Example 24, step (d) and Example 78, step (d).

MS (APCI) 551 (M+H$^+$, 100%)

b) 1S-[1α,2β,3β,4α(1S*,2R*)]]-4-[7-[[(2-(3,4-Dichlorophenyl)cyclopropyl]amino]-5-(propylthio)-3H-1,2,3-triazolo[4,5-d]pyrimidin-3-yl]-cyclopentane-1,2,3-triol Prepared according to the method of Example 1, step (b) using the product of step (a).

m.p. 140–2° C.

MS (APCI) 511 (M+H$^+$, 100%),

NMR δH (d$_6$-DMSO) 9.4 (1H, d), 7.54–7.50 (2H, m), 7.18 (1H, dd), 5.13–4.91 (4H, m), 4.68–4.60 (1H, m), 3.94–3.90 (1H, m), 3.78–3.75 (1H, m), 3.18–3.02 (1H, m), 2.91–2.76 (2H, m), 2.62–2.51 (1H, m), 2.17–2.06 (1H, m), 1.94–1.84 (1H, m), 1.71–1.37 (3H, m), 0.79 (3H, t).

EXAMPLE 89

[1S-[1α,2β,3β,4α(1S*,2R*)]]-[4-7-[[2-(4-Chloro-3-methylphenyl)cyclopropyl]amino]-5-(propylthio)-3H-1,2,3-triazolo[4,5-d]pyrimidin-3-yl]-cyclopentane-1,2,3-triol a) 3-(4-Chloro-3-methylphenyl)-2-propenoic acid The subtitle compound was prepared according to the method of Example 64, step (a) using (4-chloro-3-methyl) benzaldehyde (prepared according to WO 9603387).

MS (APCI) 191 (M–H$^+$, 100%)

b) [3aS-[1(E),3aα,6α,7aβ]]-1-[3-(4-Chloro-3-methylphenyl)-1-oxo-2-propenyl]-hexahydro-8,8-dimethyl-3H-3a,6-methano-2,1-benzisothiazole-2,2-dioxide The subtitle compound was prepared according to the method of Example 19, step (f) using the product of step (a).

MS (APCI) 392 (M–H$^+$, 100%)

c) [3aS-[1(1S*,2S*),3aα,6α,7aβ]]-1-[[2-(4-Chloro-3-methylphenyl)cyclopropyl]carbonyl]-hexahydro-8,8-dimethyl-3H-3a,6-methano-2,1-benzisothiazole-2,2-dioxide The subtitle compound was prepared according to the method of Example 19, step (g) using the product of step (b).

NMR δH (CDCl$_3$) 7.22 (1H, d, J=8.1 Hz), 7.07 (1H, d, J=1.9 Hz), 6.96 (1H, dd, J=8.1, J=2.1 Hz), 3.92 (1H, dd, J=7.5, J=5.0 Hz), 3.51 (1H, d, J=13.8 Hz), 3.44 (1H, d, J=13.8 Hz), 2.33 (3H, s), 2.57–2.47 (2H, m) 2.20–2.02 (2H, m), 1.98–1.82 (3H, m), 1.79–1.73 (1H, m), 1.44–1.29 (3H, m), 1.20 (3H, s), 0.98 (3H, s).

d) (1R-trans)-2-(4-Chloro-3-methylphenyl) cyclopropanecarboxylic acid

The subtitle compound was prepared according to the method of Example 19, step (h) using the product of step (c).

NMR δH (CDCl$_3$) 7.24 (1H, d, J=8.3 Hz), 6.97 (1H, d, J=1.5 Hz), 6.86 (1H, dd, J=8.1, J=1.9 Hz), 2.54 (1H, ddd, J=10.6, J=6.7, J=4.2 Hz), 2.34 (3H, s), 1.86 (1H, ddd, J=9.2, J=5.2, J=4.2 Hz), 1.65 (1H, dt, J=9.2, J=4.8 Hz), 1.37 (1H, ddd, J=11.3, J=6.7, J=4.8 Hz).

e) (1R-trans)-2-(4-Chloro-3-methylphenyl) cyclopropanamine, [R-(R*,R*)]-2,3-dihydroxybutanedioate (1:1)

The subtitle compound was prepared according to the method of Example 20, step (b) using the product of step (d).

MS (APCI) 182/184 (M+H$^+$), 182 (100%)

f) [1S-[1α,2β,3β,4α(1S*,2R*)]]-4-[7-[[2-(4-Chloro-3methylphenyl)cyclopropyl]amino]-5-(propylthio)-3H-1,2,3-triazolo[4,5-d]pyrimidin-3-yl]-cyclopentane-1,2,3-triol The title compound was prepared according to the method of Example 24, step (f) using the products of step (e) and Example 24, step (d).

MS (APCI) 491/493 (M+H$^+$), 491 (100%)

NMR δH (d$_6$-DMSO) 9.35 (1H, d, J=3.9 Hz), 7.30 (1H, d, J=8.1 Hz), 7.22 (1H, d, J=2.1 Hz), 7.04 (1H, dd, J=8.1, J=2.1 Hz), 5.11 (1H, d, J=4.2 Hz), 5.02 (1H, d, J=6.6 Hz), 4.95 (1H, q, J=8.7 Hz), 4.92 (1H, d, J=4.2 Hz), 4.69–4.64 (1H, m), 3.97–3.90 (1H, m), 3.81–3.75 (1H, m), 3.20–2.79 (3H, m), 2.62–2.50 (1H, m), 2.31 (3H, s), 2.26–2.03 (1H, m), 1.97–1.83 (1H, m), 1.75–1.33 (4H, m), 0.80 (3H, t, J=7.5 Hz).

EXAMPLE 90

[1S-[1α,2β,3β,4α(trans)]]-4-[7-[[2-(Phenylmethyl)cyclopropyl]amino]-5-(propylthio)-3H-1,2,3-triazolo[4,5-d]pyrimidin-3-yl]-cyclopentane-1,2,3-triol a) (trans)-2-(Phenylmethyl)-cyclopropanecarboxylic acid Prepared according to the method of Example 20, step (a) using 2-(phenylmethyl)cyclopropanecarboxylic acid, ethyl ester.

MS (APCI) 175 (M–H$^+$, 100%)

b) (trans)-2-(3-Phenylmethyl)cyclopropanamine

Prepared according to the method of Example 19, step (i) using the product from step (a).

NMR δH (CDCl$_3$) 7.33–7.17 (5H, m), 2.55 (2H, d), 2.53–2.18 (1H, m), 1.03–0.96 (1H, m), 0.60–0.54 (1H, m), 0.45 (1H, m).

c) [1S-[1α,2β,3β,4α(trans)]]-4-[7-[[2-(Phenylmethyl)cyclopropyl]amino]-5-propylthio)-3H-1,2,3-triazolo[4,5-d]pyrimidin-3-yl]-cyclopentane-1,2,3-triol Prepared according to the method of Example 24, step (f) using the product from step (b) and the product from Example 24, step (d).

NMR δH (d$_6$-DMSO) 9.10–9.08 (1H, m), 7.35–7.27 (4H, m), 7.21–7.17 (1H, m), 5.11–5.10 (1H, m), 5.03–5.01 (1H, m), 4.97–4.91 (2H, m), 4.69–4.64 (1H, m), 3.94 (1H, s), 3.79 (1H, s), 3.20–3.06 (3H, m), 2.78–2.76 (1H, m), 2.60–2.52 (2H, m), 1.97–1.92 (1H, m), 1.76–1.66 (2H, m), 1.37–1.32 (1H, m), 0.99 (3H, t), 0.78–0.76 (1H, m).

MS (APCI) 457 (M+H$^+$, 100%)

EXAMPLE 91

[1R-[1α,2α,3β(1R*,2S*),5β]]-3-[7-[[2-(4-Chloro-3-methylphenyl)cyclopropyl]amino]-5-(propylthio)-3H-1,2,3-triazolo[4,5-d]pyrimidin-3-yl]-5-(hydroxymethyl)-cyclopentane-1,2-diol a) [3aR-3aα,4α,6α(1R*,2S*),6aα]-6-[7-[[2-(4-Chloro-3-methylphenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 1, step (a) using the product of example 89, step (e).

MS (APCI) 545, 547 (M+H$^+$), 545 (100%).

b) [1R-[1α,2α,3β(1R*,2S*),5β]]-3-[7-[[2-(4-Chloro-3-methylphenyl)cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 1, step (b) using the product of step (a).

MS (APCI) 505, 507 (M+H$^+$), 505 (100%).

NMR δH (d$_6$-DMSO) 9.33 (1H, d), 7.31–7.02 (3H, m), 5.00 (1H, q), 4.42 (1H, q), 3.89–3.86 (1H, m), 3.53–3.42 (2H, m), 3.16–3.12 (1H, m), 2.98–2.82 (2H, m), 2.31 (3H, s), 2.27–2.20 (1H, m), 2.10–2.06 (2H, m), 1.89–1.79 (1H, m), 1.54–1.45 (3H, m), 1.37–1.31 (1H, m), 0.82 (3H, t).

EXAMPLE 92

[1S-[1α,2β,3β,4α(1S*,2R*)]]-4-[7-[[2-(3-Dimethylaminophenyl)cyclopropyl]amino]-5-(propylthio)-3H-1,2,3-triazolo[4,5-d]pyrimidin-3-yl]-cyclopentane-1,2,3-triol a) (1R-trans)-N-[2-(3-Dimethylaminophenyl)cyclopropyl]-carbamic acid, 1,1-dimethylethyl ester A mixture of the product of Example 84, step (b) (520mg), 37% aq. formaldehyde (0.47 ml), acetic acid (0.1 ml) and sodium triacetoxyborohydride (2.26 g) in 1,2-dichloroethane (10 ml) was stirred for 3.5 hours. Sodium bicarbonate solution was added and the mixture was extracted with dichloromethane. The organic layers were dried, evaporated and purified (SiO$_2$, petrol:ether, 1:1 as eluent) to give the subtitle compound (431 mg).

NMR δH (CDCl$_3$) 7.13 (1H, t), 6.56 (1H, dd), 6.49–6.46 (2H, m), 4.80 (1H, s), 3.92 (6H, s), 2.79–2.76 (1H, m), 2.02–1.96 (1H, m), 1.46 (9H, s), 1.21–1.09 (2H, m).

b) (1R-trans)-2-(3-Dimethylamino)cyclopropanamine

A solution of the product from step (a) (417 mg) in trifluoroacetic acid (3 ml) was stirred for 3 hours. The solvent was removed in vacuo, the residue basified with sodium bicarbonate solution and extracted with ethyl acetate. The organic layers were dried, evaporated and purified (SiO$_2$, dichloromethane:ethanol:ammonia, 150:8:1 as eluent) to give the subtitle compound (198 mg).

NMR δH (CDCl$_3$) 7.12 (1H, t), 6.55 (1H, dd), 6.46–6.44 (1H, m), 6.35 (1H, dd), 2.93 (6H, s), 2.60–2.52 (1H, m), 1.86–1.80 (1H, m), 1.72 (2H, s), 1.04–0.94 (2H, m).

c) [3aR-[3aα,4α,6α(1R*,2S*),6aα]]-6-[7-[[2-3-Dimethylaminophenyl)cyclopropyl]amino]-5-(propylthio)-3H-1,2,3-triazolo[4,5-d]pyrimidin-3-yl]-cyclopentan-1,3-dioxol-4-ol Prepared according to the method of Example 24, step (f) using the product of step (b).

MS (APCI) 526 (M+H$^+$, 100%)

d) [1S-[1α,2β,3β,4α(1S*,2R*)]]-4-[7-[[2-(3-Dimethylaminophenyl)cyclopropyl]amino]-5-(propylthio)-3H-1,2,3-triazolo[4,5-d]pyrimidin-3-yl]-cyclopentane-1,2,3-triol Prepared according to the method of Example 1, step (b) using the product of step (c).

m.p. 187–8° C.

MS (APCI) 486 (M+H$^+$, 100%)

NMR δH (d$_6$-DMSO) 9.29–9.25 (1H, m), 7.07 (1H, dd), 6.55–6.52 (2H, m), 6.64 (1H, d), 5.10 (1H, d), 5.02–5.00 (1H, m), 4.96–4.92 (1H, m), 4.90 (1H, d), 4.68–4.62 (1H, m), 3.94–3.91 (1H, m), 3.79–3.75 (1H, m), 3.25–2.92 (2H, m), 2.87 (6H, s), 2.62–2.53 (1H, m), 2.10–2.03 (1H, m), 1.96–1.88 (1H, m), 1.53–1.25 (4H, m), 0.82 (3H, t).

EXAMPLE 93

[1S-[1α,2β,3β,4α(1S*,2R*)]]-4-[7-[[2-(3-Fluoro-4-methoxyphenyl)cyclopropyl]amino]-5-(propylthio)-3H-1,2,3-triazolo[4,5-d]pyrimidin-3-yl]-cyclopentane-1,2,3-triol a) [3aR-[3aα,4α,6α(1R*,2S*),6aα]]-6-[7-[[2-(3-Fluoro-4-methoxyphenyl)-cyclopropyl]amino]-5-(propylthio)-3H-1,2,3-triazolo[4,5-d]pyrimidin-3-yl]-tetrahydro-2,2-dimethyl4H-cyclopentan-1,3-dioxol-4-ol The subtitle compound was prepared according to the method of Example 1, step (a) using the products of Example 24, step (d) and Example 76, step (d).

MS (APCI) 531 (M+H$^+$, 100%)

b) [1S-[1α,2β,3β,4α(1S*,2R*)]]-4-[7-[[2-(3-Fluoro-4-methoxyphenyl)-cyclopropyl]amino]-5-(propylthio)-3H-1,2,3-triazolo[4,5-d]pyrimidin-3-yl]-cyclopentane-1,2,3-triol Prepared according to the method of Example 1, step (b) using the product of step (a).

m.p. 156–7° C.

MS (APCI) 491 (M+H$^+$, 100%)

NMR δH (d$_6$-DMSO) 9.32 (1H, d), 7.10–6.94 (3H, m), 5.11 (1H, d), 5.03 (1H, d), 4.93 (1H, d), 4.90 (1H, d), 4.69–4.63 (1H, m), 3.96–3.90 (1H, m), 3.81 (3H, s), 3.79–3.75 (1H, m), 3.14–3.08 (1H, m), 3.01–2.82 (2H, m), 2.63–2.54 (1H, m), 2.10–2.03 (1H, m), 1.96–1.87 (1H, m), 1.57–1.45 (3H, m), 1.34–1.27 (1H, m), 0.83 (3H, t).

EXAMPLE 94

[1S-[1α,2β,3β,4α(1S*,2R*)]]-4-[7-[[2-(3,5-Dimethylphenyl)cyclopropyl]amino]-5-(propylthio)-3H-1,2,3-triazolo[4,5-d]pyrimidin-3-yl]-cyclopentane-1,2,3-triol a) 3-(3,5-Dimethylphenyl)-prop-2-enoic acid Prepared according to the method of Example 64, step (a), using 3,5-dimethyl-benzaldehyde.

MS (APCI) 175 (M–H$^+$, 100%)

b) [3aS-[1(E),3aα,6α,7aβ]]-1-[3-(3,5-Dimethylphenyl)-1-oxo-2-propenyl]-hexahydro-8,8dimethyl-3H-3a,6-methano-2,1-benzisothiazole-2,2-dioxide The subtitle compound was prepared according to the method of Example 19, step (f) using the product from step (a).

MS (APCI) 374 (M+H$^+$100%).

c) [3aS-[1(1S*,2S*), 3aα,6α,7aβ]]-1-[[2-(3,5-Dimethylphenyl)cyclopropyl]carbonyl]-hexahydro-8,8-dimethyl-3H-3a,6 methano-2,1-benzisothiazole-2,2-dioxide The subtitle compound was prepared according to the method of Example 19, step (g) using the product of step (b).

MS (APCI) 388 (M–H$^+$, 100%)

d) (1R-trans)-2-(3,5-Dimethylphenyl)-cyclopropanecarboxylic acid

The subtitle compound was prepared according to the method of Example 19, step (h) using the product of step (c).

MS (APCI) 189 (M–H$^+$, 100%)

e) (1R-trans)-2-(3,5-Dimethylphenyl) cyclopropanamine, [R-(R*,R*)]-2,3-dihydroxybutanedioate (1:1)

The subtitle compound was prepared according to the method of Example 20, step (b) using the product of step (d).

NMR δH (d$_6$-DMSO) 6.80 (1H, s), 6.70 (2H, s), 3.90 (2H, s), 2.66–2.61 (1H, m), 2.06–1.99 (1H, m), 1.20–1.13 (1H, m), 1.11–1.04 (1H, m).

f) [1S-[1α,2β,3β,4α(1S*,2R*)]]-4-[7-[[2-(3,5Dimethylphenyl)cyclopropyl]amino]-5-(propylthio)-3H-1,2,3-triazolo[4,5-d]pyrimidin-3-yl] cyclopentane-1,2,3-triol The title compound was prepared according to the method of Example 24, step (f) using the products of step (e) and Example 24, step (d).

MS (APCI) 471 (M+H$^+$, 100%)

NMR δH (d$_6$DMSO) 9.31 (1H, d), 6.81 (3H, s), 5.12–5.11 (1H, m), 5.04–5.00 (1H, m), 4.94–4.91 (1H, m), 4.67–4.63 (1H, m), 3.95–3.92 (1H, m), 3.78–3.76 (1H, m), 3.21–3.14 (1H, m), 2.99–2.84 (2H, m), 2.60–2.57 (1H, m), 2.24 (6H, s), 2.05–2.03 (1H, m), 1.92–1.91 (1H, m), 1.56–1.45 (2H, m), 1.32–1.27 (2H, m), 0.83 (3H, t).

EXAMPLE 95

[1S-[1α,2β,3β,4α(1S*,2R*)]]-4-[7-[[2-(3-Chloro-4-methoxyphenyl)cyclopropyl]amino]-5-(propylthio)-3H-1,2,3-triazolo[4,5-d]pyrimidin-3-yl]-cyclopentane-1,2,3-triol a) 3-(3-Chloro-4-methoxyphenyl)-prop-2-enoic acid Prepared according to the method of Example 64, step (a), using 3-chloro-4-methoxy-benzaldehyde.

NMR δH (d$_6$-DMSO) 7.83 (1H, d), 7.68–7.64 (1H, m), 7.55–7.49 (1H, m), 7.19–7.17 (1H, m), 6.50–6.46 (1H, d), 3.90 (3H, s).

b) [3aS-[1(E),3aα,6α,7aα]]-1-[3-(3-Chloro-4-methoxyphenyl)-1-oxo-2-propenyl]-hexahydro-8,8dimethyl-3H-3a,6-methano-2,1-benzisothiazole-2,2-dioxide The subtitle compound was prepared according to the method of Example 19, step (f) using the product from step (a).

MS (APCI) 408 (M–H$^+$100%).

c) [3aS-[1(1S*,2S*),3aα,6α,7aβ]]-1-[[2-(3-Chloro-4-methoxyphenyl)cyclopropyl]carbonyl]-hexahydro8,8dimethyl-3H-3a,6-methano-2,1-benzisothiazole-2,2-dioxide The subtitle compound was prepared according to the method of Example 19, step (g) using the product of step (b).

MS (APCI) 424 (M+H$^+$, 100%)

d) (1R-trans)-2-(3-Chloro-4-methoxyphenyl)-cyclopropanecarboxylic acid

The subtitle compound was prepared according to the method of Example 19, step (h) using the product of step (c).

NMR δH (CDCl$_3$) 7.13 (1H, d), 7.02–6.99 (1H, m), 6.85 (1H, d), 3.88 (3H, s).

e) (1R-trans)-2-(3-Chloro-4-methoxyphenyl) cyclopropanamine, [R-(R*,R*)]-2,3-dihydroxybutanedioate (1:1)

The subtitle compound was prepared according to the method of Example 20, step (b) using the product of step (d).

NMR δH (d₆-DMSO) 7.20–7.19 (1H, m), 7.09–7.05 (2H, m), 3.91 (2H, s), 2.66–2.61 (1H, m), 2.10–2.04 (1H, m), 1.19–1.05 (2H, m).

[1R-[1α,2α,3β(1R*,2S*),5β]]-3-[7-[[2-(3-Chloro-4-methoxyphenyl)cyclopropyl]amino]-5-(propylthio)-3H-1,2,3-triazolo[4,5-d]pyrimidin-3yl]-cyclopentane-1,2,3-triol The title compound was prepared according to the method of Example 24, step (f) using the products of step (e) and Example 24, step (d).

MS (APCI) 505 (M–H⁺, 100%)

NMR δH (d₆DMSO) 9.33 (1H, d), 7.32–7.31 (1H, m), 7.14–7.12 (1H, m), 7.07–7.05 (1H, m), 5.17–5.15 (1H, m), 5.05–5.04 (1H, m), 4.94–4.93 (2H, m), 4.66–4.64 (1H, m), 3.94–3.93 (1H, m), 3.83 (3H, s), 3.80 (3H, s), 3.29–3.27 (1H, m), 3.12–2.78 (2H, m), 2.63–2.53 (1H, m), 2.09–2.04 (1H, m), 1.95–1.88 (1H, m), 1.56–1.46 (2H, m), 1.36–1.29 (1H, m), 0.84–0.81 (3H, t).

EXAMPLE 96

[1R-[1α,2α,3β(1R*,2S*),5β]]-3-[7-[[2-(3-Chloro-4-methoxyphenyl)cyclopropyl]amino]-5-(propylthio)-3H-1,2,3-triazolo[4,5-d]pyrimidin-3-yl]-5-(hydroxymethyl)-cyclopentane-1,2-diol a) [3aR-[3aα,4α,6α(1R*,2S*),6aα]-6-[7-[[2-(3-Chloro-4-methoxyphenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 1, step (a) using the product of example 95, step (e).

MS (APCI) 561/563 (M+H⁺), 561 (100%).

[1R-[1α,2α,3β(1R*,2S*),5β]]-3-[7-[[2-(3-Chloro-4-methoxyphenyl)cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 1, step (b) using the product of step (a).

MS (APCI) 521/523 (M+H⁺), 521 (100%).

NMR δH (d₆-DMSO) 9.31 (1H, d), 7.33–7.05 (3H, m), 5.00 (1H, q), 4.44–4.41 (1H, m), 3.90–3.86 (1H, m), 3.83 (3H, s), 3.54–3.43 (2H, m), 3.11–3.07 (1H, m), 3.03–2.84 (2H, m), 2.31–2.21 (1H, m), 2.07–2.00 (2H, m), 1.90–1.80 (1H, m), 1.58–1.48 (3H, m), 1.33–1.24 (1H, m), 0.84 (3H, t)

EXAMPLE 97

[1R-[1α(1S*,2R*),2β,3β,4α]]-N-[3-[[2-[3-[2,3-Dihydroxy-4-(hydroxymethyl)cyclopentyl]-5-(propylthio)-3H-1,2,3-triazolo[4,5-d]pyrimidin-7-yl]amino]cyclopropyl]phenyl]-methanesulphonamide a) [3aS-[3aα,4α(1R*,2S*),6α,6aα]-N-[3-[2-[3-[Tetrahydro-6-(hydroxymethyl)-2,2-dimethyl-4H-cyclopenta-1,3-dioxol-4-yl]-5-propylthio]-3H-1,2,3-triazolo[4,5-d]pyrimidin-7-ylamino]cyclopropyl]phenyl]-methanesulphonamide The subtitle compound was prepared according to the method of Example 1, step (a) using the product of example 84, step (d).

MS (APCI) 590 (M+H⁺, 100%).

b) [1R-[1α(1S*,2R*),2β,3β,4α]]-N-[3-[[2-[3-[2,3-Dihydroxy-4-(hydroxymethyl)cyclopentyl]-5-(propylthio)-3H-1,2,3-triazolo[4,5-d]pyrimidin-7-yl]amino]cyclopropyl]phenyl]-methanesulphonamide The subtitle compound was prepared according to the method of Example 1, step (b) using the product of step (a).

MS (APCI) 550 (M+H⁺, 100%)

NMR δH (d₆-DMSO) 9.62 (1H, s), 9.32 (1H, d), 7.25 (1H, t), 7.05–6.91 (3H, m), 5.01–4.95 (2H, m), 4.74–4.70 (2H, m), 4.43–4.40 (1H, m), 3.87 (1H, q), 3.49–3.43 (2H, m), 3.22–3.19 (1H, m), 2.98 (3H, s), 2.95–2.86 (2H, m), 2.27–2.23 (1H, m), 2.13–2.08 (2H, m), 1.90–1.80 (1H, m), 1.55–1.48 (3H, m), 1.29–1.26 (1H, m), 0.83 (3H, t).

EXAMPLE 98

[1R-[1α,2α,3β(1R*,2S*),5β]]-3-[7-[[2-(3,5-Dimethoxyphenyl)cyclopropyl]amino]-5-(propylthio)-3H-1,2,3-triazolo[4,5-d]pyrimidin-3-yl]-5-(hydroxyethyl)-cyclopentane-1,2-diol Prepared according to the method of Example 1, step (a) using the product of example 64, step (e), followed by the method of Example 1, step (b).

MS (APCI) (M+H⁺), 517 (100%)

NMR δH (d₆DMSO) 9.31 (1H, d), 6.35–6.30 (3H, s), 4.98–4.96 (2H, m), 4.72–4.70 (2H, m), 4.45–4.40 (1H, m), 3.90–3.87 (1H, m), 3.73 (6H, m), 3.49–3.47 (2H, m), 3.22–3.18 (1H, m), 3.05–2.80 (2H, m), 2.30–2.20 (1H, s), 2.10–2.03 (2H, m), 1.92–1.81 (1H, m), 1.60–1.40 (2H, m), 1.40–1.30 (2H, m), 0.84 (3H, t).

EXAMPLE 99

[1S-[1α,2β,3β,4α(1S*,2R*)]]-4-[7-[[2-(3-Fluorophenyl)cyclopropyl]amino]-5-(propylthio)-3H-1,2,3-triazolo[4,5-d]pyrimidin-3-yl]-cyclopentane-1,2,3-triol a) [3aS-[1(E),3aα,6α,7aβ]]-1-[3-(3-Fluorophenyl)-1-oxo-2-propenyl]-hexahydro-8,8-dimethyl-3H-3a,6-methano-2,1-benzisothiazole-2,2-dioxide The subtitle compound was prepared according to the method of example 19, step (f) using 3-(3-fluorophenyl)-2-propenoic acid.

MS (APCI) (M+H⁺), 364 (100%)

b) [3aS-[1(1S*,2S*),3aα,6α,7aβ]]-1-[[2-(3-Fluorophenyl)cyclopropyl]carbonyl]-hexahydro-8,8-dimethyl-3H-3a,6-methano-2,1-benzisothiazole-2,2-dioxide The subtitle compound was prepared according to the method of example 19, step (g) using the product of step (a).

MS (APCI) 378 (M+H⁺, 100%)

c) (1R-trans)-2-(3-Fluorophenyl)-cyclopropanecarboxylic acid

The subtitle compound was prepared according to the method of example 19, step (h) using the product of step (b).

NMR δH (CDCl₃) 1.36–1.43 (1H, m), 1.65–1.71 (1H, m), 1.88–1.94 (1H, m), 2.56–2.63 (1H, m), 6.79 (1H, d, J=9.9 Hz), 6.88–6.94 (2H, m), 7.21–7.29 (1H, m).

d) (1R-trans)-2-(3-Fluorophenyl)cyclopropanamine, [R-(R*,R*)]-2,3-dihydroxybutanedioate (1:1)

The subtitle compound was prepared according to the method of example 20, step (b) using the product of step (c).

NMR δH (d$_6$-DMSO) 1.12–1.28 (2H, m), 2.12–2.18 (1H, m), 2.69–2.74 (1H, m), 3.95 (2H, s), 6.92–7.02 (3H, m), 7.27–7.34 (1H, m)

e) [1S-[1α,2β,3β,4α(1S*,2R*)]]-4-[7-[[2-(3-Fluorophenyl)cyclopropyl]amino]-5-(propylthio)-3H-1,2,3-triazolo[4,5-d]pyrimidin-3-yl]-cyclopentane-1,2,3-triol The title compound was prepared according to the method of example 24, step (f) using the products of step (d) and example 24, step (d).

MS (APCI) 461 (M+H$^+$, 100%)

NMR δH (d$_6$-DMSO) 9.37 (1H, d, J=4.2 Hz), 7.36–7.28 (1H, m), 7.06–6.96 (3H, m), 5.10–4.91 (4H, m), 4.69–4.63 (1H, m), 3.97–3.91 (1H, m), 3.79 (1H, s), 3.25–3.19 (1H, m), 2.99– 2.78 (2H, m), 2.65–2.55 (1H, m), 2.18–2.11 (1H, m), 1.96–1.87 (1H, m), 1.61–1.35 (4H, m), 0.81 (3H, t, J=7.2 Hz).

EXAMPLE 100

[1R-[1α(1S*,2R*),2β,3β,4α]]-N-[[3-[2-[3-(2,3-Dihydroxy-4-hydroxymethylcyclopentyl)-5-propylthio)-3H-1,2,3-triazolo[4,5-d]pyrimidin-7-yl]amino]cyclopropyl]phenyl]-acetamide Prepared according to the method of Example 1, step (a) using the products of example 87, step (b), followed by the method of Example 1, step (b).

MS (APCI) 528 (M+H$^+$, 100%).

NMR δH (d$_6$-DMSO) 9.86 (1H, s), 9.32 (1H, d), 7.41–7.36 (2H, m), 7.22–7.16 (1H, m), 6.87–6.85 (1H, m), 5.01–4.95 (2H, m), 4.71–4.45 (2H, m), 4.43–4.39 (1H, (1H, m), 3.51–3.45 (2H, m), 3.21–3.18 (1H, m), 2.97–2.83 (2H, m), 2.27–2.05 (3H, t), 1.89–1.79 (1H, m), 1.55–1.50 (3H, m), 1.48–1.26 (1H, m), 0.83 (3H, t).

EXAMPLE 101

[1R-[1α,2α,3β(1R*,2S*),5β]]-3-[7-[[2-(3,5Dichlorophenyl)cyclopropyl]amino]-5-(propylthio)-3H-1,2,3-triazolo[4,5-d]pyrimidin-3-yl]-5-(hydroxymethyl)cyclopentane-1,2-diol a) [3aR-[3aα,4α,6α(1R*,2S*),6aα-6-[7-[(2-(3,5-Dichlorophenyl)cyclopropyl)amino]-5-(propylthio)-3H-1,2,3-triazolo[4,5-d]pyrimidin-3-yl]-tetrahydro-2,2-dimethyl-4-H-cyclopenta-1,3-dioxole-4-methanol Prepared according to the method of Example 1, step (a) using the product of example 83, step (d).

MS (APCI) 565 (M+H$^+$, 100%).

b) [1R-1α,2α,3β(1R*,2S*),5β]]-3-[7-[[2-(3,5-Dichlorophenyl)cyclopropyl]amino]-5-(propylthio)-3H-1,2,3-triazolo[4,5-d]pyrimidin-3-yl]-5-(hydroxymethyl)-cyclopentane-1,2-diol Prepared according to the method of Example 1, step (b) using the product of step (a). Purification (HPLC, Symmetry® C18 column, 0.1% aqueous ammonium acetate:acetonitrile, isocratic elution 50% MeCN over 30 minutes) afforded the title compound (98 mg).

NMR δH (d$_6$-DMSO) 9.39 (1H, d), 7.40 (1H, s), 7.31 (2H, d) 7.23 (1H, s), 5.04–4.97 (2H, m), 4.74–4.70 (2H, m), 4.39 (1H, m), 3.89–3.85 (1H, m), 3.51–3.45 (2H, m), 3.19–3.10 (1H, m), 2.93–2.80 (2H, m), 2.30–2.20 (1H, m), 2.10–2.06 (2H, m), 1.89–1.79 (1H, m), 1.67–1.49 (1H, m), 1.58 (1H, m), 0.84 (3H, t).

EXAMPLE 102

Modifications to the 7- position of [1S-(1α,2α,3β,5β)]-3-(2-Hydroxyethyl)-5-5-propylthio)-3H-1,2,3-triazolo[4,5-d]pyrimidin-3-yl]-cyclopentane-1,2-diol a) [3aR-(3aα,4α,6α,6aα)]-6-[7-Amino-5-(propylthio)-3H-1,2,3-triazolo[4,5-d]pyrimidin-3-yl]-tetrahydro2,2-dimethyl-4H-cyclopenta-1,3-dioxole-4-carboxylic acid A solution of the product of example 6, step (b) (1.40 g) and ammonia in 1,4-dioxane (0.5 M, 60 ml) was stirred at 50° C. for 3 hours. The reaction mixture was evaporated to dryness, the residue triturated with water and the subtitle compound isolated by filtration (1.20 g).

MS (APCI) 395 (M+H$^+$, 100%).

b) [3aR-(3aα,4α,6α,6aα)]-6-[7-Amino-5-(propylthio)-3H-1,2,3-triazolo[4,5-d]pyrimidin-3-yl]-tetrahydro-2,2-dimethyl-4H-cyclopenta-1,3-dioxole4-acetic acid, methyl ester Isobutylchloroformate (0.33 ml) was added to an ice-cooled solution of the product of step a) (0.50 g) and N-methylmorpholine (0.26 ml) in tetrahydrofuran (10 ml). The solution was stirred at room temperature for 60 minutes then added to a solution of diazomethane (1.0 g) in ether (100 ml). The solution was stirred for 60 minutes then concentrated. The crude diazoketone (0.50 g) was taken into methanol (20 ml) and silver (I) oxide (250 mg) added portionwise at 60° C. The mixture was heated for 3 hours, diluted with chloroform (100 ml) then shaken vigorously with 0.88 aqueous ammonia (50 ml) and water (50 ml) for 20 mins. The mixture was extracted into chloroform and the extracts washed with water then dried and concentrated. Purification (SiO$_2$, ether:isohexane 2:1 as eluant) afforded the subtitle compound (0.50 g).

MS (APCI) 423 (M+H$^+$, 100%).

c) [3aR-(3aα,4α,6α,6aα)]-6-[7-Bromo-5-(propylthio)-3H-1,2,3-triazolo[4,5-d]pyrimidin-3-yl]-tetrahydro-2,2-dimethyl4H-cyclopenta-1,3-dioxole-4-ethanol DIBAL-H® (1.5 M solution in toluene, 5 ml) was added to an ice-cooled solution of the product of step b) (0.20 g) in toluene (10 ml) and the solution stirred at this temperature for 30 minutes before adding water (2 ml). The product was extracted into ether, the solution filtered through a pad of celite, dried and concentrated (175 mg). The resultant foam (175 mg) was taken into bromoform (5 ml)/isoamyl nitrite (1 ml) then heated at 85° C. for 40 minutes. The solution was concentrated and purified (SiO$_2$, ether:isohexane 2:1 as eluant) to afford the subtitle compound (0.15 g).

MS (APCI) 400 (M+H$^+$–57, 100%).

d) Modifications to the 7-position of [1S-(1α,2α,3β,5β)]-3-(2-Hydroxyethyl)-5-[5-(propylthio)-3H-1,2,3-triazolo[4,5-d]pyrimidin-3-yl]-cyclopentane-1,2-diol The product of step c) (2.5×10$^{-6}$ mol) in 1,4-dioxane (90 μl) and N,N-diisopropylethylamine (1.0×10$^{-5}$ mol) in 1,4-dioxane (100 μl) were added to each of the amine salts listed below (5.0×10$^{-6}$ mol). The reaction mixtures were heated at 60° C. for 4 hours before adding phthalate buffer (pH4, 400 μl) and extracting with ethyl acetate (4×200 μl). The extracts were concentrated and the residues taken into 80% acetic acid (150 μl), then heated at 80° C. for 30 minutes, The reaction mixtures were concentrated then azeotroped with ethanol (2×200 μl) to afford the title compounds.

The following amines were used (Preparations described previously in the experimental):

(1S-trans)-N-3-[(2-Aminocyclopropyl)phenyl]-methanesulfonamide, [R-(R*,R*)]-2,3-dihydroxybutanedioate (1:1)
(1R,trans)-2-(4-phenoxyphenyl)cyclopropanamine, [R-(R*,R*)]-2,3-dihydroxybutanedioate (1:1)
(1R,trans)-2-(2-phenoxyphenyl)cyclopropanamine, [R-(R*,R*)]-2,3-dihydroxybutanedioate (1:1)
(1R,trans)-2-(3-phenoxyphenyl)cyclopropanamine, [R-(R*,R*)]-2,3-dihydroxybutanedioate (1:1)
(1R,trans)-2-(4-bromophenyl)cyclopropanamine, [R-(R*,R*)]-2,3-dihydroxybutanedioate (1:1)
(1R-trans)-2-[(1,1'-biphenyl)-2-yl]cyclopropanamine, [R-(R*,R*)]-2,3-dihydroxybutanedioate (1:1)
(1R-trans)-2-[(1,1'-biphenyl)-3-yl]cyclopropanamine, [R-(R*,R*)]-2,3-dihydroxybutanedioate (1:1)
(1R,trans)-2-(3,5-dichlorophenyl)cyclopropanamine, [R-(R*,R*)]-2,3-dihydroxybutanedioate (1:1)
(1R,trans)-2-(3,4-dichlorophenyl)cyclopropanamine, [R-(R*,R*)]-2,3-dihydroxybutanedioate (1:1)
(1R,trans)-2-(3chloro-4-methoxyphenyl)cyclopropanamine, [R-(R*,R*)]-2,3-dihydroxybutanedioate (1:1)
(1R,trans)-2-(3,4-dimethoxyphenyl)cyclopropanamine, [R-(R*,R*)]-2,3-dihydroxybutanedioate (1:1)
(1S-trans)-N-4-[(2-Aminocyclopropyl)phenyl]-acetamide, [R-(R*,R*)]-2,3-dihydroxybutanedioate (1:1)
(1R,trans)-2-(3-chloro-4-methylphenyl)cyclopropanamine, [R-(R*,R*)]-2,3-dihydroxybutanedioate (1:1)
(1R,trans)-2-(4-chloro-3-methylphenyl)cyclopropanamine, [R-(R*,R*)]-2,3-dihydroxybutanedioate (1:1)
(1R,trans)-2-(4-fluoro-3-methylphenyl)cyclopropanamine, [R-(R*,R*)]-2,3-dihydroxybutanedioate (1:1)
(1R,trans)-2-(3-nitrophenyl)cyclopropanamine, [R-(R*,R*)]-2,3-dihydroxybutanedioate (1:1)
(1R,trans)-2-(4-methoxy-3-methylphenyl)cyclopropanamine, [R-(R*,R*)]-2,3-dihydroxybutanedioate (1:1)
(1R,trans)-2-(3-methoxy-4-methylphenyl)cyclopropanamine, [R-(R*,R*)]-2,3-dihydroxybutanedioate (1:1)
(1R,trans)-2-(4-N,N-dimethylphenyl)cyclopropanamine, [R-(R*,R*)]-2,3-dihydroxybutanedioate (1:1)
(1R,trans)-2-(3,4-difluorophenyl)cyclopropanamine, [R-(R*,R*)]-2,3-dihydroxybutanedioate (1:1)
(1R,trans)-2-(3,5-difluorophenyl)cyclopropanamine, [R-(R*,R*)]-2,3-dihydroxybutanedioate (1:1)
(1R,trans)-2-(3-chlorophenyl)cyclopropanamine, [R-(R*,R*)]-2,3-dihydroxybutanedioate (1:1)
(1R,trans)-2-(4-chlorophenyl)cyclopropanamine, [R-(R*,R*)]-2,3-dihydroxybutanedioate (1:1)
(1R,trans)-2-(4-methoxyphenyl)cyclopropanamine, [R-(R*,R*)]-2,3-dihydroxybutanedioate (1:1)
(1R,trans)-2-(2-methoxyphenyl)cyclopropanamine, [R-(R*,R*)]-2,3-dihydroxybutanedioate (1:1)
(1R,trans)-2-(3-methoxyphenyl)cyclopropanamine, [R-(R*,R*)]-2,3-dihydroxybutanedioate (1:1)
(1R,trans)-2-(3,5-dimethylphenyl)cyclopropanamine, [R-(R*,R*)]-2,3-dihydroxybutanedioate (1:1)
(1R,trans)-2-(4-fluorophenyl)cyclopropanamine, [R-(R*,R*)]-2,3-dihydroxybutanedioate (1:1)
(1R,trans)-2-(3-fluorophenyl)cyclopropanamine, [R-(R*,R*)]-2,3-dihydroxybutanedioate (1:1)
(1R,trans)-2-(2-methylphenyl)cyclopropanamine, [R-(R*,R*)]-2,3-dihydroxybutanedioate (1:1)
(1R,trans)-2-(3-methylphenyl)cyclopropanamine, [R-(R*,R*)]-2,3dihydroxybutanedioate (1:1)
(1R,trans)-2-(4-methylphenyl)cyclopropanamine, [R-(R*,R*)]-2,3-dihydroxybutanedioate (1:1)

The following products were obtained:

a) [1R-[1α(1S*,2R*),2β,3β,4α]]-N-[3-[2-[[3-[2,3-Dihydroxy-4-(2-hydroxyethyl)-cyclopentyl]-5-(propylthio)-3H-1,2,3-triazolo[4,5-d]pyrimidin-7-yl]amino]cyclopropyl]phenyl]-methanesulfonamide

MS (APCI) 564 (M+H+, 100%)

b) [1S-[1α,2α,3β,5β(1S*,2R*)]]-3-(2-Hydroxyethyl)-5-[7-[[2-(4-phenoxyphenyl)cyclopropyl]amino]-5-(propylthio)-3H-1,2,3-triazolo[4,5-d]pyrimidin-3-yl]-cyclopentane-1,2-diol

MS (APCI) 563 (M+H+, 100%)

c) [1S-[1α,2α,3β,5β(1S*,2R*)]]-3-(2-Hydroxyethyl)-5-[7-[[2-(3-phenoxyphenyl)cyclopropyl]amino]-5-(propylthio)-3H-1,2,3-triazolo[4,5-d]pyrimidin-3-yl]-cyclopentane-1,2-diol

MS (APCI) 563 (M+H+, 100%)

d) [1R-[1α,2α,3β(1R*,2S*),5β]]-3-[7-[[2-(4-Bromophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 551, 549 (M+H+, 100%)

e) [1R-[1α,2α,3β(1R*,2S*),5β]]-3-[7-[[2-[(1,1'-Biphenyl)-2-yl]cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 547 (M+H+, 100%)

f) [1R-[1α,2α,3β(1R*,2S*),5β]]-3-[7-[[2-[(1,1'-Biphenyl)-3-yl]cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 547 (M+H+, 100%)

g) [1R-[1α,2α,3β(1R*,2S*),5β]]-3-[7-[[2-(3,5-Dichlorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 539, 541, 543 (M+H+, 100%)

h) [1R-[1α,2α,3β(1R*,2S*),5β]]-3-[7-[[2-(3,4-Dichlorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 539, 541, 543 (M+H+, 100%)

i) [1R-[1α,2α,3β(1R*,2S*),5β]]-3-[7-[[2-(3-Chloro-4-methoxyphenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 537, 535 (M+H+, 100%)

j) [1R-[1α,2α,3β(1R*,2S*),5β]]-3-[7-[[2-(3,4-Dimethoxyphenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 531 (M+H⁺, 100%)

k) [1R-[1α(1S*,2R*),2β,3β,4α]]-N-[3-[2-[[3-[2,3-Dihydroxy-4-(2-hydroxyethyl)-cyclopentyl]-5-(propylthio)-3H-1,2,3-triazolo[4,5-d]pyrimidin-7-yl]amino]cyclopropyl]phenyl]-acetamide

MS (APCI) 528 (M+H⁺, 100%)

l) [1R-[1α,2α,3β(1R*,2S*),5β]]-3-[7-[[2-(3-Chloro-4-methylphenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 521, 519 (M+H⁺, 100%)

m) [1R-[1α,2α,3β(1R*,2S*),5β]]-3-[7-[[2-(4-Chloro-4-methylphenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 521, 519 (M+H⁺, 100%)

n) [1R-[1α,2α,3β(1R*,2S*),5β]]-3-[7-[[2-(4-Fluoro-3-methylphenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 519 (M+H⁺, 100%)

o) [1S-[1α,2α,3β,5β(1S*,2R*)]]-3-(2-Hydroxyethyl)-5-[7-[[2-(3-nitrophenyl)cyclopropyl]amino]-5-(propylthio)-3H-1,2,3-triazolo[4,5-d[pyrimidin-3-yl]-cyclopentane-1,2-diol

MS (APCI) 516 (M+H⁺, 100%)

p) [1S-1α,2α,3β,5β(1S*,2R*)]]-3-(2-Hydroxyethyl)-5-[7-[[2-(4-methoxy-3-methylphenyl)cyclopropyl]amino]-5-(propylthio)-3H-1,2,3-triazolo[4,5-d]pyrimidin-3-yl]-cyclopentane-1,2-diol

MS (APCI) 515 (M+H⁺, 100%)

q) [1S-[1α,2α,3β,5β(1S*,2R*)]]-3-(2-Hydroxyethyl)-5-[7-[[2-(3-methoxy-4-methylphenyl)cyclopropyl]amino]-5-(propylthio)-3H-1,2,3-triazolo[4,5-d]pyrimidin-3-yl]-cyclopentane-1,2-diol

MS (APCI) 515 (M+H⁺, 100%)

r) [1R-[1α,2α,3β(1R*,2S*),5β]]-3-[7-[[2-4-(N,N-Dimethylaminophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 514 (M+H⁺, 100%)

s) [1R-[1α,2α,3β(1R*,2S*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 507 (M+H⁺, 100%)

t) [1R-[1α,2α,3β(1R*,2S*),5β]]-3-[7-[[2-(3,5-Difluorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 507 (M+H⁺, 100%)

u) [1R-[1α,2α,3β(1R*,2S*),5β]]-3-[7-[[2-(3-Chlorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 507, 505 (M+H⁺, 100%)

v) [1S-[1α,2α,3β,5β(1S*,2R*)]]-3-(2-Hydroxyethyl)-5-[7-[[2-4-methoxyphenyl)cyclopropyl]amino]-5-(propylthio)-3H-1,2,3-triazolo[4,5-d]pyrimidin-3-yl]-cyclopentane-1,2-diol

MS (APCI) 507, 505 (M+H⁺, 100%)

w) [1S-[1α,2α,3β,5β(1S*,2R*)]]-3-(2-Hydroxyethyl)-5-[7-[[2-(2-methoxyphenyl)cyclopropyl]amino]-5-(propylthio)-3H-1,2,3-triazolo[4,5-d]pyrimidin-3-yl]-cyclopentane-1,2-diol

MS (APCI) 501 (M+H⁺, 100%)

x) [1S-[1α,2α,3β,5β(1S*,2R*)]]-3-(2-Hydroxyethyl)-5-[7-[[2-(4-methoxyphenyl)cyclopropyl]amino]-5-(propylthio)-3H-1,2,3-triazolo[4,5-d]pyrimidin-3-yl]-cyclopentane-1,2-diol

MS (APCI) 501 (M+H⁺, 100%)

y) [1S-1α,2α,3β,5β(1S*,2R*)]]-3-(2-Hydroxyethyl)-5-[7-[[2-(3-methoxyphenyl)cyclopropyl]amino]-5-(propylthio)-3H-1,2,3-triazolo[4,5-d]pyrimidin-3-yl]-cyclopentane-1,2-diol

MS (APCI) 501 (M+H⁺, 100%)

z) [1R-[1α,2α,3β(1R*,2S*),5β]]-3-[7-[[2-(3,5-Dimethylphenyl)cyclopropyl]amino]-5-(propylthio)-3H-1,2,3-triazolo[4,5-d]pyrimidin-3-yl]-5-(2-hydroxyethyl)-cyclopentane-2-diol

MS (APCI) 499 (M+H⁺, 100%)

aa) [1R-[1α,2α,3β(1R*,2S*),5β]]-3-[7-[[2-(4-Fluorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 489 (M+H⁺, 100%)

bb) [1R-[1α,2α,3β(1R*,2S*),5β]]-3-[7-[[2-(3-Fluorophenyl)cyclopropyl]amino]-5-(propylthio)-3H-1,2,3-triazolo[4,5-d]pyrimidin-3-yl]-5-(2-hydroxyethyl)-cyclopentane-1,2-diol

MS (APCI) 489 (M+H⁺, 100%)

cc) [1S-[1α,2α,3β,5β(1S*,2R*)]]-3-(2-Hydroxyethyl)-5-[7-[[2-(2-methylphenyl)cyclopropyl]amino]-5-(propylthio)-3H-1,2,3-triazolo[4,5-d]pyrimidin-3-yl]-cyclopentane-1,2diol

MS (APCI) 485 (M+H⁺, 100%)

dd) [1S-[1α,2α,3β,5β(1S*,2R*)]]-3-(2-Hydroxyethyl)-5-[7-[[2-(3-methylphenyl)cyclopropyl]amino]-5-(propylthio)-3H-1,2,3-triazolo[4,5-d]pyrimidin-3-yl]-cyclopentane-1,2-diol

MS (APCI) 485 (M+H⁺, 100%)

ee) [1S-[1α,2α,3β,5β(1S*,2R*)]]-3-(2-Hydroxyethyl)-5-[7-[[2-(4-methylphenyl)cyclopropyl]amino]-5-(propylthio)-3H-1,2,3-triazolo[4,5-d]pyrimidin-3-yl]-cyclopentane-1,2-diol

MS (APCI) 485 (M+H⁺, 100%)

ff) [1S-[1α,2α,3β,5β(1S*,2R*)]]-3-(2-
Hydroxyethyl)-5-[7-(cyclopropylamino)-5-
(propylthio)-3H-1,2,3-triazolo[4,5-d]pyrimidin-3-
yl]-cyclopentane-1,2-diol

MS (APCI) 461 (M+H$^+$, 100%)

EXAMPLE 103

[1S-[1α,2α,3β,5β(1S*,2R*)]]-3-(2-Hydroxy-2-
methylpropoxymethyl)-5-[7-[(2-phenylcyclopropyl)
amino]-5-(propylthio)-3H-1,2,3-triazolo[4,5-d]
pyrimidin-3-yl]-cyclopentane-1,2-diol a) [3aR-[3aα,4α,6α(1R*,2S*),6aα]]-2-[6-[7-[(2-
Phenylcyclopropyl)amino]-5-(propylthio)-3H-1,2,3-
triazolo[4,5-d]pyrimidin-3-yl]-tetrahydro-2,2-
dimethyl-4H-cyclopenta-1,3-dioxole-4-methoxy]
acetic acid, ethyl ester A solution of [3aR-[3aα,4α,6α(1S*,2R*),6aα]]-6-[7-chloro-5-(propylthio)-3H-1,2,3-triazolo[4,5-d]pyrimidin-3-yl]-tetrahydro-2,2-dimethyl4H-cyclopenta-1,3-dioxole-4-methanol (0.7 g) and rhodium acetate (0.39 g) in dichloromethane (20 ml) was treated with a solution of ethyl diazoacetate (0.21 ml) in dichloromethane (10 ml) over 3 hours. The reaction mixture was stirred at room temperature for 60 hours, concentrated and purified (SiO$_2$, isohexane-:ethyl acetate 3:1 as eluant). The resulting intermediate was taken into THF (10 ml), (1R-trans)-2-phenyl-cyclopropanamine, [R-(R*,R*)]-2,3-dihydroxybutanedioate (1:1) (0.2 g) and N,N-diisopropylethylamine (0.2 ml) was added and the solution stirred for 18 hours then concentrated. Purification (SiO$_2$, ether:isohexane 2:1 as eluant) gave the subtitle compound (0.23 g).

MS (APCI) 583 (M+H$^+$), 545 (100%).

b) [1S-[1α,2α,3β,5β(1S*,2R*)]]-3-(2-Hydroxy-2-
methylpropoxymethyl)-5-[7-[(2-phenylcyclopropyl)
amino]-5-(propylthio)-3H-1,2,3-triazolo[4,5-d]
pyrimidin-3-yl]-cyclopentane-1,2-diol Prepared according to the method of example 10, using the product of step a). Purification (HPLC, Symmetry® C18 column, 0.1% aqueous ammonium acetate:acetonitrile, isocratic elution 30% MeCN over 30 minutes) afforded the title compound (115 mg).

NMR δH (d$_6$-DMSO) 9.32 (1H, d), 7.31–7.15 (5H, m), 5.00–4.98 (2H, m) 4.78 (1H, d), 4.46–4.44 (1H, m), 4.29 (1H, s), 3.89–3.86 (1H, m), 3.51–3.48 (2H, m), 3.18–3.17 (3H, m), 2.96–2.84 (2H, m), 2.27–2.26 (1H, m), 2.21–2.13 (1H, m), 2.13–2.11 (1H, m), 1.88–1.86 (1H, m), 1.50–1.48 (3H, m), 1.32–1.31 (1H, m), 1.09 (6H, s), 0.81 (3H, t).

EXAMPLE 104

[1R-[1α,2α,3β(1R*,2S*),5β]]-3-[7-[[2-(3-Chloro-4-
methylphenyl)cyclopropyl]amino]-5-(propylthio)-
3H-1,2,3-triazolo[4,5-d]pyrimidin-3-yl]-5-
(hydroxymethyl)-cyclopentane-1,2-diol a) 3-(3-Chloro-4-methylphenyl)-2-propenoic acid The subtitle compound was prepared according to the method of Example 64, step (a) using (3-chloro-4-methyl) benzaldehyde (prepared according to the method of S. O. Nwaukwa etal, Tetrahedron Lett., 1982, 23, 3131).

MS (APCI) 191 (M−H$^+$,100%)

b) [3aS-[1(E),3aα,6α,7aβ]]-1-[3-(3-Chloro-4-
methylphenyl)-1-oxo-2-propenyl]-hexahydro-8,8-
dimethyl-3H-3a,6-methano-2,1-benzisothiazole-2,2-
dioxide The subtitle compound was prepared according to the method of Example 19, step (f) using the product of step (a).

MS (APCI) 394/392 (M−H$^+$) 392 (100%)

c) [3aS-[1(1S*,2S*),3aα,6α,7aβ]]-1-[[2-(3-Chloro-
4-methylphenyl)cyclopropyl]carbonyl]-hexahydro-8,
8-dimethyl-3H-3a,6-methano-2,1-benzisothiazole-2,
2-dioxide The subtitle compound was prepared according to the method of Example 19, step (g) using the product of step (b). m.p. 154–156° C.

d) (1R-trans)-2-(3-Chloro-4-methylphenyl)
cyclopropanecarboxylic acid

The subtitle compound was prepared according to the method of Example 19, step (h) using the product of step (c). MS (APCI) 209 (M−H$^+$, 100%).

e) (1R-trans)-2-(3-Chloro-4-methylphenyl)
cyclopropanamine, [R-(R*,R*)]-2,3-
dihydroxybutanedioate (1:1)

The subtitle compound was prepared according to the method of Example 20, step (b) using the product of step (d). MS (APCI) 182 (M+H$^+$, 100%).

f) [3aR-[3aα,4α,6α(1R*,2S*),6aα]]-6-[7-[[2-(3-
Chloro-4-methylphenyl)cyclopropyl]amino]-5-
(propylthio)-3H-1,2,3-triazolo[4,5-d]pyrimidin-3-
yl]-tetrahydro-2,2-dimethyl-4H-cyclopenta-1,3-
dioxole-4-methanol The subtitle compound was prepared according to the method of example 1, step a), using the product of step (e). MS (APCI) 547, 545 (M+H$^+$), 545 (100%).

g) [1R-[1α,2α,3β(1R*,2S*),5β]]-3-[7-[[2-(3-
Chloro-4-methylphenyl)cyclopropyl]amino]-5-
(propylthio)-3H-1,2,3-triazolo[4,5-d]pyrimidin-3-
yl]-5-(hydroxymethyl)-cyclopentane-1,2-diol The title compound was prepared according to the method of example 57, step b), using the product of step (f).

MS (APCI) 507, 505 (M+H$^+$), 505 (100%).

NMR δH (d$_6$-DMSO) 9.32 (1H, d), 7.29–7.21 (2H, m), 7.08–7.01 (1H, m), 5.04–4.95 (2H, m), 4.74–4.71 (2H, m), 4.46–4.39 (1H, m), 3.90–3.86 (1H, m), 3.55–3.43 (2H, m), 3.17–3.09 (1H, m), 3.00–2.80 (2H, m), 2.29 (3H, s), 2.26–2.20 (1H, m), 2.12–2.05 (2H, m), 1.89–1.79 (1H, m), 1.57–1.45 (3H, m), 1.39–1.32 (1H, m), 0.84 (3H, t).

EXAMPLE 105

[1R-[1α(1S*,2R*),2β,3β,4α]]-4-[2-[[3-(2,3,4-
Trihydroxycyclopentyl)-5-(propylthio)-3H-1,2,3-
triazolo[4,5-d]pyrimidin-7-yl]amino]cyclopropyl]
phenylsulfonamide a) (1S-trans)-4-(2-Aminocyclopropyl)
phenylsulfonamide, hydrochloride The title compound was prepared from (1R-trans)-phenylcyclopropanamine according to the method described in U.S. Pat. No. 3,487,154.

m.p. 211–2° C.

NMR δH (d$_6$-DMSO) 8.71 (3H, s), 7.72 (2H, d), 7.35 (2H, d), 7.33 (2H, s), 2.94–2.82 (1H, m), 2.47–2.42 (1H, m), 1.55–1.47 (1H, m), 1.28 (1H, q).

b) [3aS-[3aα,4α,6α(1R*,2S*),6aα]]-4-[2-[[3-(2,2-
Dimethyl-6-hydroxy-tetrahydro-4H-cyclopenta-1,3-
dioxol-4-yl)-5-(propylthio)-3H-1,2,3-triazolo[4,5-d]
pyrimidin-7-yl]amino]cyclopropyl]
phenylsulfonamide Prepared according to the method of Example 24, step (f) using the product of step (a) and the product of Example 24, step (d).

MS (APCI) 562 (M+H⁺, 100%)

c) [1R-[1α(1S*,2R*),2β,3β,4α]]-4-[2-[[3-(2,3,4-Trihydroxycyclopentyl)-5-(propylthio)-3H-1,2,3-triazolo[4,5-d]pyrimidin-7-yl]amino]cyclopropyl] phenylsulfonamide Prepared according to the method of Example 1, step (b) using the product of step (b).
m.p. 200–1° C.
MS (APCI) 522 (M+H⁺, 100%)
NMR δH (d₆-DMSO) 9.40 (1H, d), 7.78 (2H, d), 7.52 (2H, d), 5.76 (2H, s), 5.18–4.88 (4H, m), 4.71–4.60 (1H, m), 3.98–3.87 (1H, m), 3.81–3.75 (1H, m), 3.29–3.22 (1H, m), 2.97–2.79 (2H, m), 2.65–2.51 (1H, m), 2.25–2.18 (1H, m), 1.96–1.85 (1H, m), 1.75–1.40 (3H, m), 0.81 (3H, t).

EXAMPLE 106

[1R-[1α,2α,3β(1R*,2S*),5β]]-3-[5-(Butylthio)-7-[(2-phenylcyclopropyl)amino]-3H-1,2,3-triazolo[4,5-d]pyrimidin-3-yl]-5-hydroxymethyl)-cyclopentane-1,2-diol a)[1S-[1α,2α,3β,5β(1S*,2R*)]]-3-(Hydroxymethyl) 5-[7-[(2-phenylcyclopropyl)amino]-5-(propylsulphonyl)-3H-1,2,3-triazolo[4,5d]pyrimidin-3-yl]-cyclopentane-1,2-diol Prepared according to the method of Example 4, step (a) using the product of Example 1, steb (b).
MS (APCI) 489 (M+H⁺, 100%)

b)[1R-[1α,2α,3β(1R*,2S*),5β]]-3-[5-(Butylthio)-7-[(2-phenylcyclopropyl)amino]-3H-1,2,3-triazolo[4,5-d]pyrimidin-3-yl]-5-(hydroxymethyl)-cyclopentane-1,2-diol Prepared according to the method of Example 4, step (b) using the product of step (a) and butanethiol.
MS (APCI) 471 (M+H⁺, 100%)
NMR δH (d₆-DMSO) 9.32 (1H, d), 7.33–7.15 (5H, m), 5.01–4.96 (2H, m), 4.73–4.69 (2H, m), 4.45–4.42 (1H, m), 3.87 (1H, q), 3.49–3.44 (2H, m), 3.22–3.19 (1H, m), 3.00–2.85 (2H, m), 2.30–2.20 (1H, m), 2.17–2.08 (2H, m), 1.90–1.80 (1H, m), 1.53–1.44 (3H, m), 1.33–1.20 (3H, m), 0.81 (3H, t).

EXAMPLE 107

[1S-1α,2α,3β,5β(1S*,2R*)]]-3-(Hydroxymethyl)-5-[5-(pentylthio)-7-[(2-phenylcyclopropyl)amino]-3H-1,2,3-triazolo[4,5-d]pyrimidin-3-yl]-cyclopentane-1,2-diol Prepared according to the method of Example 4, step (b) using the product of example 107, step (a) and pentanethiol.
MS (APCI) 485 (M+H⁺, 100%)
NMR δH (d₆-DMSO) 9.33 (1H, d), 7.31–7.16 (5H, m), 5.03–4.97 (2H, m), 4.72–4.70 (2H, m), 4.45–4.40 (1H, m), 3.88–3.86 (1H, m), 3.49–3.45 (2H, m), 3.21–3.19 (1H, m), 3.00–2.94 (1H, m), 2.89–2.82 (1H, m), 2.33–2.22 (1H, m), 2.14–2.09 (2H, m), 1.87–1.79 (1H, m), 1.53–1.31 (5H, m), 1.21–1.19 (3H, m), 0.81 (3H, t).

EXAMPLE 108

[1S-[1α,2α,3β,5β(1S*,2R*)]]-3-(Hydroxymethyl)5-[7-[(2-phenylcyclopropyl)amino]-5-(prop-2-ynylthio)-3H-1,2,3-triazolo[4,5-d]pyrimidin-3-yl]-cyclopentane-1,2-diol a)[1S-[1α,2α,3β,5β(1S*,2R*)]]-3-(Hydroxymethyl)-5-[5-(mercapto)-7[(2-phenylcyclopropyl)amino]-3H-1,2,3-triazolo[4,5-d]pyrimidin-3-yl]-cyclopentane1,2-diol A solution of the product of Example 107, step (a) (0.4 g) in DMSO (10 ml) was treated with sodium hydrosulphide hydrate (0.4 g) and the mixture was stirred at room temperature for 2 hours. The mixture was poured into aqueous brine (150 ml) containing acetic acid (2 ml) and extracted with ethyl acetate (3×100 ml). The combined organic extracts were dried and concentrated to afford the subtitle compound (0.3 g).
MS (APCI) 415 (M+H⁺, 100%)

b)[1S-[1α,2α,3β,5β(1S*,2R*)]]-3-(Hydroxymethyl)-5-[7-[(2-phenylcyclopropyl)amino]-5-(prop-2-ynylthio)-3H-1,2,3-triazolo[4,5-d]pyrimidin-3-yl]-cyclopentane-1,2-diol A solution of the product of step (a) (168 mg) in DMF (5 ml) was treated with N,N-diisopropylethylamine (58 mg) followed by propargyl bromide (58 mg). The mixture was heated at 60° C. for 1 hour and then poured into aqueous brine (100 ml) and extracted with ethyl acetate (100 ml). The organic layer was washed with further aqueous brine (3×100 ml), dried and concentrated and the residue purified (SiO₂, chloroform:methanol 95:5 as eluant) to afford the title compound (40 mg).
MS (APCI) 453 (M+H⁺, 100%)
NMR δH (d₆-DMSO) 9.44 (1H, d), 7.31–7.16 (5H, m), 5.00–4.95 (2H, m), 4.7–4.70 (2H, m), 4.44 (1H, q), 3.94–3.71 (3H, m), 3.54–3.44 (2H, m), 3.23–3.18 (1H, m), 3.05–3.01 (1H, m), 2.30–2.27 (1H, m), 2.20–2.09 (2H, m), 1.93–1.85 (1H, m), 1.52–1.47 (1H, m), 1.37–1.30 (1H, m).

EXAMPLE 109

[1S-[1α,2α,3β,5β(1S*,2R*)]]-3-(Hydroxymethyl)5-[7-[[2-(3,5-dimethylphenyl)cyclopropyl]amino]-5-(propylthio)-3H-1,2,3-triazolo[4,5-d]pyrimidin-3-yl]-cyclopentane-1,2-diol a) [3aR-[3aα,4α,6α(1R*,2S*),6aα]-Tetrahydro-2,2-dimethyl-6-[7-[[2-(3,5-dimethylphenyl)cyclopropyl]amino]-5-(propylthio)-3H-1,2,3-triazolo[4,5-d]pyrimidin-3-yl]-4H-cyclopenta-1,3-dioxole-4-methanol Prepared by the method of Example 1, step (a), using the product of Example 94, step (e).
MS (APCI) 525 (M+H⁺, 100%).

b) [1S-[1α,2α,3β,5β(1S*,2R*)]]-3-(Hydroxymethyl)-5-[7-[[2-(3,5-dimethylphenyl)cyclopropyl]amino]-5-(propylthio)-3H-1,2,3-triazolo[4,5-d]pyrimidin-3-yl]-cyclopentane-1,2-diol Prepared by the method of Example 57, step (b), using the product of step (a).
MS (APCI) 485 (M+H⁺, 100%).
NMR δH (d₆-DMSO) 9.29 (1H, d), 6.85–6.73 (3H, m), 5.06–4.94 (2H, m), 4.75–4.68 (2H, m), 4.48–4.39 (1H, m), 3.94–3.85 (1H, m), 3.56–3.41 (2H, m), 3.19–3.11 (1H, m), 3.05–2.82 (2H, m), 2.32–2.16 (7H, m), 2.13–2.00 (2H, m), 1.92–1.78 (1H, m), 1.61–1.41 (3H, m), 1.37–1.22 (1H, m), 0.90–0.80 (3H, t).

EXAMPLE 110

[1S-[1α,2α,3β,5β(1S*,2R*)]]-3-(2-Hydroxyethyl)5-[5-(methylthio)-7-[(2-phenylcyclopropyl)amino]-3H-1,2,3-triazolo [4,5-d]pyrimidin-3yl]-cyclopentane-1,2-diol a) [3aR-[3aα,4α,6α(1R*,2S*),6aα]-6-[7-[(2-Phenylcyclopropyl)amino]-5-propylsulfonyl)-3H-1,2,3-triazolo[4,5-d]pyrimidin-3-yl]-tetrahydro-2,2-dimethyl-4H-cyclopenta-1,3-dioxole-4-ethanol DIBAL-H® (1.5M solution in toluene, 20 ml) was added to an ice-cooled solution of the product of Example 11, step a) (2.00 g) in toluene (30 ml) and the solution stirred at this temperature for 30 minutes before adding ethyl acetate (2 ml). The solution was washed with water and concentrated. The residue (1.8 g) was taken into ethanol and cooled to 4° C. before adding 3-chloroperoxybenzoic acid (50–55%, 2.5 g) and allowing the reaction to stir at room temperature for 18 hours. The solution was washed with aqueous sodium metabisulfite solution (3×10 ml) then dried and concentrated. Purification (SiO$_2$, ether:isohexane, 80:20, as eluent) afforded the subtitle compound (1.8 g).

MS (APCI) 543 (M+H$^+$, 100%)

b)[1S-(1α,2α,3β,5β(1S*,2R*)]-3-(2-Hydroxyethyl)-5-[5-(methylthio)-7-[(2-phenylcyclopropyl)amino]-3H-1,2,3-triazolo[4,5-d]pyrimidin-3-yl-cyclopentane-1,2-diol Prepared by the method of Example 4, step b), using the product of step a) and commercially available sodium methanethiolate then deprotected using the method of Example 1, step (b). Purification (HPLC, Novapak® C18 column, 0.1% aqueous ammonium acetate:acetonitrile, isocratic elution 30% MeCN over 30 minutes) afforded the title compound (110 mg).

NMR δH (d$_6$-DMSO) 7.31–7.15 (5H, m), 5.0–4.99 (1H, m) 4.40–4.35 (1H, m), 3.76–3.72 (1H, m), 3.47–3.40 (2H, m), 3.18–3.13 (1H, m), 2.37–2.30 (4H, m), 2.16–2.10 (1H, m), 2.05–2.00 (1H, m), 1.75–1.65 (2H, m), 1.56–1.49 (2H, m), 1.35–1.32 (1H, m).

EXAMPLE 111

[1R-[1α,2α,3β(1R*,2S*),5β]]-3-[5-(Butylthio)-7-[(2-phenylcyclopropyl)amino]-3H-1,2,3-triazolo[4,5-d]pyrimidin-3-yl]-5-(2-hydroxyethyl)-cyclopentane-1,2-diol Prepared by the method of Example 4, step (b) using the product of Example 110, step a) and butanethiol then deprotected using the method of Example 1, step (b). Purification (HPLC, Novapak® C18 column, 0.1% aqueous ammonium acetate:acetonitrile, isocratic elution 45% MeCN over 30 minutes) afforded the title compound (210 mg).

NMR δH (d$_6$-DMSO) 9.33 (1H, d), 7.31–7.15 (5H, m), 5.01–4.94 (2H, m) 4.77 (1H, d), 4.49–4.39 (1H, m), 3.80–3.75 (1H, m), 3.50–3.48 (2H, m), 3.19–3.10 (1H, m), 3.00–2.85 (2H, m), 2.38–2.29 (1H, m), 2.18–2.13 (1H, m), 2.05–2.00 (1H, m), 1.79–1.64 (2H, m), 1.51–1.38 (4H, m), 1.35–1.21 (3H, t).

EXAMPLE 112

[1R-[1α,2α,3β(1R*,2S*),5β]]-3-[7-[[2-(4-chlorophenyl)cyclopropyl]amino]-5-(propylthio)-3H-1,2,3-triazolo[4,5-d]pyrimidin-3-yl]-5-[(2-hydroxy)ethoxy]-cyclopentane-1,2-diol a) 2-[[(1S-cis)-4-azido-2-cyclopenten-1-yl]oxy] acetic acid, 1,1-dimethylethyl ester (1S-cis)-4-Azido-2-cyclopenten-1-ol (3.4 g) (prepared as described by D. R. Deardorff et al., J. Org. Chem, 1989, 54, 2759) in tetrahydrofuran (60 ml) was added dropwise to a suspension of sodium hydride (1.1 g. of a 60% suspension in oil) in tetrahydrofuran (60 ml) at 0° C. On completion of the addition the mixture was allowed to warm to ambient temperature the added dropwise to a solution of tert-butyl bromoacetate (10.1 ml) in tetrahydrofuran (60 ml) at 0° C. Water (200 ml) was added and the product extracted into ethyl acetate (200 ml) then dried and concentrated. Purification (SiO$_2$, ethyl acetate:isohexane,10:90, as eluent) afforded the subtitle compound (3.6 g).

NMR δH (d$_6$-DMSO) 6.21–6.18 (1H, m), 6.02–5.99 (1H, m), 4.49–4.44 (1H, m), 4.33–4.22 (1H, m), 4.03 (2H, s), 2.72–2.64 (1H, m), 1.63–1.55 (1H, m), 1.43 (9H, s).

b) 2[[[(1S-cis)-4-[6-Chloro-5-nitro-2-(propylthio)-pyrimidin-4-yl]amino]-2-cyclopenten-1-yl]oxy]-acetic acid, 1,1-dimethylethyl ester To a solution of the product from step (a) (3.5 g) in tetrahydrofuran (250 ml) water (25 ml) was added triphenyl phosphine (4.3 g) and the reaction mixtue stirred at ambient temperature for three days. The solvents was evaporated and traces of water removed by evaporation from toluene. A solution of the resulting amine (3.0 g) in tetrahydrofuran (100 ml) was added dropwise over one hour to a solution of 4,6-dichloro-5-nitro-2-(propylthio)-pyrimidine (prepared as described in WO 9703084) (3.7 g). The reaction mixture was stirred for one hour the solvents evaporated and the product redissolved in ethyl acetate (500 ml) then washed with water (200 ml). The organics were separated, dried and evaporated. Purification (SiO$_2$, ethyl acetate:isohexane 5:95 as eluant) afforded the subtitle compound (2.5 g).

MS (APCI) 445/447 (M+H), 445 (100%).

c) 2-[[[1S-cis)-4-[5-amino-6-chloro-2-(propylthio)-pyrimidin-4-yl]amino]-2-cyclopenten-1-yl]oxy]-acetic acid, 1,1-dimethylethyl ester.

Prepared according to the method of example 12, step b) using the product of step b).

MS (APCI) 415/417 (M+H), 415 (100%).

d) 2-[(1S-cis)-4-[7-Chloro-5-(propylthio)-3H-1,2,3-triazolo[4,5-d]pyrimidin-3-yl]-2-cyclopenten-1-yl] oxy]-acetic acid, 1,1-dimethylethyl ester Prepared according to the method of example 6, step b) using the product of step c).

MS (APCI) 426/428 (M+H), 426 (100%).

e) 2-[(1cis)-4-[7-Amino-5-(propylthio)-3H-[1,2,3]-triazolo[4,5-d]pyrimidin-3-yl]-2-cyclopenten-1-yl] oxy]-acetic acid, 1,1-dimethylethyl ester Prepared according to the method of example 1, step a) using the product of step d) and '880' ammonia solution.

MS (APCI) 407 (M+H$^+$, 100%).

f)[3aR-(3aα,4α,6α,6aα)]-2-[[6-[7-Amino-5-(propylthio)-3H-1,2,3-triazolo[4,5-d]pyrimidin-3-yl]-tetrahydro-2,2-dimethyl-4H-cyclopenta-1,3-dioxol-4-yl]oxy]acetic acid, 1,1-dimethylethyl ester Prepared according to the method of example 15, step c) using the product of step e).

MS (APCI) 481 (M+H$^+$, 100%).

g)[3aR-(3aα,4α,6α,6aα)]-2-[[6-[7-Bromo-5-(propylthio)-3H-1,2,3-triazolo[4,5-d]pyrimidin-3-yl]-tetrahydro-2,2-dimethyl-4H-cyclopenta-1,3-dioxol-4-yl]oxy]ethanol DIBAL-H® (1.5M solution in toluene, (4 m) was added to an ice-cooled solution of the product of step f) (0.30 g) in toluene (9 ml). The solution stirred at this temperature for 30 minutes before adding ethyl acetate (2 ml) and water (5 ml).

The reaction mixture was filtered through a Kieselguhr pad, washed with brine, dried and evaporated. The product was redissolved in bromoform (5 ml) and isoamyl nitrite (2 ml) added. The reaction mixture was heated at 80° C. for thirty minutes, cooled and solvent evaporated. Purification (SiO$_2$, ethyl acetate:isohexane 3:7 as eluant) to afforded the subtitle compound (0.11 g).

MS (APCI) 474/476 (M+H), 474 (100%).

h)[1R-[1α,2α,3β(1R*,2S*),5β]]-3-[7-[[2-(4-chlorophenyl)cyclopropyl]amino]-5-(propylthio)-3H-1,2,3-triazolo[4,5,-d]pyrimidin-3-yl]-5-[(2-hydroxy)ethoxy]-cyclopentane-1,2-diol The title compound was prepared according to the method of example 1, step b) using the product of step g).

NMR δH (d$_6$-DMSO) 9.35 (1H, s), 7.33 (1H, d), 7.22 (1H, d), 5.15 (2H, m), 4.95 (1H, q), 4.61 (1H, m), 4.57–4.54 (1H, m), 3.96–3.91 (1H, m), 3.77–3.74 (1H, m), 3.56–3.44 (4H, m), 3.15–3.19 (1H, m), 2.96–2.79 (2H, m), 2.67–2.59 (1H, m), 2.15–2.10 (1H, m), 2.06–1.99 (1H, m), 1.58–1.53 (1H, m), 1.51–1.44 (2H, m), 1.39–1.32 (1H, m), 0.80 (3H, t).

MS (APCI) 521/523 (M+H), 521 (100%).

EXAMPLE 113

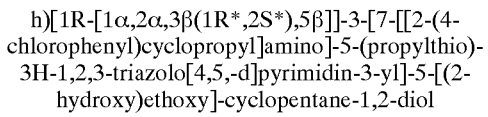
[1S-[1α,2α,3β,5β(1S*,2R*)]]-3-(Hydroxymethyl)-5-[7-[(2-phenylcyclopropyl)amino]-5-[(3,3,3-trifluoropropyl)thio]-3H-1,2,3-triazolo[4,5-d]pyrimidin-3-yl]-cyclopentane-1,2-diol a) [3aR-[3aα,4α,6α(1R*,2S*),6aα]-Tetrahydro-2,2-dimethyl-6-7-[(2-phenylcyclopropyl)amino]-5-[(3,3,3-trifluoropropyl)thio]-3H-1,2,3-triazolo[4,5-d]pyrimidin-3-yl]-4H-cyclopenta-1,3-dioxole-4-methanol The subtitle compound was prepared according to the method of Example 6, step (b) using [3aR-[3aα,4α,6α,6aα]-6-[[5-amino-6-Chloro-2-[(3,3,3-trifluoropropyl)thio]-4-pyrimidinyl]-amino]-tetrahydro-2,2-dimethyl-4H-cyclopenta-1,3-dioxole-4-methanol (prepared as described in WO 9703084), followed by the method of Example 1, step (a).

b) [1S-[1α,2α,3β,5β(1S*,2R*)]]-3-(Hydroxymethyl)-5-[7-[(2-phenylcyclopropyl)amino]-5-[(3,3,3-trifluoropropyl)thio]-3H-1,2,3-triazolo[4,5-d]pyrimidin-3-yl]-cyclopentane-1,2-diol The title compound was prepared according to the method of Example 1, step (b) using the product of step a).

MS (APCI) 511 (M+H$^+$, 100%)

NMR δH (d$_6$-DMSO) 9.43 (1H, d), 7.32–7.27 (2H, m), 7.21–7.16 (3H, m), 5.01–4.95 (2H, m), 4.72–4.70 (2H, m), 4.44–4.41 (1H, m), 3.88–3.84 (1H, m), 3.50–3.44 (2H, m), 3.25–3.11 (3H, m), 2.75–2.70 (1H, m), 2.28–2.19 (2H, m), 2.15–2.05 (1H, m), 1.85–1.78 (1H, m), 1.49–1.46 (1H, m), 1.36–1.10 (2H, m).

EXAMPLE 114

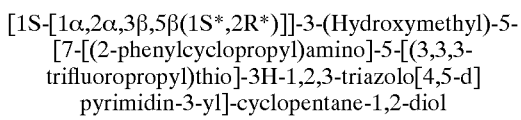
[1S-[1α,2β,3β,4α(1S*,2R*)]]-4-[7-[[2-(3-Chloro-4-methylphenyl)cyclopropyl]amino]-5-(propylthio)-3H-1,2,3-triazolo[4,5-d]pyrimidin-3-yl]-cyclopentane-1,2,3-triol Prepared according to the method of Example 24, step (f), using the products of Example 24, step (d) and Example 104, step (e).

MS (APCI) 493/491 (M+H$^+$), 491 (100%)

NMR δH (d$_6$-DMSO) 9.85 (1H, d), 7.28 (2H, d), 7.26 (1H, d), 7.06 (1H, dd), 5.11 (1H, d), 5.02 (1H, d), 4.96 (1H, q), 4.92 (1H, d), 4.69–4.62 (1H, m), 3.96–3.89 (1H, m), 3.82–3.75 (1H, m), 3.19–2.79 (3H, m), 2.64–2.52 (1H, m), 2.29 (3H, s), 2.25–2.05 (1H, m), 1.95–1.86 (1H, m), 1.73–1.31 (4H, m), 0.80 (3H, t).

Pharmacological Data

The preparation for the assay of the P$_{2T}$-receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125 G followed by further centrifugation for 15 minutes at 640 G. The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C. Following addition of a further 300 ng/ml PGI$_2$, the pooled suspension was centrifuged once more for 15 minutes at 640 G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentration of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 μl of 10 mg/ml solution of clottable protein in saline) and 300 nM (10 μl of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an IC$_{50}$. Compounds exemplified have pIC$_{50}$ values of more than 5.0.

What is claimed is:

1. A compound of formula (I)

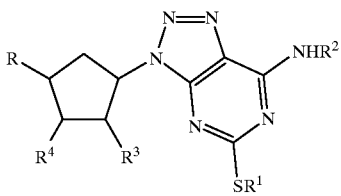

(I)

wherein:

$R^1$ is a $C_{1-6}$ alkyl, $C_{2-6}$ alkenyl, $C_{2-6}$ alkynyl, $C_{3-8}$-cycloalkyl or a phenyl group, each group being optionally substituted by one or more substituents selected from halogen, $OR^8$, $NR^9R^{10}$, $SR^{11}$ or $C_{1-6}$ alkyl (itself optionally substituted by one or more halogen atoms);

$R^2$ is $C_{1-8}$ alkyl optionally substituted by one or more substituents selected from the group consisting of halogen, $OR^8$, $NR^9R^{10}$, $SR^{11}$, or $C_{3-8}$-cycloalkyl, aryl (optionally substituted by one or more $C_{1-6}$ alkyl groups and/or halogen atoms), and $C_{1-6}$-alkyl;

or $R^2$ is a $C_{3-8}$-cycloalkyl group optionally substituted by one or more substituents selected from the group consisting of halogen, $OR^8$, $NR^9R^{10}$, $SR^{11}$, $C_{1-6}$-alkyl and phenyl, the latter two groups being optionally substituted by one or more substituents selected from the group consisting of halogen, $NO_2$, $C(O)R^8$, $OR^8$, $SR^{11}$, $NR^{12}R^{13}$, 1,3-benzodioxolyl, phenyl and $C_{1-6}$-alkyl the latter two groups being optionally substituted by $OR^8$, $NR^9R^{10}$ or one or more halogen atoms;

one of $R^3$ and $R^4$ hydroxy and the other is hydrogen, hydroxy or $N^9R^{10}$;

R is a group $(CR^5R^6)_mOR^7$ where m is 0 or 1, $R^5$ and $R^6$ are independently hydrogen, $C_{1-6}$ alkyl or phenyl the latter two groups being optionally substituted by halogen, and $R^7$ is hydrogen, $C_{1-6}$ alkyl or $(CR^5R^6)_nR^{14}$ where $R^5$ and $R^6$ are as defined above, n is 1 to 3 and $R^{14}$ is COOH, $OR^{15}$, $NR^{16}R^{17}$ or $CONR^{16}R^{17}$;

or R is a $C_{1-4}$ alkyl or $C_{2-4}$ alkenyl group, each of which is substituted by one or more groups selected from the group consisting of =S, =O, =$NR^{20}$ and $OR^{21}$ and optionally substituted by one or more groups selected from the group consisting of halogen, $C_{1-4}$ alkyl, phenyl, $SR^{21}$, $NO_2$ and $NR^{22}R^{23}$ (where $R^{21}$, $R^{22}$ and $R^{23}$ are independently hydrogen, $C_{1-4}$ alkyl or phenyl; $R^{20}$ is $OR^{24}$ or $NR^{25}R^{26}$ where $R^{24}$ is hydrogen, $C_{1-4}$ alkyl or phenyl, and $R^{25}$ and $R^{26}$ are independently hydrogen, $C_{1-4}$ alkyl, aryl, $C_{1-6}$ acyl, arylsulphonyl or arylcarbonyl);

$R^8$ is hydrogen, $C_{1-6}$ alkyl optionally substituted by halogen or $R^8$ is phenyl optionally substituted by one or more substituents selected from halogen, $NO_2$, $C(O)R^6$, $OR^6$, $SR^9$, $NR^{10}R^{11}$;

$R^9$, $R^{10}$ and $R^{11}$ are independently hydrogen or $C_{1-6}$ alkyl;

$R^{12}$ and $R^{13}$ are independently hydrogen, $C_{1-6}$ alkyl, $C_{1-6}$ acyl, $C_{1-6}$ alkyl sulfonyl optionally substituted by halogen, or phenyl sulfonyl optionally substituted by $C_1$–$C_4$ alkyl; and $R^{15}$, $R^{16}$ and $R^{17}$ are independently hydrogen or $C_{1-6}$ alkyl;

or a pharmaceutically acceptable salt or solvate thereof.

2. A compound of formula (I) as defined in claim 1 having the following stereochemistry:

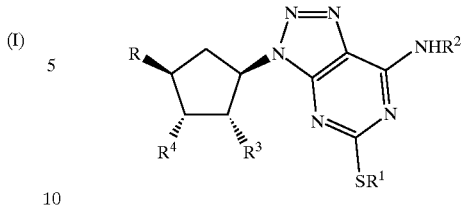

(Ia)

3. A compound according to claim 1 in which $R^1$ is $C_{1-4}$ alkyl or phenyl substituted by trifluoromethyl.

4. A compound according to claim 1 in which $R^2$ is butyl or cyclopropyl optionally substituted by phenyl, the phenyl group itself being optionally substituted by one or more halogen, $C_{1-6}$ alkyl, phenoxy or phenyl groups.

5. A compound according to claim 1 in which $R^3$ and $R^4$ are both hydroxy.

6. A compound according to claim 1 in which $R^5$ and $R^6$ are both hydrogen.

7. A compound according to claim 1 in which R is OH, $CH_2OH$, $CH_2CH_2OH$, $OCH_2CH_2OH$, $CH_2OCH_2C(CH_3)_2OH$ and $OCH_2C(CH_3)_2OH$.

8. A compound according to claims 1 which is:

[1S-[1α,2α,3β,5β(1S*,2R*)]]-3-(Hydroxymethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-(1α,2α,3β,5β)]-5-[7-[(Cyclopropyl)amino]-5-(propylthio)-3H-1,2,3-triazolo[4,5-d]pyrimidin-3-yl]-3-(hydroxymethyl)-cyclopentane-1,2-diol,

[1S-(1α,2α,3β,5β)]-5-[7-(Butylamino)-5-(propylthio)-3H-1,2,3-triazolo[4,5-d]pyrimidin-3-yl]-3-(hydroxymethyl)-cyclopentane-1,2-diol,

[1S-(1α,2α,3β,5β)]-5-[7-Butylamino)-5-[[(4-trifluoromethyl)phenyl]thio]-3H-1,2,3-triazolo[4,5-d]pyrimidin-3-yl]-3-(hydroxymethyl)-cyclopentane-1,2-diol, 2-[[[1R-(1α,2β,3β,4α)]-4-[7-(Butylamino)-5-(propylthio)-3H-1,2,3-triazolo[4,5-d]pyrimidin-3-yl]-2,3-dihydroxy-cyclopentyl]methoxy]acetic acid, 1-[[1S-[1α,2β,3β,4α(1S*,2R*)]]-2-Hydroxy-4-[7-[(2-phenylcyclopropyl)amino]-5-(propylthio)-3H-1,2,3-triazolo[4,5-d]pyrimidin-3-yl]-2,3-dihydroxy-cyclopentyl]-ethanone, 1-[[1S-[1α,2β,3β,4α]]-4-[7-(Butylamino)-5-(propylthio)-3H-1,2,3-triazolo[4,5-d]pyrimidin-3-yl]-2,3-dihydroxy-cyclopentyl]-2-hydroxy-ethanone, 1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-ethanone, 1-[[1S-[1α,2β,3β,4α]-4-[7-(Butylamino)-5-(propylthio)-3H-1,2,3-triazolo[4,5-d]pyrimidin-3-yl]-2,3-dihydroxy-cyclopentyl]-ethanone,

[1S-[1α,2α,3β,5β(1S*,2R*)]]-3-(1-Hydroxy-1-methylethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2β,3β,4α(1S*,2R*)]]-4-[7-[(2-Phenylcyclopropyl)amino]-5-(propylthio)-3H-1,2,3-triazolo[4,5-d]pyrimidin-3-yl]-cyclopentane-1,2,3-triol, 2-[[[1S-[1α,3β,4α(1S*,2R*)]]-3-Hydroxy-4-[7-[(2-phenylcyclopropyl)amino]-5-(propylthio)-3H-1,2,3-triazolo[4,5-d]pyrimidin-3-yl]-cyclopentyl]oxy]acetic acid, 2-[[[1S-[1α,2β,4α(1S*,2R*)]]-2-Hydroxy-4-[7-[(2-phenylcyclopropyl)amino]-5-(propylthio)-3H-1,2,3-triazolo[4,5-d]pyrimidin-3-yl]-cyclopentyl]oxy]acetic acid, 2-[[[1S-(1α,2β,3β,4α)]-4-[7-(Butylamino)-5-(propylthio)-3H-1,2,3-triazolo[4,5-d]pyrimidin-3-yl]-2,3-dihydroxy-cyclopentyl]oxy]acetic acid, 2-[[[1S-(1α,2β,3β,4α)]-4-[7-(Butylamino)-5-(propylthio)-3H-1,2,3-triazolo[4,5-d]pyrimidin-3-yl]-2,3-dihydroxycyclopentyl]oxy]acetamide,

[1S-[1α,2β,3β,4α(1S*,2R*)]]-4-[[5-Methylthio)-7-[(2-phenylcyclopropyl)amino]-3H-1,2,3-triazolo[4,5-d]pyrimidin-3-yl]-cyclopentane-1,2,3-triol,

[1S-[1α,2β,3β,4α(1S*,2R*)]]-4-[5-[(Methylethyl)thio]-7-[(2-phenylcyclopropyl)amino]-3H-1,2,3-triazolo[4,5-d]pyrimidin-3-yl]-cyclopentane-1,2,3-triol,

[1S-[1α,2β,3β,4α(1S*,2R*)]]-4-[7-[[2-(4-Fluorophenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(4-Methoxyphenyl)cyclopropyl]amino]-5-(propylthio)-3H-1,2,3-triazolo[4,5-d]pyrimidin-3-yl]cyclopentane-1,2,3-triol,

[1S-[1α,2β,3β,4α(1S*,2R*)]]-4-[7-[[2-(4-Methylphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(4-Chlorophenyl)cyclopropyl]amino]-5-(propylthio)-3H-1,2,3-triazolo[4,5-d]pyrimidin-3-yl]-cyclopentane-1,2,3-triol, 2-[[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]oxy]-acetamide,

[1S-[1α,2β,3β,4α(1S*,2R*)]]-4-[7-[[2-(3-Methoxyphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3-Methylphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3-Chlorophenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3-Nitrophenyl)cyclopropyl]amino]-5-(propylthio)-3H-1,2,3-triazolo[4,5-d]pyrimidin-3-yl]-cyclopentane-1,2,3-triol,

[1S-[(1α,2β,3β,4α(1S*,2R*)]]-4-[7-[[2-(4-Phenoxyphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3-Phenoxyphenyl)cyclopropyl]amino]-5-(propylthio)-3H-1,2,3-triazolo[4,5-d]pyrimidin-3-yl]-cyclopentane-1,2,3-triol,

[1S-[1a,2b,3b,4a(1S*,2R*)]-4-[7-[[2-(3-Aminophenyl)cyclopropyl]amino]-5-(propylthio)-3H-1,2,3-triazolo[4,5-d]pyrimidin-3-yl]-cyclopentane-1,2,3-triol,

[1S-(1a,2a,3b,5b)]-3-[7-(Butylamino)-5-(propylthio)-3H-1,2,3-triazolo[4,5-d]pyrimidin-3-yl]-5-(3-hydroxypropoxy)-cyclopentane-1,2-diol,

[1S-[1a,2a,3b,5b(1S*,2R*)]]-3-(2-Hydroxyethoxy)-5-[7-[(2-phenylcyclopropyl)amino]-5-(propylthio)-3H-1,2,3-triazolo[4,5-d]pyrimidin-3-yl]-cyclopentane-1,2-diol,

[1S-[1a,2a,3b,5b(1S*,2R*)]]-3-(Hydroxymethyl)-5-[7-[[2-(4-methoxyphenyl)cyclopropyl]amino]-5-(propylthio)-3H-1,2,3-triazolo[4,5-d]pyrimidin-3-yl]-cyclopentane-1,2-diol,

[1R-[1a,2a,3b(1S*,2R*),5b]]-5-[7-[[(2-(4-Chlorophenyl)cyclopropyl)]amino]-5-(propylthio)-3H-1,2,3-triazolo[4,5-d]pyrimidin-3-yl]-3-(hydroxymethyl)-cyclopentane-1,2,-diol,

[1R-[1α,2α,3β(1S*,2R*),5β]]-3-[7-[[2-(3-Chlorophenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2α,3β,5β(1S*,2R*)]]-3-(Methoxymethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[5-(methylthio)-7-[(2-phenylcyclopropyl)amino]-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[(2-phenylcyclopropyl)amino]-5-[(1-methylethyl)thio]-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[(2-phenylcyclopropyl)amino]-5-(prop-2-enylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[5-(4-methylphenylthio)-7-[(2-phenylcyclopropyl)amino]-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(4-methylphenyl)cyclopropyl]amino]-5-(propylthio)-3H-1,2,3-triazolo[4,5-d]pyrimidin-3-yl]-cyclopentane-1,2-diol,

[1S-[1α,2α,3β,(R*),5β(1S*,2R*)]]-3-(1-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,(S*),5β(1S*,2R*)]]-3-(1-Hydroxyethyl)-5-[7-[(2-phenylcyclopropyl)amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[5-(Ethylthio)-7-[[2-phenylcyclopropyl]amino]-3H-1,2,3-triazolo[4,5-d]pyrimidin-3-yl]-5-(hydroxymethyl)-cyclopentane-1,2-diol,

[1R-[1α,2α,3β(1R*,2S*),5β]]-3-[7-[[2-[(1,1'-Biphenyl)-4-yl]cyclopropyl]amino]-5-(propylthio)-3H-1,2,3-triazolo[4,5-d]pyrimidin-3-yl]-5-(hydroxymethyl)-cyclopentane-1,2-diol,

[1R-(1α,2α,3β,5β)]-3-[7-(Butylamino)-5-(cyclopentylthio)-3H-1,2,3-triazolo[4,5-d]pyrimidin-3-yl]-5-(hydroxymethyl)-cyclopentane-1,2-diol,

[1S-[1α,2α,3β,5β(1S*,2R*)]]-3-(Hydroxymethyl)-5-[7-[(2-phenylcyclopropyl)amino]-5-[4-(trifluoromethyl)-phenylthio]-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(4-phenoxyphenyl)cyclopropyl]amino]-5-(propylthio)-3H-1,2,3-triazolo[4,5-d]pyrimidin-3-yl]-cyclopentane-1,2-diol,

[1R-[1α,2α,3β(1S*,2R*),5β]]-3-[7-[[2-(2-Chlorophenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2α,3β,5β(1S*,2R*)]]-3-(2-Hydroxyethoxymethyl)-5-[7-[(2-phenylcyclopropyl)amino]-5-(propylthio)-3H-1,2,3-triazolo[4,5-d]pyrimidin-3-yl]-cyclopentane-1,2diol,

[1R-[1α,2β,3β,4α(1R*,2S*)]]-3-Hydroxy-2-methoxy-4-[7-[(2-phenylcyclopropyl)amino]-5-(propylthio)-3H-1,2,3-triazolo[4,5-d]pyrimidin-3-yl]-cyclopentanemethanol,

[1R-[1α,2β,3β,4α(1R*,2S*)]]-2-Hydroxy-3-methoxy-4-[7-[(2-phenylcyclopropyl)amino]-5-(propylthio)-3H-1,2,3-triazolo[4,5-d]pyrimidin-3-yl]-cyclopentanemethanol,

[1S-[1α,2α,3β(E),5β(1S*,2R*)]]-3-(3-Hydroxy-prop-1-enyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(3-Hydroxypropyl)-5-[7-[(2-phenylcyclopropyl)amino]-5-(propylthio)-3H-1,2,3-triazolo[4,5-d]pyrimidin-3-yl]-cyclopentane-1,2-diol, 1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentyl]-2-methoxyethanone,

[1S-(1α,2α,3β,5β)]-3-(Hydroxymethyl)-5-[7-[[(trans)-2-(3,4-methylenedioxyphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(3-methoxyphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(4-hydroxyphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(3-methylphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(3-phenoxyphenyl)cyclopropyl]amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[7-[[2-(4-Fluorophenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2α,3β,5β(1S*,2R*)]]-3-(Hydroxymethyl)-5-[7-[[2-(3-nitrophenyl)cyclopropyl]amino]-5-(propylthio)-3H-1,2,3-triazolo[4,5-d]pyrimidin-3-yl]-cyclopentane-1,2-diol,

[1R-[1α,2α,3β,5β(1R*,2S*)]]-3-[7-[[2-(3-Aminophenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2β,3β,4α(1S*,2R*)]]-4-[7-[[2-(3,5-Dimethoxyphenyl)cyclopropyl]amino]-5-(propylthio)-3H-1,2,3-triazolo[4,5-d]pyrimidin-3-yl]-cyclopentane-1,2,3-triol,

[1S-[1α,2α,3β,5β(1S*,2R*)]]-3-[(2-Hydroxy-2,2-dimethyl)ethoxy]-5-[7-[(2-phenylcyclopropyl)amino]-5-(propylthio)-3H-1,2,3-triazolo[4,5-d]pyrimidin-3-yl]-1,2-cyclopentanediol,

[1S-[1α,2α,3β,5β(1S*,2R*)]]-3-(Hydroxymethyl)-5-[7-[[2-[4-(1-methylethyloxy)phenyl]cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(3-Hydroxypropoxy)-5-[7-[(2-phenylcyclopropyl)amino]-5-(propylthio)-3H-1,2,3-triazolo[4,5-d]pyrimidin-3-yl]-1,2-cyclopentanediol,

[1S-[1α,2β,3β,4α(1S*,2R*)]]-4-[7-[[2-(3,4-Difluorophenyl)cyclopropyl]amino]-5-(propylthio)-3H-1,2,3-triazolo[4,5-d]pyrimidin-3-yl]-cyclopentane-1,2,3-triol,

[1R-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2β,3β,4α(1S*,2R*)]]-4-[7-[[2-(3,5-Difluorophenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-[[1,1'-Biphenyl]-3-yl]cyclopropyl]amino]-5-(propylthio)-3H-1,2,3-triazolo[4,5-d]pyrimidin-3-yl]-cyclopentane-1,2,3-triol,

[1R-[1α,2α,3β(1R*,2S*),5β]]-3-[7-[[2-[1,1'-Biphenyl]-3-yl]cyclopropyl]amino]-5-(propylthio)-3H-1,2,3-triazolo[4,5-d]pyrimidin-3-yl]-5-(hydroxymethyl)-cyclopentane-1,2-diol, N-Ethyl-[[[1S-[1α,2β,3β,4α(1S*,2R*)]]-2,3-dihydroxy-4-[7-[(2-phenylcyclopropyl)amino]-5-(propylthio)-3H-1,2,3-triazolo[4,5-d]pyrimidin-3-yl]-cyclopentyl]oxy]-acetamide,

[1S-[1α,2β,3β,4α(1S*,2R*)]]-4-[7-[[2-(3-Methoxy-4-methylphenyl)cyclopropyl]amino]-5-(propylthio)-3H-1,2,3-triazolo[4,5-d]pyrimidin-3-yl]-cyclopentane-1,2,3-triol,

[1R-[1α,2α,3β(1R*,2S*),5β]]-3-[7-[[2-(4-N,N-Dimethylaminophenyl)cyclopropyl]amino]-5-(propylthio)-3H-1,2,3-triazolo[4,5-d]pyrimidin-3-yl]-5-hydroxymethyl-cyclopentane-1,2diol,

[1R-[1α,2α,3β(1R*,2S*),5β]]-3-[7-[[2-(3-Fluoro-4-methoxyphenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2α,3β,5β(1S*,2R*)]]-3-(Hydroxymethyl)-5-[7-[[2-(4-methoxy-3-methylphenyl)cyclopropyl]amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[7-[[2-(3,4-Dichlorophenyl)cyclopropyl]amino]-5-(propylthio)-3H-1,2,3-triazolo[4,5-d]pyrimidin-3-yl]-3-(hydroxymethyl)-cyclopentane-1,2-diol, 1S-[1α,2α,3β,5β(1S*,2R*)]]-3-[(2-Amino)ethoxy]-5-[7-(2-phenylcyclopropyl)amino]-5-propylthio-3H-[1,2,3]-triazolo[4,5-d]pyrimidin-3-yl]-cyclopentane-1,2-diol,

[1R-(1α,2α,3β(1R*,2S*),5β)]-3-[7-[[2-(3,4-Dimethylphenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2β,3β,4α(1S*,2R*)]]-4-[7-[[2-(3,4-Dimethylphenyl)cyclopropyl]amino]-5-(propylthio)-3H-1,2,3-triazolo[4,5-d]pyrimidin-3-yl]-cyclopentane-1,2,3-triol,

[1R-(1α,2α,3β,5β)]]-3-[7-(Cyclopropylamino)-5-[[4-(trifluoromethyl)phenyl]thio]-3H-1,2,3-triazolo[4,5-d]pyrimidin-3-yl]-5-(hydroxymethyl)-cyclopentane-1,2-diol,

[1S-[1α,2β,3β,4α(1S*,2R*)]]-4-[7-[[2-(3,5-Dichlorophenyl)cyclopropyl]amino]-5-(propylthio)-3H-1,2,3-triazolo[4,5-d]pyrimidin-3-yl]-cyclopentane-1,2,3-triol,

[1R-[1α(1S*,2R*),2β,3β,4α]]-N-[3-[2-[[3-(2,3,4-Trihydroxy-cyclopentyl)-5-(propylthio)-3H-1,2,3-triazolo[4,5-d]pyrimidin-7-yl]amino]cyclopropyl]phenyl]-methanesulfonamide,

[1S-[1α,2β,3β,4α(1S*,2R*)]]-4-[7-[[2-(3,4-Dimethoxyphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(4-Methoxy-3-methylphenyl)cyclopropyl]amino]-5-(propylthio)-3H-1,2,3-triazolo[4,5-d]pyrimidin-3-yl]-cyclopentane-1,2,3-triol,

[1R-[1α(1S*,2R*),2β,3β,4α]]-N-[3-[2-[[3-(2,3,4-Trihydroxy-cyclopentyl)-5-(propylthio)-3H-1,2,3-triazolo[4,5-d]pyrimidin-7-yl]amino]cyclopropyl]phenyl]-acetamide,

[1S-[1α,2β,3β,4α(1S*,2R*)]]-4-[7-[[(2-(3,4-Dichlorophenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(4-Chloro-3-methylphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(trans)]]-4-[7-[[2-(Phenylmethyl)cyclopropyl]amino]-5-(propylthio)-3H-1,2,3-triazolo[4,5-d]pyrimidin-3-yl]-cyclopentane-1,2,3-triol,

[1R-[1α,2α,3β(1R*,2S*),5β]]-3-[7-[[2-(4-Chloro-3-methylphenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2β,3β,4α(1S*,2R*)]]-4-[7-[[2-(3-Dimethylaminophenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3-Fluoro-4-methoxyphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3,5-Dimethylphenyl)cyclopropyl]amino]-5-(propylthio)-3H-1,2,3-triazolo[4,5-d]pyrimidin-3-yl]-cyclopentane-1,2,3-triol,

[1S-[1α,2β,3β,4α(1S*,2R*)]]-4-[7-[[2-(3-Chloro-4-methoxyphenyl)cyclopropyl]amino]-5-(propylthio)-3H-1,2,3-triazolo[4,5-d]pyrimidin-3-yl]-cyclopentane-1,2,3-triol,

[1R-[1α,2α,3β(1R*,2S*),5β]]-3-[7-[[2-(3-Chloro-4-methoxyphenyl)cyclopropyl]amino]-5-(propylthio)-3H-1,2,3-triazolo[4,5-d]pyrimidin-3-yl]-5-(hydroxymethyl)-cyclopentane-1,2-diol,

[1R-[1α(1S*,2R*),2β,3β,4α]]-N-[3-[[2-[3-[2,3-Dihydroxy-4-(hydroxymethyl)cyclopentyl]-5-(propylthio)-3H-1,2,3-triazolo[4,5-d]pyrimidin-7-yl]amino]cyclopropyl]phenyl]-methanesulphonamide,

[1R-[1α,2α,3β(1R*,2S*),5β]]-3-[7-[[2-(3,5-Dimethoxyphenyl)cyclopropyl]amino]-5-(propylthio)-3H-1,2,3-triazolo[4,5-d]pyrimidin-3-yl]-5-(hydroxymethyl)-cyclopentane-1,2-diol,

[1S-[1α,2β,3β,4α(1S*,2R*)]]-4-[7-[[2-(3-Fluorophenyl)cyclopropyl]amino]-5-(propylthio)-3H-1,2,3-triazolo[4,5-d]pyrimidin-3-yl]-cyclopentane-1,2,3-triol,

[1R-[1α(1S*,2R*),2β,3β,4α]]-N-[[3-[2-[3-(2,3-Dihydroxy-4-hydroxymethylcyclopentyl)-5-(propylthio)-3H-1,2,3-triazolo[4,5-d]pyrimidin-7-yl]amino]cyclopropyl]phenyl]-acetamide,

[1R-[1α,2α,3β(1R*,2S*),5β]]-3-[7-[[2-(3,5-Dichlorophenyl)cyclopropyl]amino]-5-(propylthio)-3H-1,2,3-triazolo[4,5-d]pyrimidin-3-yl]-5-(hydroxymethyl)-cyclopentane-1,2-diol,

[1R-[1α(1S*,2R*),2β,3β,4α]]-N-[3-[2-[[3-[2,3-Dihydroxy-4-(2-hydroxyethyl)-cyclopentyl]-5-(propylthio)-3H-1,2,3-triazolo[4,5-d]pyrimidin-7-yl]amino]cyclopropyl]phenyl]-methanesulfonamide,

[1S-[1α,2α,3β,5β(1S*,2R*)]]-3-(2-Hydroxyethyl)-5-[7-[[2-(4-phenoxyphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(3-phenoxyphenyl)cyclopropyl]amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[7-[[2-(4-Bromophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-[(1,1'-Biphenyl)-2-yl]cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-[(1,1'-Biphenyl)-3-yl]cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3,5-Dichlorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3,4-Dichlorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3-Chloro-4-methoxyphenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3,4-Dimethoxyphenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α(1S*,2R*),2β,3β,4α]]-N-[3-[[3-[2,3-Dihydroxy-4-(2-hydroxyethyl)-cyclopentyl]-5-(propylthio)-3H-1,2,3-triazolo[4,5-d]pyrimidin-7-yl]amino]cyclopropyl]phenyl]-acetamide,

[1R-[1α,2α,3β(1R*,2S*),5β]]-3-[7-[[2-(3-Chloro-4-methylphenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(4-Chloro-4-methylphenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(4-Fluoro-3-methylphenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1S-[1α,2α,3β,5β(1S*,2R*)]]-3-(2-Hydroxyethyl)-5-[7-[[2-(3-nitrophenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(4-methoxy-3-methylphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(3-methoxy-4-methylphenyl)cyclopropyl]amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[7-[[2-(4-N,N-Dimethylaminophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3,5-Difluorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3-Chlorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1S-[1α,2α,3β,5β(1S*,2R*)]]-3-(2-Hydroxyethyl)-5-[7-[[2-(2-methoxyphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(4-methoxyphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(3-methoxyphenyl)cyclopropyl]amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[7-[[2-(3,5-Dimethylphenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(4-Fluorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(3-Fluorophenyl)cyclopropyl]amino]-5-(propylthio)-3H-1,2,3-triazolo[4,5-d]pyrimidin-3-yl]-5-(2-hydroxyethyl)-cyclopentane-1,2-diol,

[1S-[1α,2α,3β,5β(1S*,2R*)]]-3-(2-Hydroxyethyl)-5-[7-[[2-(2-methylphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(3-methylphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-[[2-(4-methylphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[7-(cyclopropylamino)-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxy-2-methylpropoxymethyl)-5-[7-[(2-phenylcyclopropyl)amino]-5-(propylthio)-3H-1,2,3-triazolo[4,5-d]pyrimidin-3-yl]-cyclopentane-1,2-diol,

[1R-[1α,2α,3β(1R*,2S*),5β]]-3-[7-[[2-(3-Chloro-4-methylphenyl)cyclopropyl]amino]-5-(propylthio)-3H-1,2,3-triazolo[4,5-d]pyrimidin-3-yl]-5-(hydroxymethyl)-cyclopentane-1,2-diol,

[1R-[1α(1S*,2R*),2β,3β,4α]]-4-[2-[[3-(2,3,4-Trihydroxycyclopentyl)-5-(propylthio)-3H-1,2,3-triazolo[4,5-d]pyrimidin-7-yl]amino]cyclopropyl]phenylsulfonamide,

[1R-[1α,2α,3β(1R*,2S*),5β]]-3-[5-(Butylthio)-7-[(2-phenylcyclopropyl)amino]-3H-1,2,3-triazolo[4,5-d]pyrimidin-3-yl]-5-(hydroxymethyl)-cyclopentane-1,2-diol,

[1S-[1α,2α,3β,5β(1S*,2R*)]]-3-(Hydroxymethyl)-5-[5-(pentylthio)-7-[(2-phenylcyclopropyl)amino]-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[(2-phenylcyclopropyl)amino]-5-(prop-2-enylthio)-3H-1,2,3-triazolo[4,5-d]pyrimidin-3-yl]-cyclopentane-1,2-diol,

[1S-[1α,2α,3β,5β(1S*,2R*)]]-3-(Hydroxymethyl)-5-[7-[[2-(3,5-dimethylphenyl)cyclopropyl]amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Hydroxyethyl)-5-[5-(methylthio)-7-[(2-phenylcyclopropyl)amino]-3H-1,2,3-triazolo[4,5-d]pyrimidin-3-yl]-cyclopentane-1,2-diol,

[1R-[1α,2α,3β(1R*,2S*),5β]]-3-[5-(Butylthio)-7-[(2-phenylcyclopropyl)amino]-3H-1,2,3-triazolo[4,5-d]pyrimidin-3-yl]-5-(2-hydroxyethyl)-cyclopentane-1,2-diol,

[1R-[1α,2α,3β(1R*,2S*),5β]]-3-[7-[[2-(4-chlorophenyl)cyclopropyl]amino]-5-(propylthio)-3H-1,2,3-triazolo[4,5-d]pyrimidin-3-yl]-5-[(2-hydroxy)ethoxy]-cyclopentane-1,2-diol,

[1S-[1α,2α,3β,5β(1S*,2R*)]]-3-(Hydroxymethyl)-5-[7-[(2-phenycyclopropyl)amino]-5-[(3,3,3-trifluoropropyl)thio]-3H-1,2,3-triazolo[4,5-d]pyrimidin-3-yl]-cyclopentane-1,2-diol,

[1S-[1α,2β,3β,4α(1S*,2R*)]]-4-[7-[[2-(3-Chloro-4-methylphenyl)cyclopropyl]amino]-5-(propylthio)-3H-1,2,3-triazolo[4,5-d]pyrimidin-3-yl]-cyclopentane-1,2,3-triol, or pharmaceutically acceptable salts or solvates thereof.

9. A pharmaceutical composition comprising a compound according to claim 1 in combination with a pharmaceutically acceptable diluent, adjuvent or carrier.

10. A method of treatment of unstable angina, coronary angioplasty (PTCA), perithrombolysis, primary arterial thrombotic complications of atherosclerosis, arterial complications due to interventions in atherosclerotic disease, or thrombotic complications of surgical or mechanical damage, which comprises administering to a patient in need of such treatment a therapeutically effective amount of a compound according to claim 1.

11. A process for the preparation of a compound of formula (I) as defined in claim 1 which comprises;

(a) reacting a compound of formula (II):

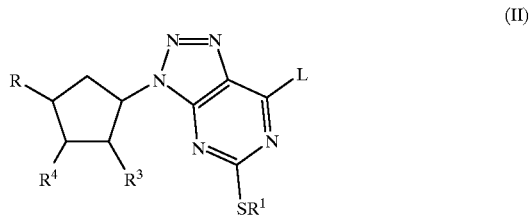

(II)

where R, $R^1$, $R^3$ and $R^4$ are as defined in formula (I) or are protected derivatives thereof, and L is a leaving group with a compound of formula (III):

$R^2NH_2$ (III)

where $R^2$ is as defined in formula (I) or is a protected derivative thereof, or (b) reacting a compound of formula (IV):

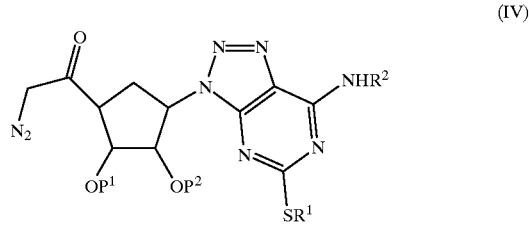

(IV)

in which $R^1$ and $R^2$ are as defined in formula (I) or are protected derivatives thereof and $P^1$ and $P^2$ are protecting groups or hydrogen, with a suitable reagent to introduce a substituent R, or, for compounds where m is 0:

(c) hydroxylation of a compound of formula (V):

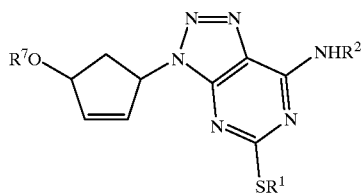

(V)

where $R^1$, $R^2$ and $R^7$ are as defined in formula (I) or are protected derivatives thereof, and optionally thereafter (a), (b) or (c) and in any order:
removing any protecting groups
forming a pharmaceutically acceptable salt or solvate.

12. A method of treatment of a condition selected from the group consisting of myocardial infarction, thrombotic stroke, transient ischaemic attack, peripheral vascular disease and angina, which comprises administering to a patient in need of such treatment an effective amount of a compound according to claim 1.

13. A method according to claim 12, wherein the condition is angina.

14. A method according to claim 10, wherein said interventions are selected from the group consisting of angioplasty, endarterectomy, stent placement, coronary surgery and other vascular graft surgery.

* * * * *